United States Patent
Sannomiya et al.

(10) Patent No.: US 9,716,238 B2
(45) Date of Patent: Jul. 25, 2017

(54) BORON COMPOUND FOR ORGANIC ELECTROLUMINESCENT ELEMENTS, AND ORGANIC ELECTROLUMINESCENT ELEMENT

(71) Applicant: NIPPON STEEL & SUMIKIN CHEMICAL CO., LTD., Chiyoda-ku, Tokyo (JP)

(72) Inventors: Rumi Sannomiya, Kitakyushu (JP); Masaki Komori, Kitakyushu (JP); Masashi Tada, Kitakyushu (JP); Takahiro Kai, Kitakyushu (JP); Toshihiro Yamamoto, Chiyoda-ku (JP)

(73) Assignee: NIPPON STEEL & SUMIKIN CHEMICAL CO., LTD., Tokyo (JP)

( * ) Notice: Subject to any disclaimer, the term of this patent is extended or adjusted under 35 U.S.C. 154(b) by 162 days.

(21) Appl. No.: 14/771,045

(22) PCT Filed: Feb. 24, 2014

(86) PCT No.: PCT/JP2014/054330
§ 371 (c)(1),
(2) Date: Aug. 27, 2015

(87) PCT Pub. No.: WO2014/132922
PCT Pub. Date: Sep. 4, 2014

(65) Prior Publication Data
US 2016/0020397 A1    Jan. 21, 2016

(30) Foreign Application Priority Data

Feb. 28, 2013  (JP) .................................. 2013-038758

(51) Int. Cl.
*H01L 51/00* (2006.01)
*C09K 11/06* (2006.01)
(Continued)

(52) U.S. Cl.
CPC .............. *H01L 51/008* (2013.01); *C07F 5/02* (2013.01); *C09K 11/025* (2013.01); *C09K 11/06* (2013.01);
(Continued)

(58) Field of Classification Search
USPC ................................................ 428/90; 257/40
See application file for complete search history.

(56) References Cited

U.S. PATENT DOCUMENTS

2010/0148162 A1   6/2010   Komori et al.
2012/0153272 A1   6/2012   Fukuzaki

FOREIGN PATENT DOCUMENTS

CN   102827196 A   12/2012
JP   2011-71460 A   4/2011
(Continued)

OTHER PUBLICATIONS

International Search Report, issued in PCT/JP2014/054330, dated Apr. 1, 2014.

*Primary Examiner* — J. L. Yang
(74) *Attorney, Agent, or Firm* — Birch, Stewart, Kolasch & Birch, LLP

(57) ABSTRACT

Provided are an organic EL device which is practically satisfactory in terms of a light-emitting characteristic, a driving voltage, and durability, and a compound for organic EL devices to be used in the device. The organic EL device is an organic EL device produced by laminating, on a substrate, an anode, a plurality of organic layers including a light-emitting layer, and a cathode, the organic EL device containing, in at least one organic layer selected from the light-emitting layer, a hole-transporting layer, an electron-transporting layer, a hole-blocking layer, and an electron-blocking layer, a boron compound having two indolocarbazolyl groups in a molecule thereof. The boron compound is represented by Y-L-B(A)a-L-Y or Y-L(Z)b-Y, where Y rep-
(Continued)

resents an indolocarbazolyl group, L represents an aromatic group, and Z represents a boron-containing group.

9 Claims, 1 Drawing Sheet

(51) Int. Cl.
    *C07F 5/02*         (2006.01)
    *C09K 11/02*       (2006.01)
    *H01L 51/50*       (2006.01)

(52) U.S. Cl.
    CPC ...... *H01L 51/0067* (2013.01); *H01L 51/0072* (2013.01); *H01L 51/0073* (2013.01); *H01L 51/0074* (2013.01); *C09K 2211/1011* (2013.01); *C09K 2211/1029* (2013.01); *C09K 2211/1033* (2013.01); *C09K 2211/1044* (2013.01); *C09K 2211/1059* (2013.01); *C09K 2211/1074* (2013.01); *C09K 2211/1077* (2013.01); *C09K 2211/1081* (2013.01); *C09K 2211/1085* (2013.01); *C09K 2211/1088* (2013.01); *C09K 2211/1092* (2013.01); *C09K 2211/185* (2013.01); *H01L 51/0085* (2013.01); *H01L 51/5012* (2013.01); *H01L 51/5016* (2013.01); *H01L 51/5096* (2013.01)

(56) References Cited

FOREIGN PATENT DOCUMENTS

| | | |
|---|---|---|
| KR | 10-2011-0011578 A | 2/2011 |
| WO | WO 2008/149691 A1 | 12/2008 |

BORON COMPOUND FOR ORGANIC ELECTROLUMINESCENT ELEMENTS, AND ORGANIC ELECTROLUMINESCENT ELEMENT

TECHNICAL FIELD

The present invention relates to a novel boron compound for an organic electroluminescent device and an organic electroluminescent device using the compound, and specifically, to a thin-film-type device which emits light when an electric field is applied to a light-emitting layer formed of an organic compound.

BACKGROUND ART

In general, an organic electroluminescent device (hereinafter referred to as organic EL device) includes a light-emitting layer and a pair of counter electrodes interposing the light-emitting layer therebetween in its simplest structure. That is, the organic EL device uses the phenomenon that, when an electric field is applied between both the electrodes, electrons are injected from a cathode and holes are injected from an anode, and each electron and each hole recombine in the light-emitting layer to emit light.

In recent years, progress has been made in developing an organic EL device using an organic thin film. In order to enhance luminous efficiency particularly, the optimization of the kind of electrodes has been attempted for the purpose of improving the efficiency of injection of carriers from the electrodes. As a result, there has been developed a device in which a hole-transporting layer formed of an aromatic diamine and a light-emitting layer formed of an 8-hydroxyquinoline aluminum complex (hereinafter referred to as Alq3) are formed between electrodes as thin films, resulting in a significant improvement in luminous efficiency, as compared to related-art devices in which a single crystal of anthracene or the like is used. Thus, the development of the above-mentioned organic EL device has been promoted in order to accomplish its practical application to a high-performance flat panel having features such as self-luminescence and rapid response.

Further, investigations have been made on using phosphorescent light rather than fluorescent light as an attempt to raise the luminous efficiency of a device. Many kinds of devices including the above-mentioned device in which a hole-transporting layer formed of an aromatic diamine and a light-emitting layer formed of Alq3 are formed emit light by using fluorescent light emission. However, by using phosphorescent light emission, that is, by using light emission from a triplet excited state, luminous efficiency is expected to be improved by from about three times to four times, as compared to the case of using related-art devices in which fluorescent light (singlet) is used. In order to accomplish this purpose, investigations have been made on adopting a coumarin derivative or a benzophenone derivative in a light-emitting layer, but extremely low luminance has only been provided. Further, investigations have been made on using a europium complex as an attempt to use a triplet state, but highly efficient light emission has not been accomplished. In recent years, many investigations on a phosphorescent light-emitting dopant material centered on an organic metal complex such as an iridium complex have been made, as described in Patent Literature 1, for the purpose of attaining high luminous efficiency and a long lifetime.

CITATION LIST

Patent Literature

[PTL 1] JP 2003-515897 A
[PTL 2] JP 2001-313178 A
[PTL 3] JP 11-162650 A
[PTL 4] JP 11-176578 A
[PTL 5] WO 2007/063754 A1
[PTL 6] WO 2008/149691 A1
[PTL 7] KR 10-2011-132721 A
[PTL 8] JP 2011-71460 A

In order to obtain high luminous efficiency, host materials which are used with the dopant materials described above play an important role. A typical example of the host materials proposed is 4,4'-bis(9-carbazolyl)biphenyl (hereinafter referred to as CBP) as a carbazole compound disclosed in Patent Literature 2. When CBP is used as a host material for a green phosphorescent light-emitting material typified by a tris(2-phenylpyridine)iridium complex (hereinafter referred to as $Ir(ppy)_3$), the injection balance between charges is disturbed because CBP has the characteristic of facilitating the delivery of holes and not facilitating the delivery of electrons. Thus, excessively delivered holes flow out into an electron-transporting layer side, with the result that the luminous efficiency from $Ir(ppy)_3$ lowers.

In order to provide high luminous efficiency to an organic EL device as described above, it is necessary to use a host material which has high triplet excitation energy, and is striking a good balance in both charge (hole and electron)-injecting/transporting property. Further desired is a compound that has electrochemical stability, has high heat resistance, and has excellent amorphous stability, and hence further improvement has been demanded.

Patent Literature 3 discloses an indolocarbazole compound having a diphenylamino group as a hole-transporting material. Patent Literature 4 discloses a diphenylindolocarbazole compound as a hole-transporting material. Patent Literatures 5 and 6 each disclose, as a phosphorescent host material, a compound containing two indolocarbazolyl groups in a molecule thereof, and each disclose that an organic EL device using the compound is improved in luminous efficiency and has high driving stability.

Patent Literatures 1 to 6 each disclose that a compound having an indolocarbazole skeleton is used in an organic EL device, but none of the literatures discloses a compound having a boron-containing group on an indolocarbazole skeleton. In addition, Patent Literature 7 teaches a compound substituted with various substituents on a substituent for linking two indolocarbazolyl groups and an indolocarbazole skeleton, but does not teach a compound having a boron-containing group on a group for linking two indolocarbazolyl groups or an indolocarbazole skeleton. Further, Patent Literature 8 discloses a compound having a boron-containing group as a group for linking three indolocarbazolyl groups, but does not teach a compound having a boron-containing group as a group for linking two indolocarbazolyl groups.

SUMMARY OF INVENTION

In order to apply an organic EL device to a display device in a flat panel display or the like, it is necessary to improve the luminous efficiency of the device and also to ensure sufficiently the stability in driving the device at a low driving voltage or the like. The present invention has an object to provide, in view of the above-mentioned circumstances, an organic EL device which has high efficiency, has high luminance stability when driven, and is practically useful and a compound suitable for the organic EL device.

The inventors of the present invention have made intensive investigations and have consequently found that, when a compound having an indolocarbazole skeleton with a specific structure is used in an organic EL device, the organic EL device exhibits excellent characteristics. As a result, the present invention has been completed.

According to one embodiment of the present invention, there is provided a compound for an organic electroluminescent device, which is represented by any one of the following general formulae (1) and (2).

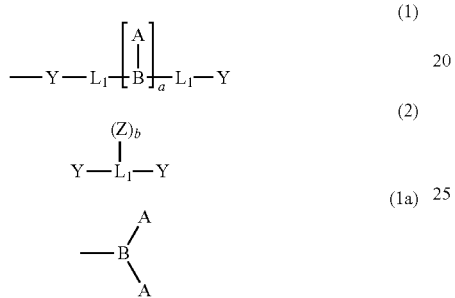

In the formulae:

$L_1$'s each independently represent a divalent or trivalent group selected from a substituted or unsubstituted aromatic hydrocarbon group having 6 to 18 carbon atoms, a substituted or unsubstituted aromatic heterocyclic group having 3 to 17 carbon atoms, and a linked aromatic group formed by linking 2 to 6 aromatic rings of the substituted or unsubstituted aromatic hydrocarbon group and the substituted or unsubstituted aromatic heterocyclic group, the linked aromatic group may be linear or branched, the aromatic rings to be linked may be identical to or different from each other, and when two $L_1$'s are contained in one molecule, the two $L_1$'s may be identical to or different from each other;

Z represents a boron-containing group represented by the formula (1a);

A's each independently represent hydrogen, deuterium, an alkyl group having 1 to 12 carbon atoms, an alkenyl group having 2 to 12 carbon atoms, an alkynyl group having 2 to 12 carbon atoms, an alkoxyl group having 1 to 12 carbon atoms, a hydroxyl group, chlorine, bromine, fluorine, a substituted or unsubstituted aromatic hydrocarbon group having 6 to 18 carbon atoms, or a substituted or unsubstituted aromatic heterocyclic group having 3 to 17 carbon atoms, and when A represents an alkyl group, an alkenyl group, an alkynyl group, an alkoxyl group, an aromatic hydrocarbon group, or an aromatic heterocyclic group, the groups adjacent to each other or substituents of the groups may be bonded to each other to form a ring, and the ring may be a heterocycle containing B or may be a fused ring;

Y's each independently represent an indolocarbazolyl group represented by the following formula (1b):

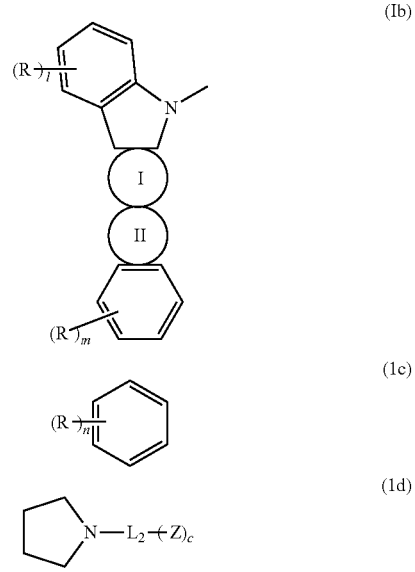

Herein, a ring I represents an aromatic hydrocarbon ring represented by the formula (1c) which fuses with an adjacent ring at an arbitrary position, a ring II represents a heterocycle represented by the formula (1d) which fuses with an adjacent ring at an arbitrary position, and $L_2$ has the same meaning as that of $L_1$ described above but represents a c+1-valent group;

Z has the same meaning as that of Z in the general formula (2), and when a plurality of Z's exist, the plurality of Z's may be identical to or different from each other.

R represents deuterium, an alkyl group having 1 to 12 carbon atoms, an aralkyl group having 7 to 19 carbon atoms, an alkenyl group having 2 to 12 carbon atoms, an alkynyl group having 2 to 12 carbon atoms, a cyano group, a dialkylamino group having 2 to 24 carbon atoms, a diarylamino group having 6 to 36 carbon atoms, a diaralkylamino group having 14 to 38 carbon atoms, an amino group, a nitro group, an acyl group having 2 to 12 carbon atoms, an alkoxycarbonyl group having 2 to 12 carbon atoms, a carboxyl group, an alkoxyl group having 1 to 12 carbon atoms, an alkylsulfonyl group having 1 to 12 carbon atoms, a haloalkyl group having 1 to 12 carbon atoms, a hydroxyl group, an amide group, a phenoxy group, an alkylthio group having 1 to 12 carbon atoms, a substituted or unsubstituted aromatic hydrocarbon group having 6 to 18 carbon atoms, a substituted or unsubstituted aromatic heterocyclic group having 3 to 17 carbon atoms, or a boron-containing group represented by the formula (1a).

l and m each independently represent an integer of from 0 to 4, and n represents an integer of from 0 to 2.

In the general formulae (1) and (2), a and b each represent an integer of 0 or 1, and c represents an integer of from 0 to 5, provided that in the general formula (1), l+m+n+a+c≥1, and in the general formula (2), l+m+n+b+c≥1, and when a+c or b+c equals 0, at least one R represents a boron-containing group represented by the formula (1a), and when l, m, n, b, or c represents 2 or more, a plurality of R's or Z's may be identical to or different from each other.

In the general formulae (1) and (2), Y's each represent an indolocarbazolyl group represented by any one of the general formulae (3) to (6).

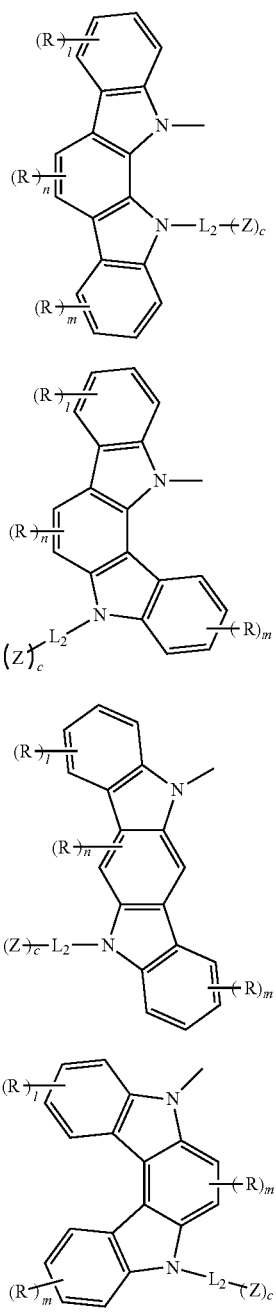

(In the formulae, $L_2$, Z, R, l, m, n, and c each have the same meaning as that in the formulae (1b) to (1d).)

In the general formulae (1) and (2), A's each independently represent an alkyl group having 1 to 12 carbon atoms, a substituted or unsubstituted aromatic hydrocarbon group having 6 to 18 carbon atoms, or a substituted or unsubstituted aromatic heterocyclic group having 3 to 17 carbon atoms. In addition, regarding $L_1$ and $L_2$, at least one of $L_1$ or $L_2$ represents a group having a fused ring structure.

In addition, according to one embodiment of the present invention, there is provided an organic electroluminescent device, including an organic layer containing the above-mentioned boron compound for an organic electroluminescent device.

According to another embodiment of the present invention, in the above-mentioned organic electroluminescent device, the organic layer containing the boron compound for an organic electroluminescent device includes at least one layer selected from a light-emitting layer, a hole-transporting layer, a hole-injecting layer, an electron-transporting layer, and an electron-injecting layer. According to still another embodiment of the present invention, in the above-mentioned organic electroluminescent device, the organic layer containing the boron compound for an organic electroluminescent device includes a light-emitting layer, and the light-emitting layer contains a phosphorescent light-emitting dopant and the compound for an organic electroluminescent device as a host material.

The boron compound for an organic electroluminescent device according to the one embodiment of the present invention has two indolocarbazolyl groups and at least one boron-containing group in a molecule thereof. A boron atom of the boron-containing group has an unoccupied orbital on its molecular orbital, and hence the group has a low lowest unoccupied molecular orbital (LUMO) energy level and has a characteristic by which an energy gap with respect to the valence band of a cathode is reduced. Accordingly, the use of the compound according to the one embodiment of the present invention in an organic EL device can be expected to exhibit an effect by which charge-injecting/transporting properties are improved and hence the voltage of the organic EL device is reduced.

The organic EL device using the compound according to the one embodiment of the present invention can realize a carrier balance optimum for various dopants in its light-emitting layer. As a result, an organic EL device significantly improved in light-emitting characteristics can be provided. In addition, the presence of two indolocarbazolyl groups in each molecule of the compound enables material design to which a solubility-improving function has been imparted, and hence can provide a material suitable for a wet process. Further, the compound can be improved in stability in each of activated states, i.e., oxidation, reduction, and excitation, and at the same time, has a good amorphous characteristic. Accordingly, the compound enables the realization of an organic EL device having a low driving voltage and high durability.

DESCRIPTION OF EMBODIMENTS

Figure 1:
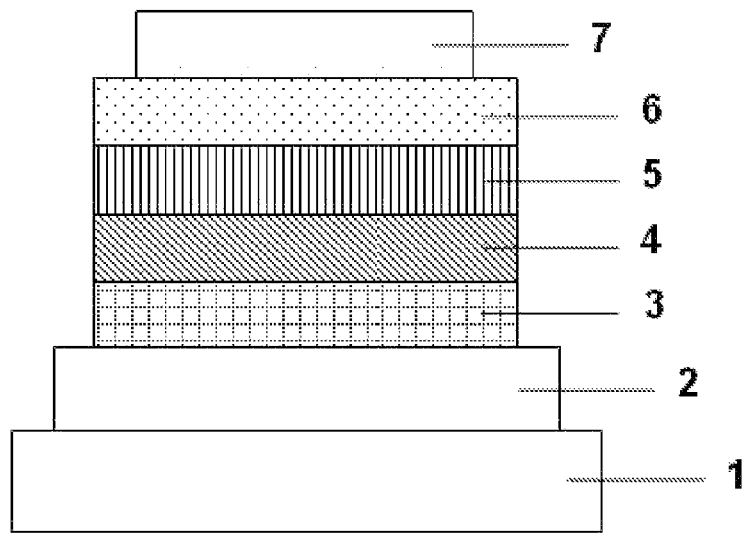
FIG. 1 is a sectional view for illustrating one structure example of an organic EL device.

A boron compound for an organic EL device of the present invention is represented by the general formula (1) or (2).

In the general formulae (1) and (2), $L_1$'s each represent a divalent group selected from a substituted or unsubstituted aromatic hydrocarbon group having 6 to 18 carbon atoms, a substituted or unsubstituted aromatic heterocyclic group having 3 to 17 carbon atoms, and a linked aromatic group formed by linking 2 to 6 aromatic rings of these groups. The linked aromatic group may be linear or branched, and the aromatic rings to be linked may be identical to or different from each other. In addition, two $L_1$'s may be identical to or different from each other.

Specific examples of the case where L₁ represents an unsubstituted aromatic hydrocarbon group, aromatic heterocyclic group, or linked aromatic group include: a group produced by removing two or three hydrogen atoms from an aromatic compound such as benzene, pentalene, indene, naphthalene, anthracene, phenanthrene, pyrrole, imidazole, pyrazole, thiazole, thiophene, pyridine, pyrazine, pyrimidine, pyridazine, triazine, isoindole, indazole, purine, benzimidazole, indolizine, chromene, benzoxazole, isobenzofuran, quinolizine, isoquinoline, imidazole, naphthyridine, phthalazine, quinazoline, quinoxaline, cinnoline, quinoline, pteridine, perimidine, phenanthroline, phenanthridine, acridine, phenazine, phenothiazine, phenoxazine, phenazasiline, dibenzodioxin, carboline, indole, indoloindole, carbazole, furan, benzofuran, isobenzofuran, benzothiazole, oxanthrene, dibenzofuran, thiophene, thioxanthene, thianthrene, phenoxathiin, thionaphthene, isothianaphthene, thiophthene, thiophanthrene, or dibenzothiophene; and a group produced by removing two or three hydrogen atoms from an aromatic compound in which two to six of such groups are linked.

As a substituent in the case where L₁ represents an aromatic hydrocarbon group having a substituent, an aromatic heterocyclic group having a substituent, or a linked aromatic group having a substituent, there is given deuterium, an alkyl group having 1 to 12 carbon atoms, an aralkyl group having 7 to 19 carbon atoms, an alkenyl group having 2 to 12 carbon atoms, an alkynyl group having 2 to 12 carbon atoms, a cyano group, a dialkylamino group having 2 to 24 carbon atoms, a diarylamino group having 6 to 36 carbon atoms, a diaralkylamino group having 14 to 38 carbon atoms, an amino group, a nitro group, an acyl group, an alkoxycarbonyl group having 2 to 12 carbon atoms, a carboxyl group, an alkoxyl group having 1 to 12 carbon atoms, an alkylsulfonyl group having 1 to 12 carbon atoms, a haloalkyl group having 1 to 12 carbon atoms, a hydroxyl group, an amide group, a phenoxy group, or an alkylthio group having 1 to 12 carbon atoms. Of those, the following substituent is preferred: deuterium, an alkyl group having 1 to 12 carbon atoms, an aralkyl group having 7 to 19 carbon atoms, an alkenyl group having 2 to 12 carbon atoms, an alkynyl group having 2 to 12 carbon atoms, a dialkylamino group having 2 to 24 carbon atoms, a diarylamino group having 6 to 36 carbon atoms, a diaralkylamino group having 14 to 38 carbon atoms, an acyl group having 2 to 12 carbon atoms, an alkoxycarbonyl group having 2 to 12 carbon atoms, an alkoxyl group having 1 to 12 carbon atoms, an alkylsulfonyl group having 1 to 12 carbon atoms, a haloalkyl group having 1 to 12 carbon atoms, a phenoxy group, or an alkylthio group having 1 to 12 carbon atoms.

Here, when L₁ represents an unsubstituted divalent or trivalent linked aromatic group, the linked aromatic group is, for example, a group produced by removing two or three hydrogen atoms from such a group as represented by any one of the following formulae (7) to (9).

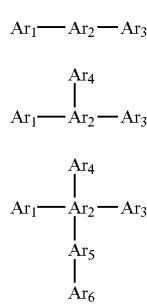

In the formulae (7) to (9), Ar₁ to Ar₆ each represent an unsubstituted monocyclic or fused aromatic ring, and the rings may be identical to or different from one another. Here, a group to be bonded to nitrogen of an indolocarbazole ring is preferably a fused ring.

Specific examples of the case where L₁ represents an unsubstituted linked aromatic group include groups each produced by removing one or two hydrogen atoms from the following groups.

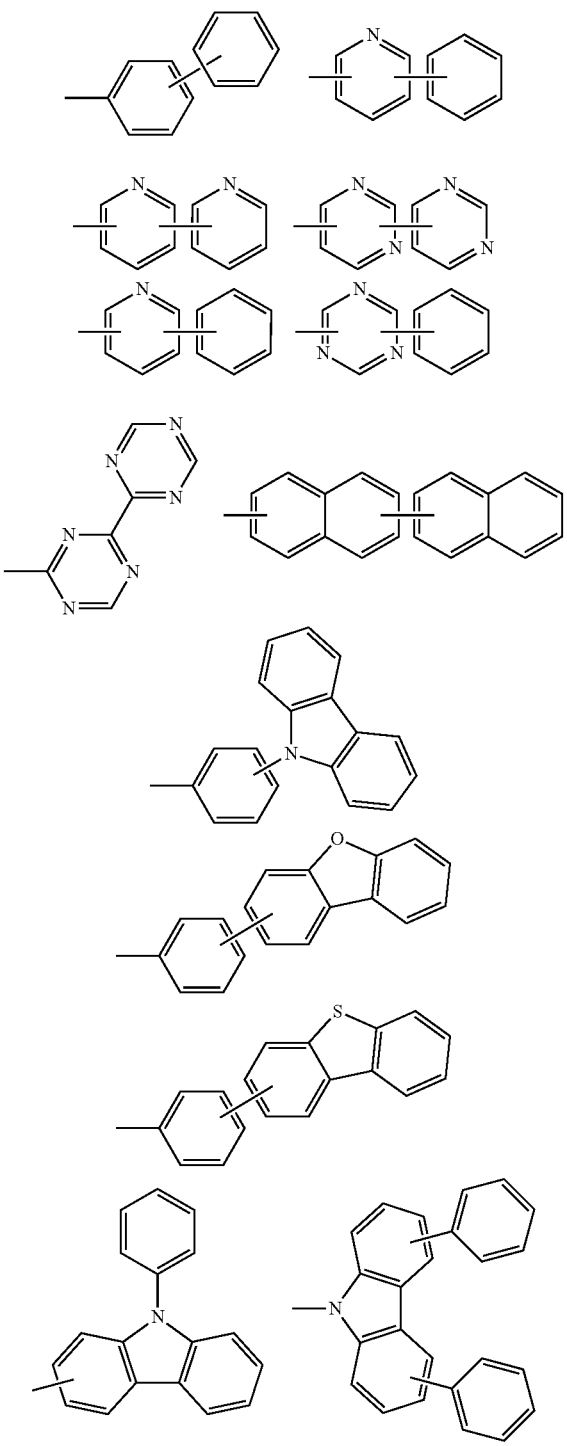

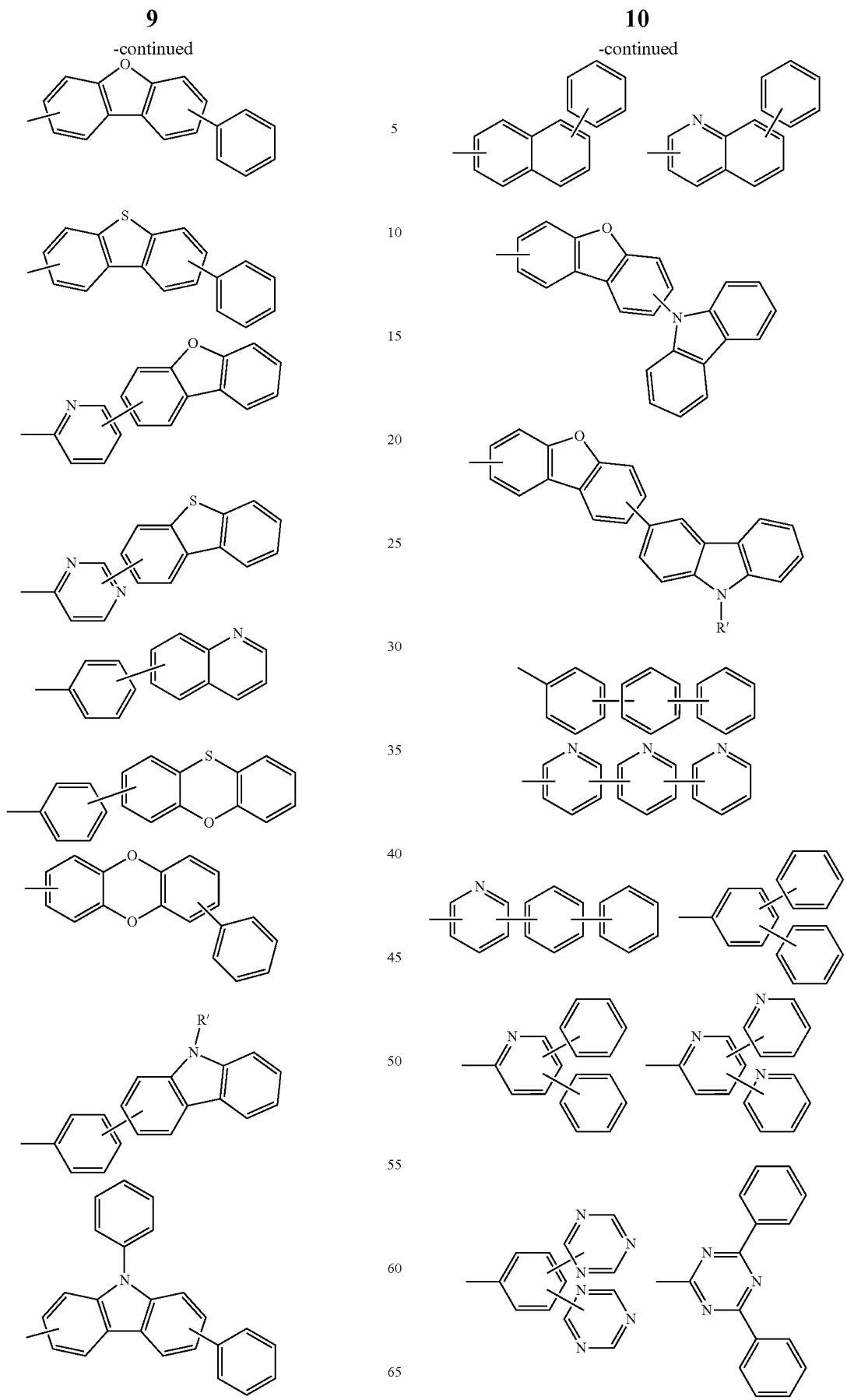

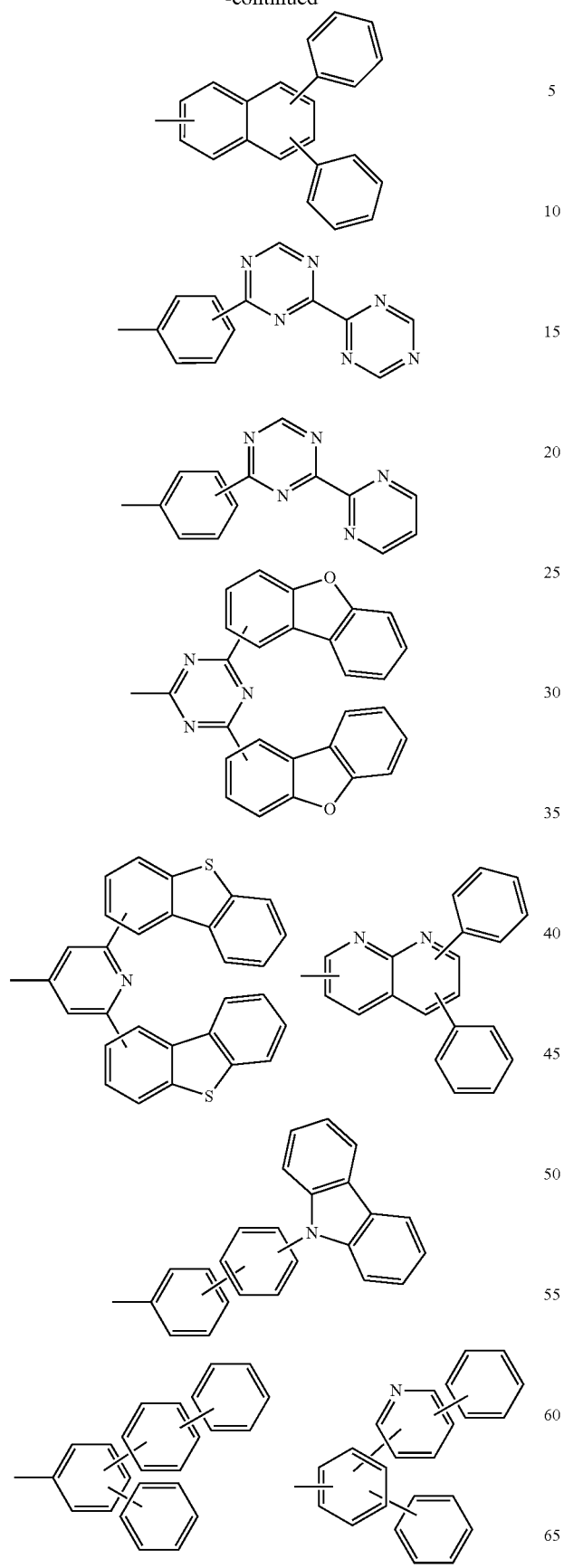
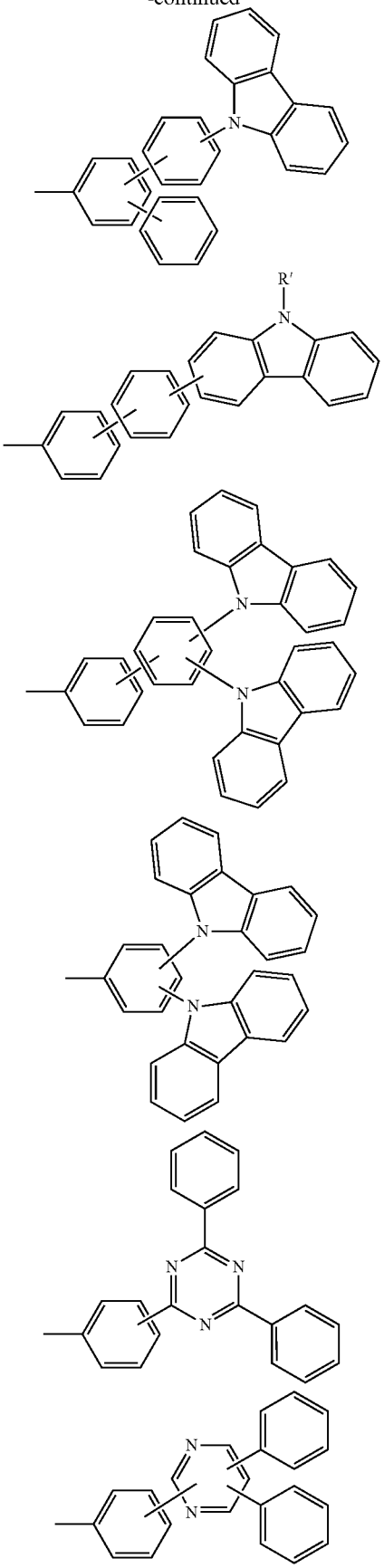

-continued
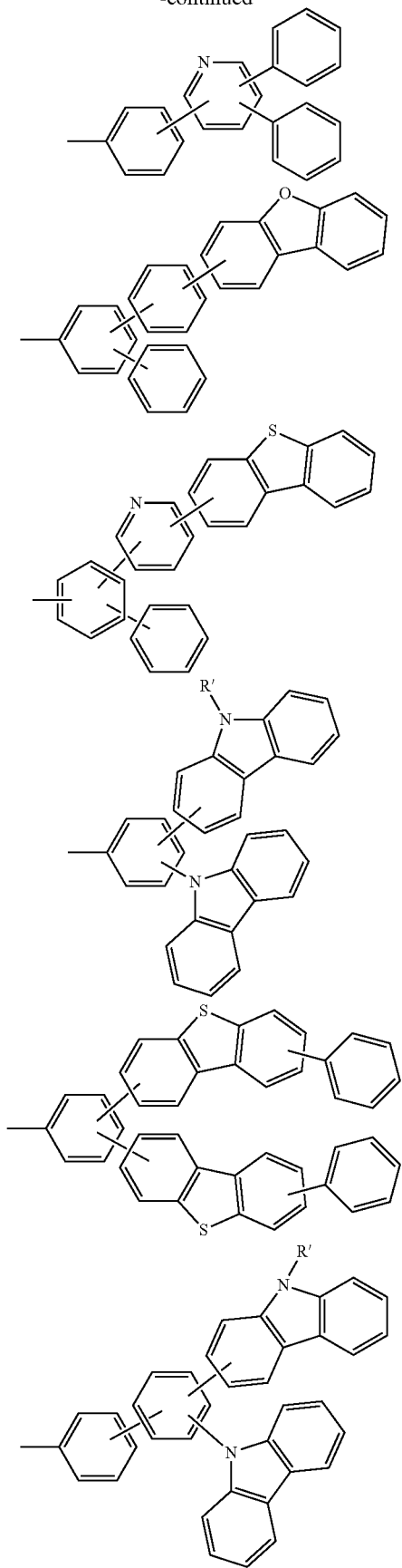
-continued
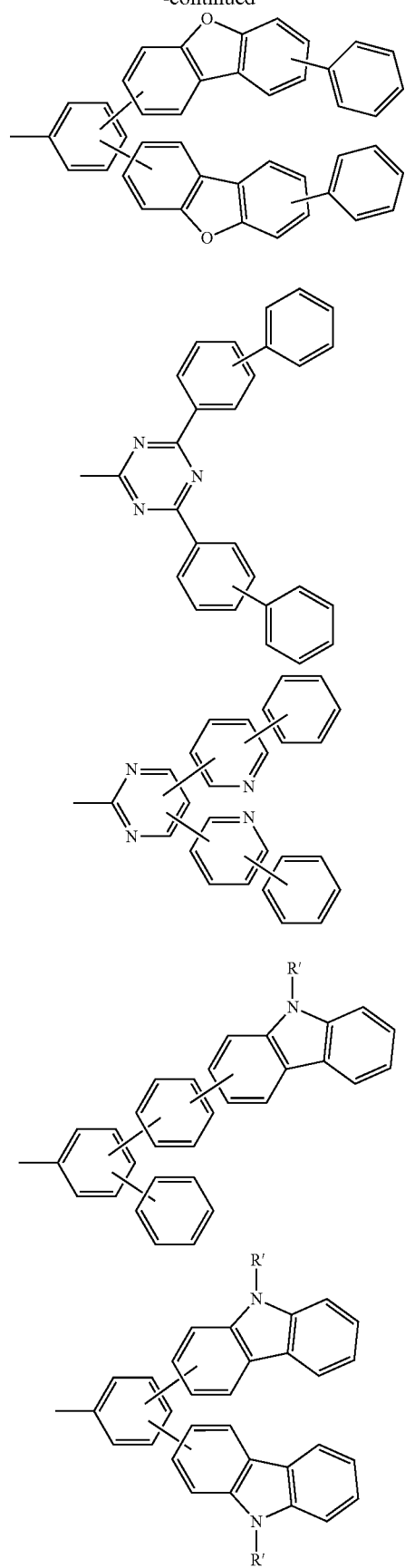

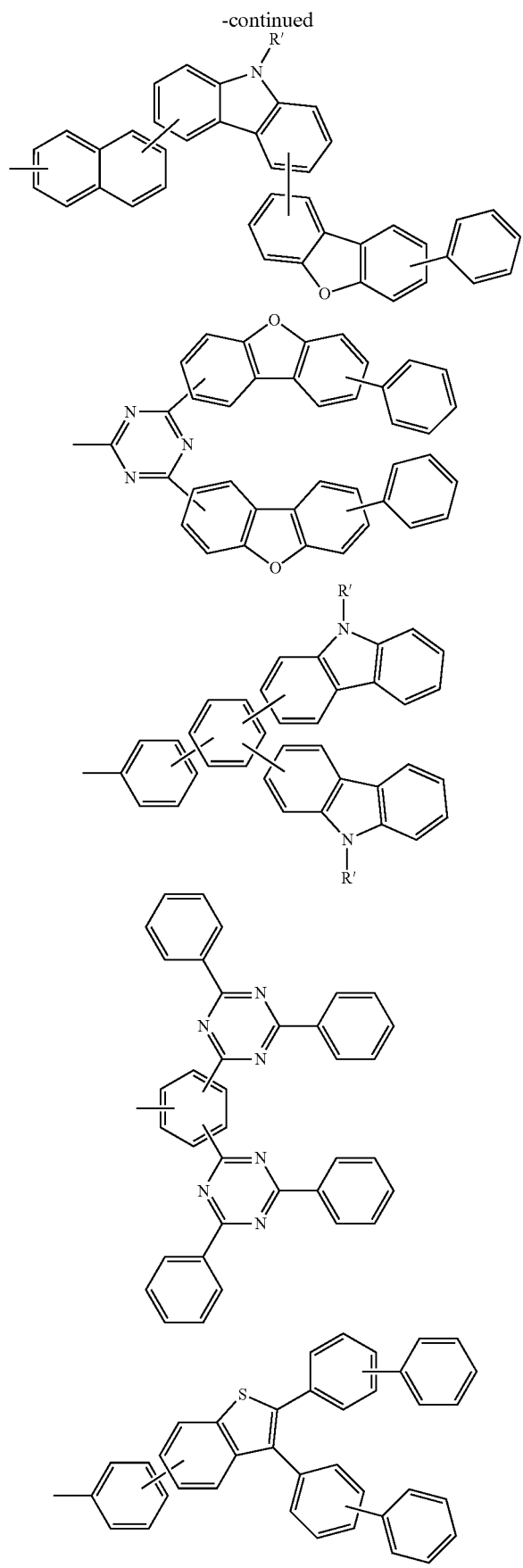
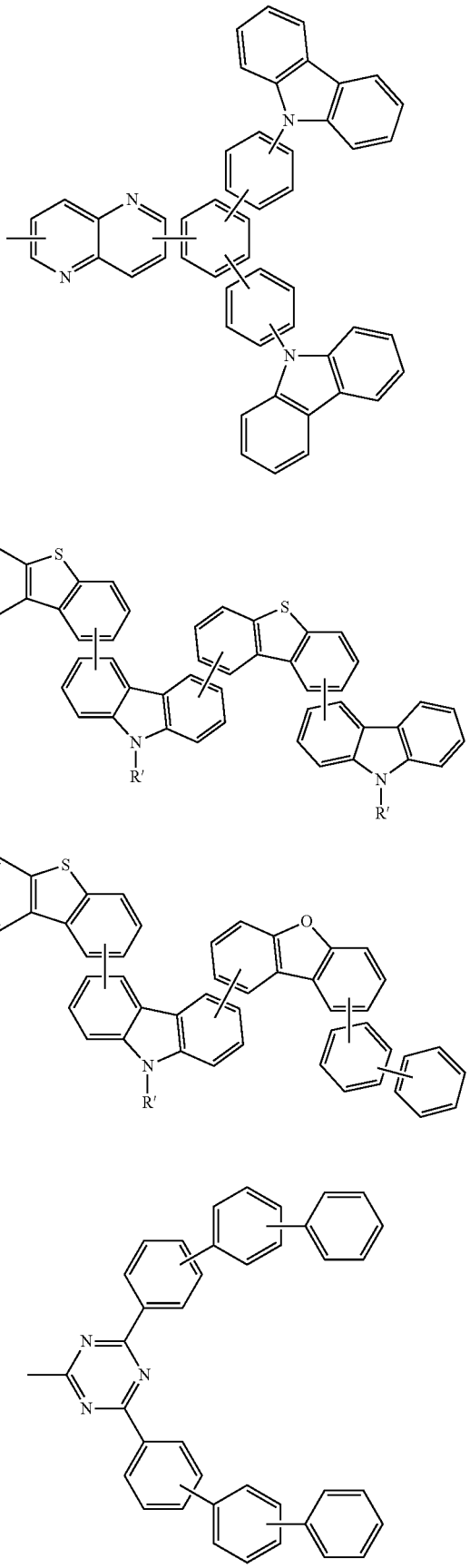

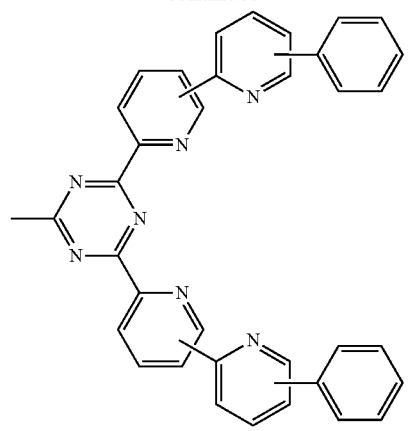
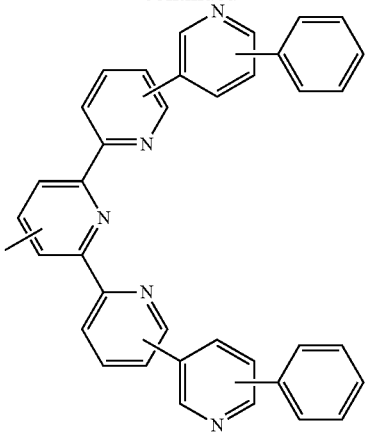
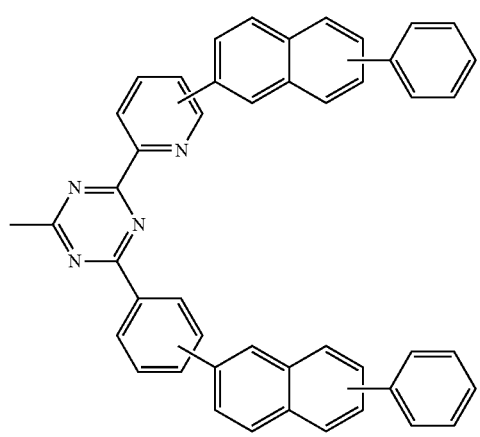
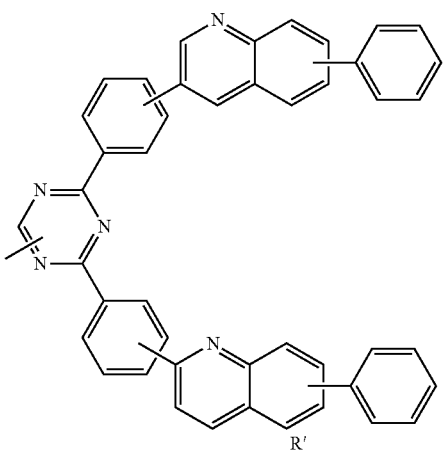
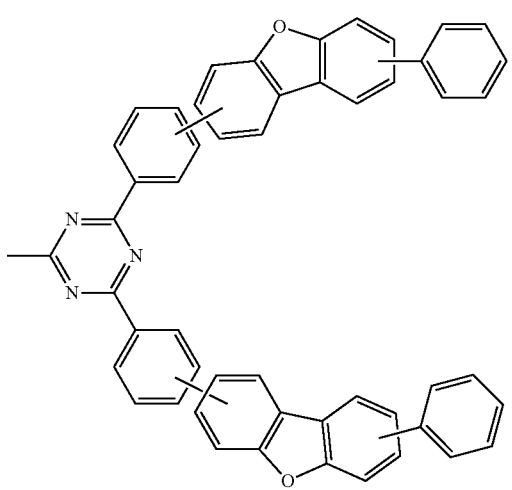
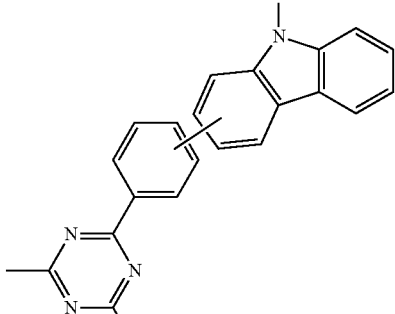
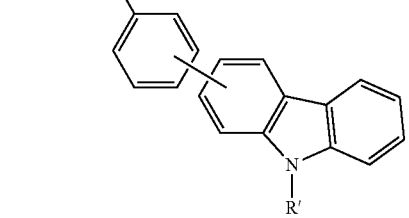
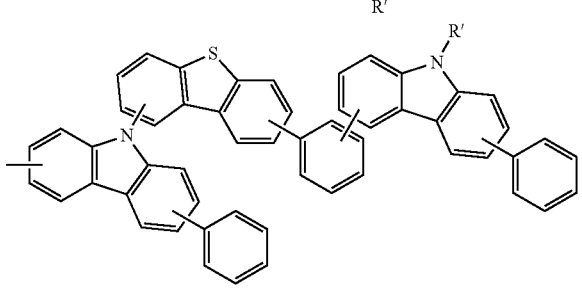

In the formulae, R' represents an aromatic hydrocarbon group having 6 to 18 carbon atoms or an aromatic heterocyclic group having 3 to 17 carbon atoms. Specific examples of the aromatic hydrocarbon group and the aromatic heterocyclic group are the same as those described for $L_1$ except that each of the groups is monovalent.

In the general formulae (1) and (2), A represents hydrogen, deuterium, an alkyl group having 1 to 12 carbon atoms, an alkenyl group having 2 to 12 carbon atoms, an alkynyl group having 2 to 12 carbon atoms, an alkoxyl group having 1 to 12 carbon atoms, a hydroxyl group, chlorine, bromine, fluorine, a substituted or unsubstituted aromatic hydrocarbon group having 6 to 18 carbon atoms, or a substituted or unsubstituted aromatic heterocyclic group having 3 to 17 carbon atoms, preferably represents a substituted or unsubstituted aromatic hydrocarbon group having 6 to 18 carbon atoms, or a substituted or unsubstituted aromatic heterocyclic group having 3 to 17 carbon atoms. When A represents an alkyl group, an alkenyl group, an alkynyl group, an alkoxyl group, an aromatic hydrocarbon group, or an aromatic heterocyclic group, the groups adjacent to each other or substituents of the groups may be bonded to each other to form a ring, and the ring may be a heterocycle containing B or may be a fused ring;

A substituent in the case where A represents an aromatic hydrocarbon group having a substituent or an aromatic heterocyclic group having a substituent is, for example, deuterium, an alkyl group having 1 to 12 carbon atoms, an aralkyl group having 7 to 19 carbon atoms, an alkenyl group having 2 to 12 carbon atoms, an alkynyl group having 2 to 12 carbon atoms, a cyano group, a dialkylamino group having 2 to 24 carbon atoms, a diarylamino group having 6 to 36 carbon atoms, a diaralkylamino group having 14 to 38 carbon atoms, an amino group, a nitro group, an acyl group, an alkoxycarbonyl group having 2 to 12 carbon atoms, a carboxyl group, an alkoxyl group having 1 to 12 carbon atoms, an alkylsulfonyl group having 1 to 12 carbon atoms, a haloalkyl group having 1 to 12 carbon atoms, a hydroxyl group, chlorine, bromine, fluorine, anamide group, a phenoxy group, an alkylthio group having 1 to 12 carbon atoms, an aromatic hydrocarbon group having 6 to 18 carbon atoms, or an aromatic heterocyclic group having 3 to 17 carbon atoms. A preferred substituent is deuterium, an alkyl group having 1 to 12 carbon atoms, an aralkyl group having 7 to 19 carbon atoms, an alkenyl group having 2 to 12 carbon atoms, an alkynyl group having 2 to 12 carbon atoms, an aromatic hydrocarbon group having 6 to 18 carbon atoms, or an aromatic heterocyclic group having 3 to 17 carbon atoms.

In the general formulae (1) and (2), Y's each represent an indolocarbazolyl group represented by the formula (1b).

In the formula (1b), a ring I represents an aromatic hydrocarbon ring represented by the formula (1c), which fuses with an adjacent ring at an arbitrary position, and a ring II represents a heterocycle represented by the formula (1d), which fuses with an adjacent ring at an arbitrary position.

The indolocarbazolyl group represented by the formula (1b) has an indolocarbazole skeleton. In the indolocarbazole skeleton, the aromatic hydrocarbon ring represented by the formula (1c) can fuse with two adjacent rings at arbitrary positions, but at some positions, the ring cannot structurally fuse with the adjacent rings. The aromatic hydrocarbon ring represented by the formula (1c) has six sides but does not fuse with the two adjacent rings on two adjacent sides. In addition, the heterocycle represented by the formula (1d) can fuse with two adjacent rings at arbitrary positions, but at some positions, the ring cannot structurally fuse with the adjacent rings. That is, the heterocycle represented by the formula (1d) has five sides but does not fuse with the two adjacent rings on two adjacent sides, and does not fuse with an adjacent ring on a side containing a nitrogen atom. Therefore, the kinds of the indolocarbazole skeletons are limited.

In the formula (1b), the indolocarbazole skeleton is preferably a skeleton represented by any one of the following structures. Preferred positions at which the aromatic hydrocarbon ring and the heterocycle fuse in the indolocarbazole skeleton are understood from these examples.

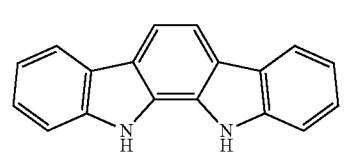

(IC-1)

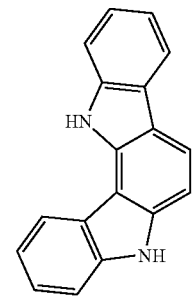

(IC-2)

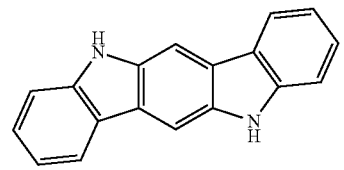

(IC-3)

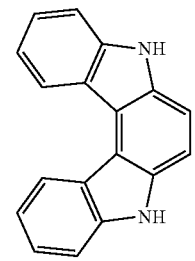

(IC-4)

In the formula (1d), $L_2$ represents a c+1-valent group. $L_2$ has the same meaning as that of $L_1$ in the general formula (2)

except that the valences of the groups do not coincide with each other in some cases. Here, $L_2$ may be identical to or different from any other $L_1$ present in a molecule of the compound.

Z's in the general formula (1) and the formula (1d) each represent a boron-containing group represented by the formula (1a). A in the formula (1a) has the same meaning as that of A in the general formula (1), and two A's may be identical to or different from each other.

In the formulae (1b) and (1c), R's each independently represent deuterium, an alkyl group having 1 to 12 carbon atoms, an aralkyl group having 2 to 12 carbon atoms, an alkenyl group having 2 to 12 carbon atoms, an alkynyl group having 2 to 12 carbon atoms, a cyano group, a dialkylamino group having 2 to 24 carbon atoms, a diarylamino group having 6 to 36 carbon atoms, a diaralkylamino group having 14 to 38 carbon atoms, an amino group, a nitro group, an acyl group having 2 to 12 carbon atoms, an alkoxycarbonyl group having 2 to 12 carbon atoms, a carboxyl group, an alkoxyl group having 1 to 12 carbon atoms, an alkylsulfonyl group having 1 to 12 carbon atoms, a haloalkyl group having 1 to 12 carbon atoms, a hydroxyl group, an amide group, a phenoxy group, an alkylthio group having 1 to 12 carbon atoms, a substituted or unsubstituted aromatic hydrocarbon group having 6 to 18 carbon atoms, a substituted or unsubstituted aromatic heterocyclic group having 3 to 17 carbon atoms, or a boron-containing group represented by the formula (1d), preferably deuterium, an alkyl group having 1 to 12 carbon atoms, a cycloalkyl group having 3 to 10 carbon atoms, a substituted or unsubstituted aromatic hydrocarbon group having 6 to 12 carbon atoms, a substituted or unsubstituted aromatic heterocyclic group having 3 to 12 carbon atoms, or a boron-containing group represented by the formula (1d). The substituent in the case where R represents an aromatic hydrocarbon group having a substituent or an aromatic heterocyclic group having a substituent has the same meaning as the substituent in the case where $L_1$ represents an aromatic hydrocarbon group having a substituent or an aromatic heterocyclic group having a substituent.

In the formulae (1b) and (1c), l and m each independently represent an integer of from 0 to 4, and n represents an integer of from 0 to 2.

In the general formulae (1) and (2), and the formulae (1b) to (1d), a and b each represent an integer of 0 or 1, and c represents an integer of from 0 to 5. Here, l+m+n+(a or b)+c≥1 and it is preferred that l+m+n+(a or b)+c=1.

In addition, when a+c or b+c equals 0, at least one R represents a boron-containing group represented by the formula (1d). When l, m, n, or b represents 2 or more, a plurality of R's or Z's may be identical to or different from each other.

In the formula (1d), $L_2$ has the same meaning as that of $L_1$ in the general formula (1) or (2) except that $L_2$ represents a c+1-valent group. In the general formulae (1) and (2), and the formula (1d), it is preferred that at least one of $L_1$ or $L_2$ represent a group having a fused ring structure, and it is more preferred that one of $L_1$ and $L_2$ represent a group having a fused ring structure.

Preferred examples of the indolocarbazolyl group represented by the formula (1b) include indolocarbazolyl groups each represented by any one of the general formulae (3) to (6). In the general formulae (3) to (6), symbols common to the general formulae (1) and (2), and the formulae (1b) to (1d) have the same meanings. In addition, in the general formulae (1) to (6), and the formulae (1b) to (1d), common symbols have the same meanings unless otherwise stated.

A skeleton represented by any one of the formulae (IC-1) to (IC-4) is given as a preferred indolocarbazole skeleton in the indolocarbazolyl group represented by the formula (1b). The formula (1b) is a concept encompassing the skeletons represented by the formulae (IC-1) to (IC-4), and these skeletons can be described by taking the indolocarbazolyl group represented by the formula (1b) as a typical example.

Such skeletons as represented in the forms of the formulae (IC-1) to (IC-4) are each conceivable as the skeleton of the indolocarbazolyl group represented by the formula (1b), and these skeletons can each be synthesized by employing a known approach from a raw material selected in accordance with the structure of a target compound.

For example, the indolocarbazole skeleton represented by the formula (IC-1) can be synthesized by the following reaction formula with reference to a synthesis example described in Synlett, 2005, No. 1, p 42-48.

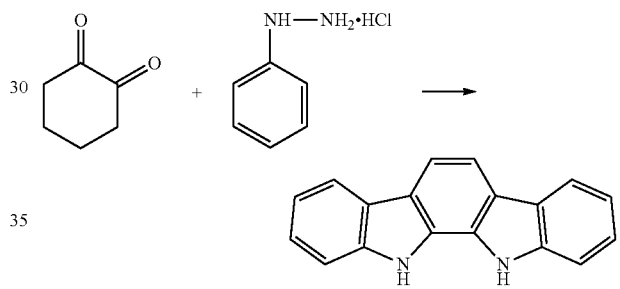

In addition, the indolocarbazole skeleton represented by the formula (IC-3) can be synthesized by the following reaction formula with reference to a synthesis example described in Archiv der Pharmazie (Weinheim, Germany) 1987, 320(3), p 280-2.

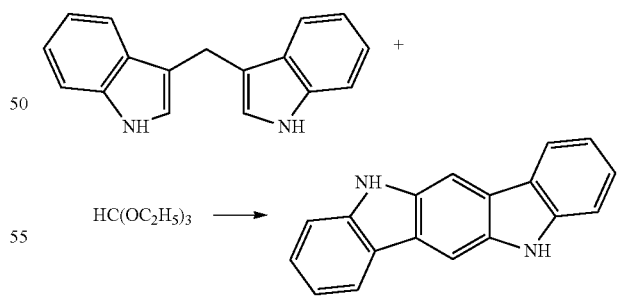

The boron compound represented by the general formula (1) or (2) has a structure in which two indolocarbazolyl groups (Y's) are bonded to boron through $L_1$, and one or two A's are bonded to boron. Specific examples of the boron compound represented by the general formula (1) or (2) are shown below, but the boron compound for an organic electroluminescent device of the present invention is not limited to these examples.

23
A1
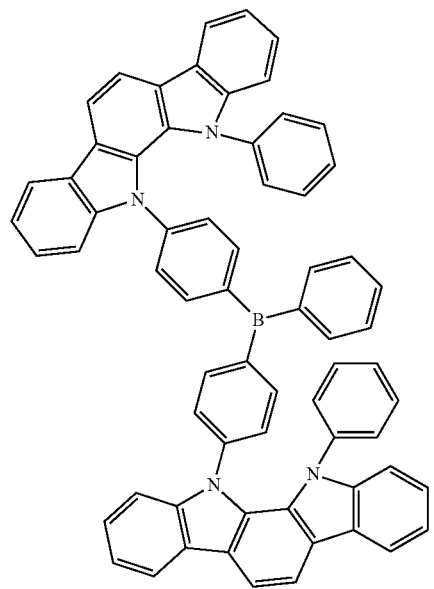
24
A2
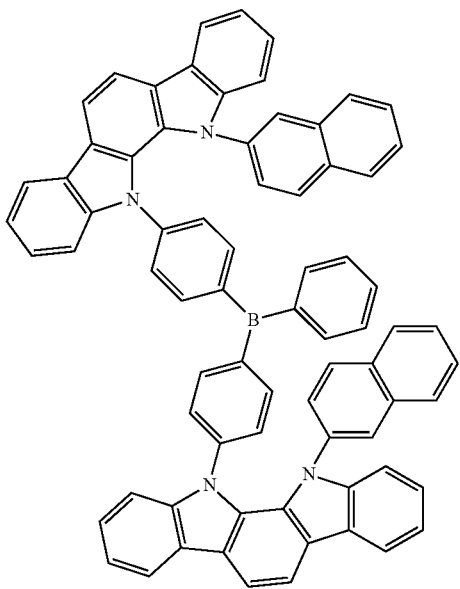
A3
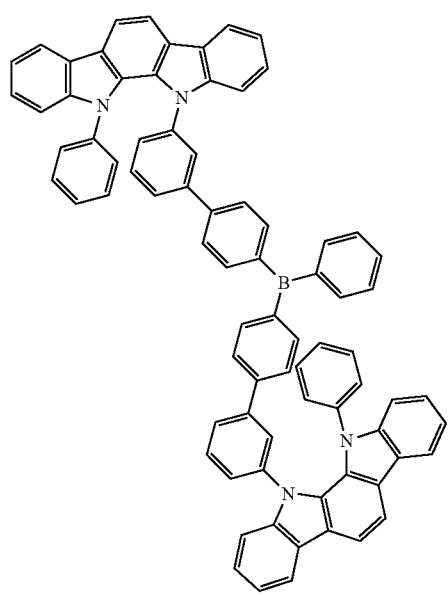
A4
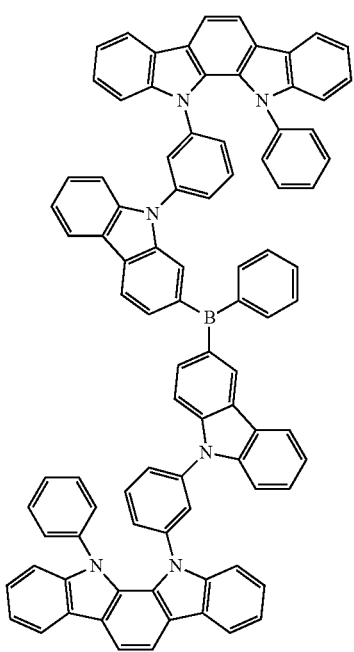

-continued
A5
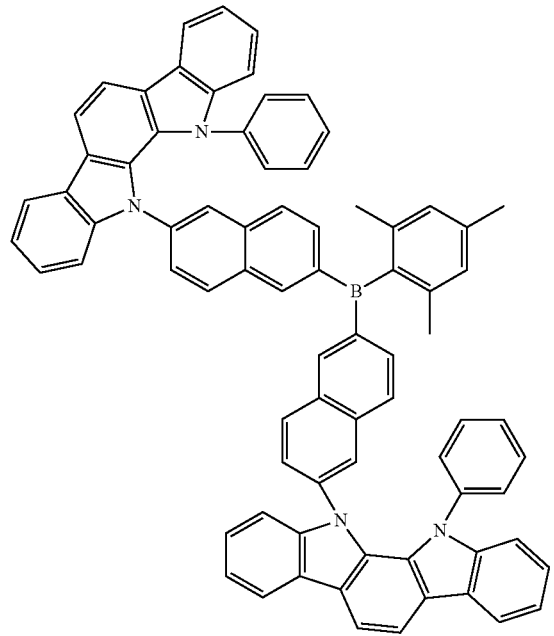
A6
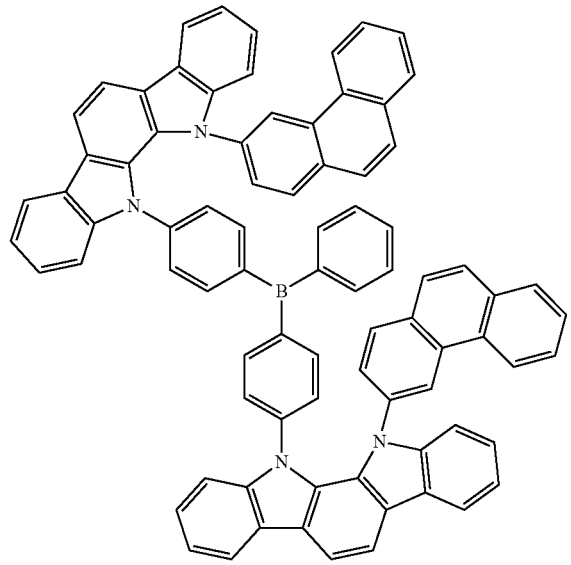
A7
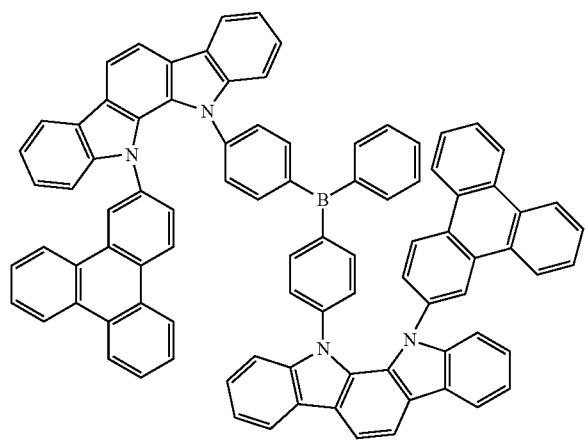
A8
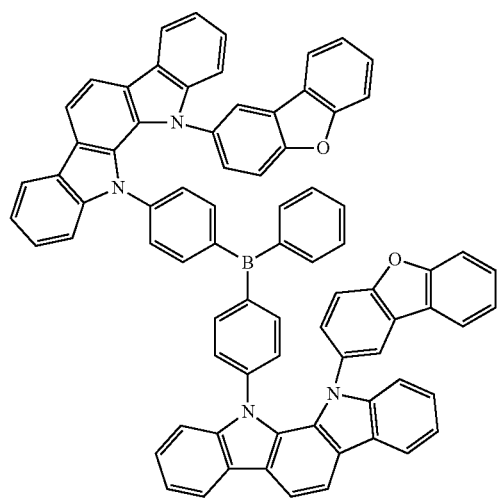

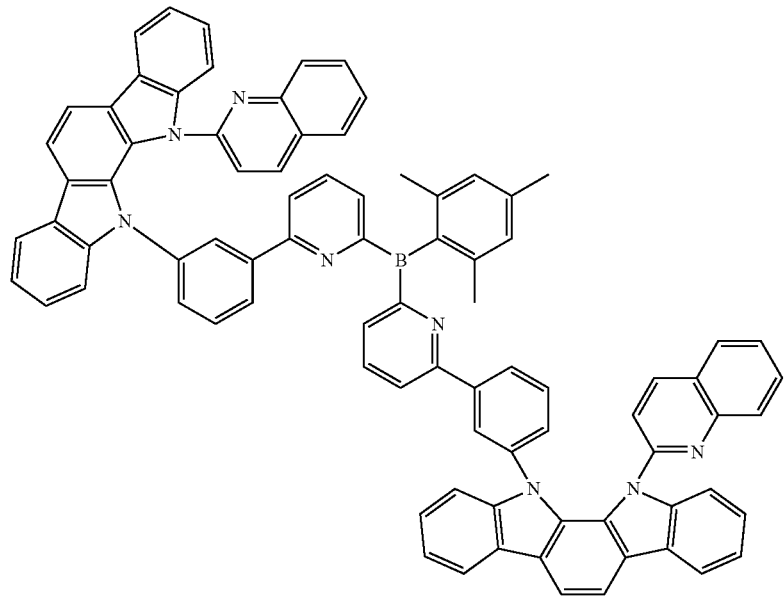
A9
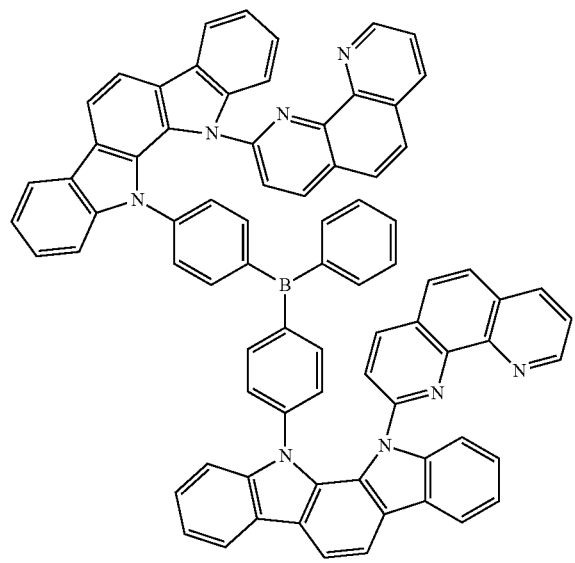
A10
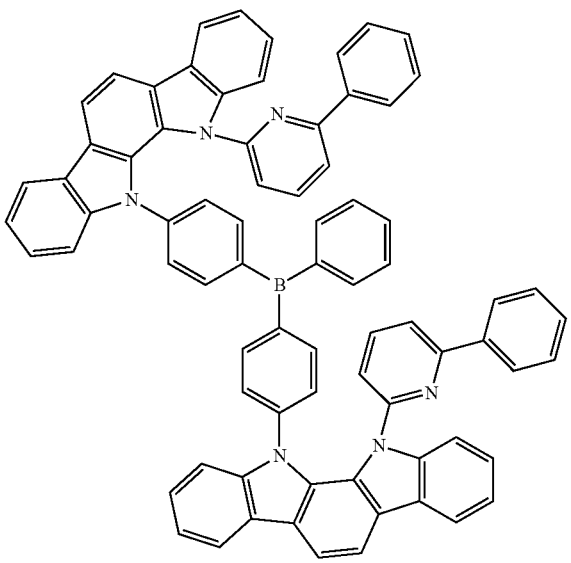
A11

-continued
A12
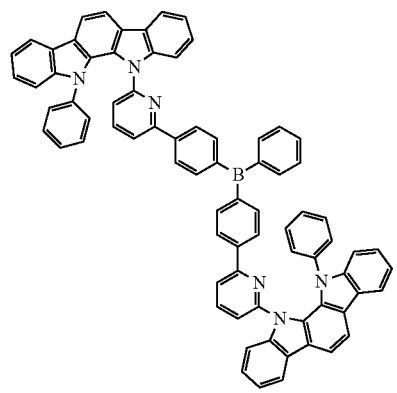
A13
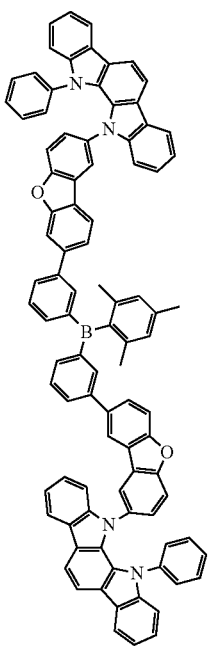
A14
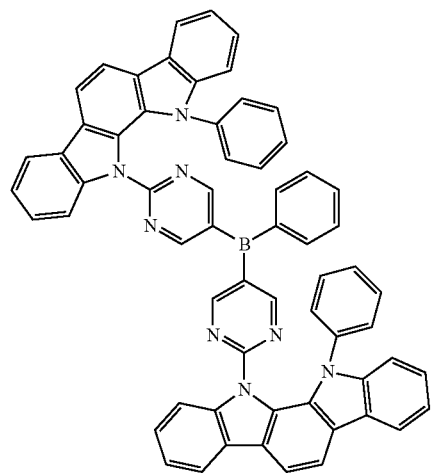
A15
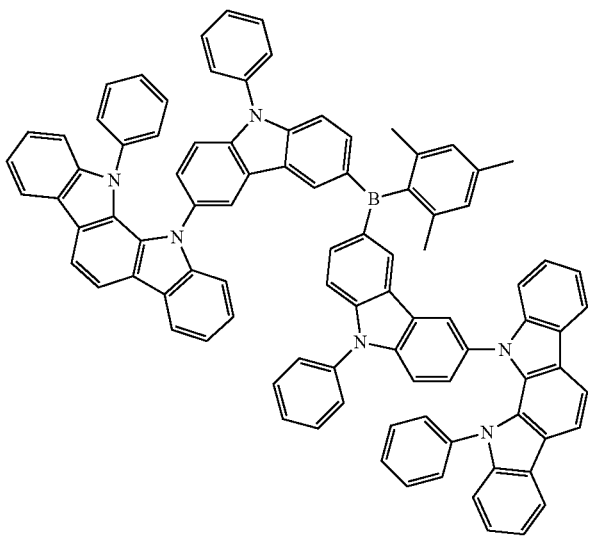

-continued
A16
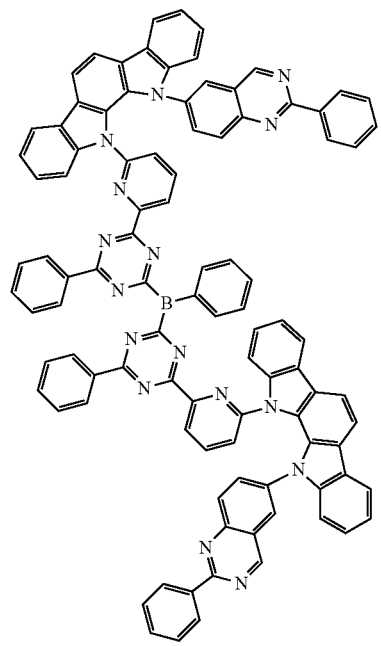
A17
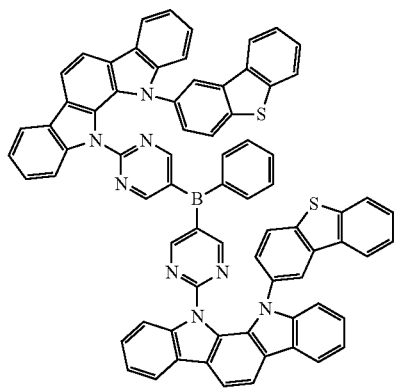
A18
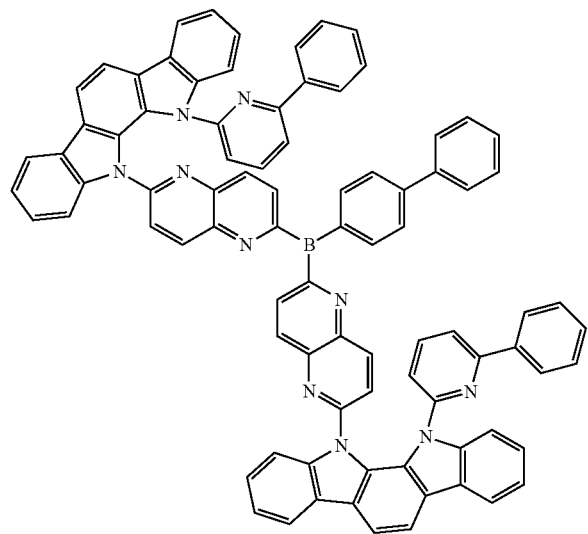
A19
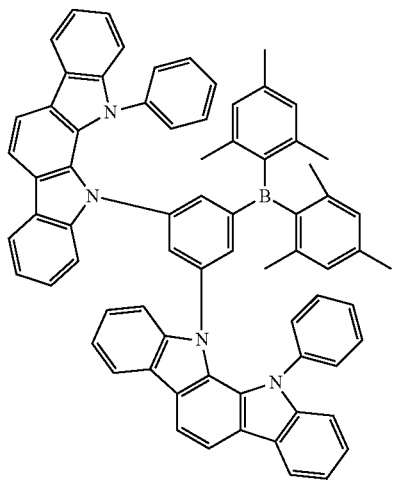

-continued
A20
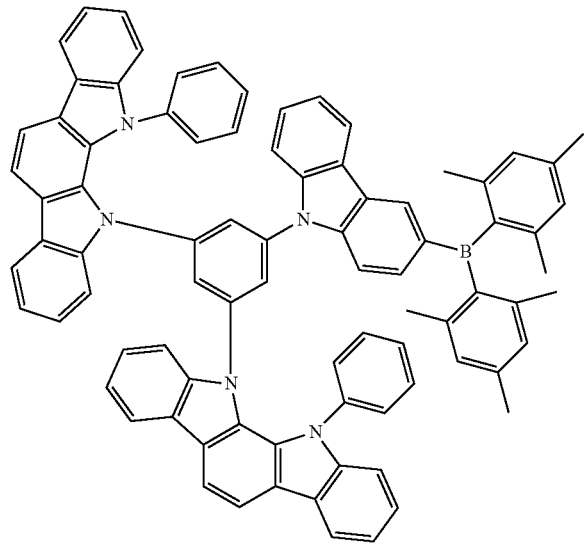
A21
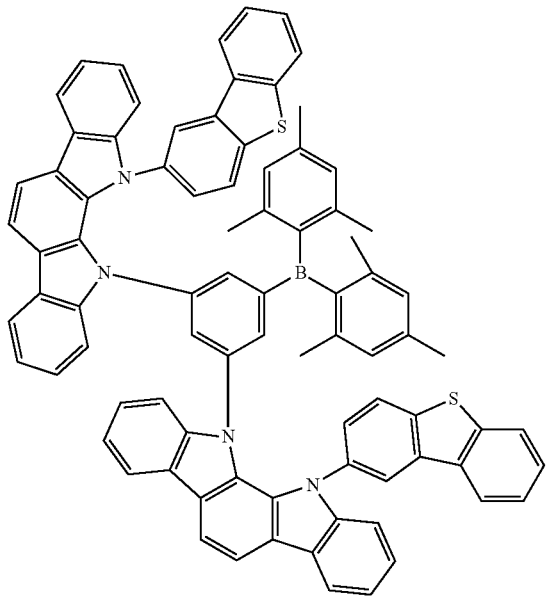
A22
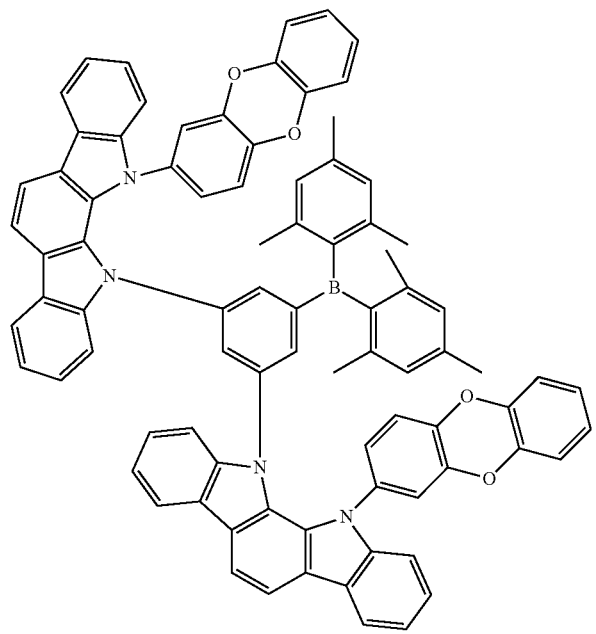
A23
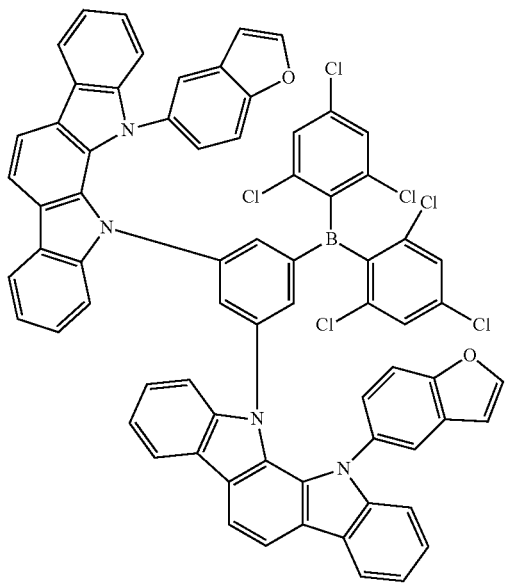

A24
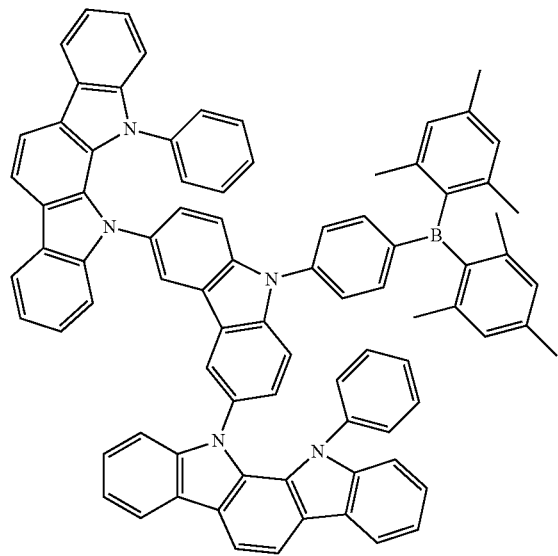
A25
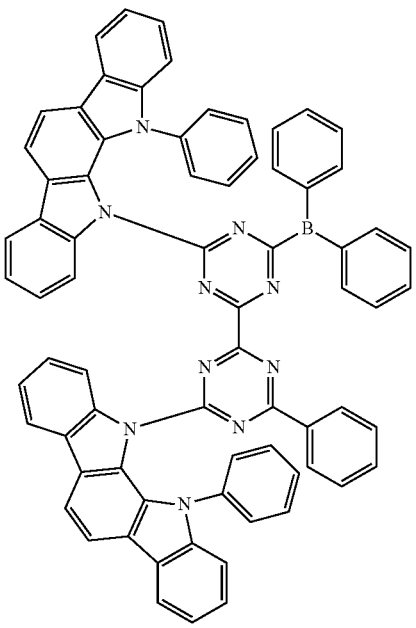
A26
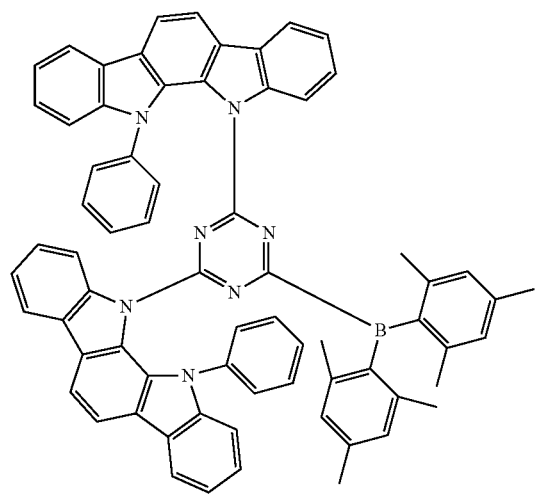
A27
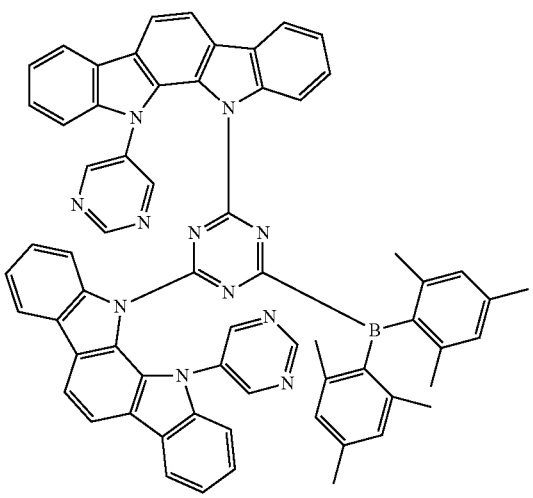

-continued
A28
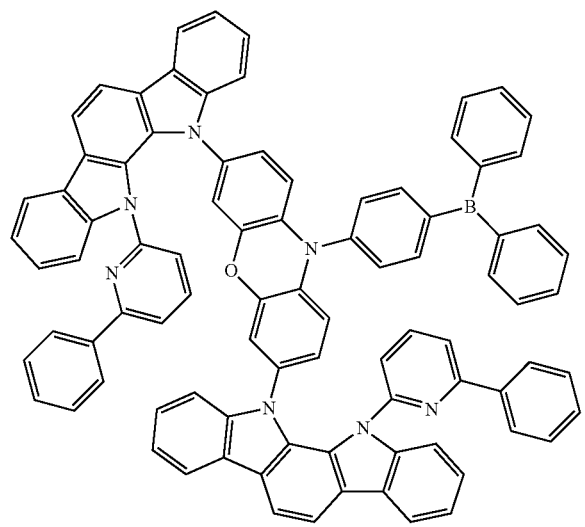
A29
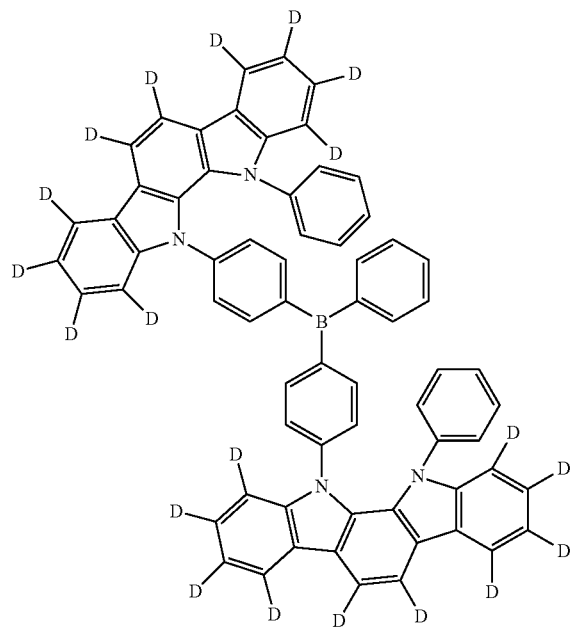
A30
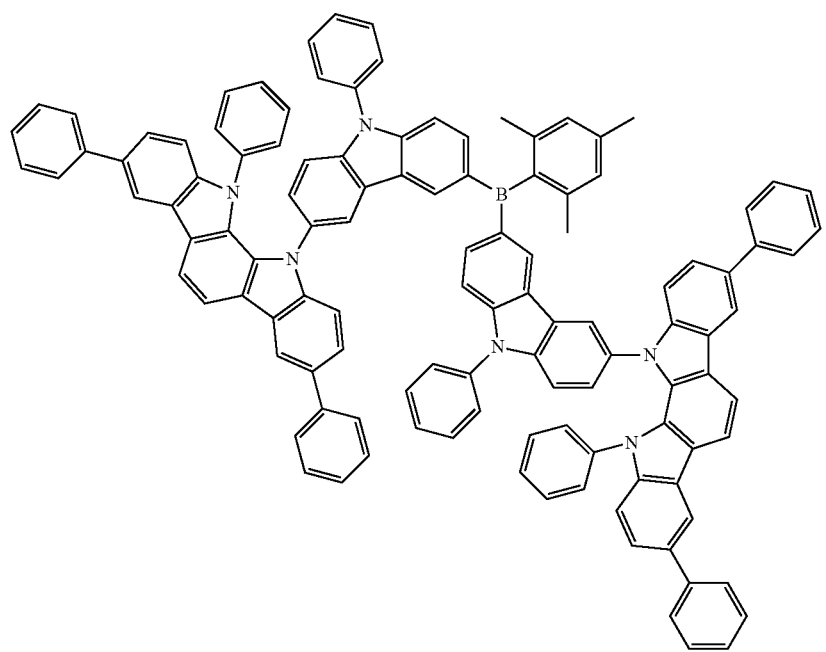

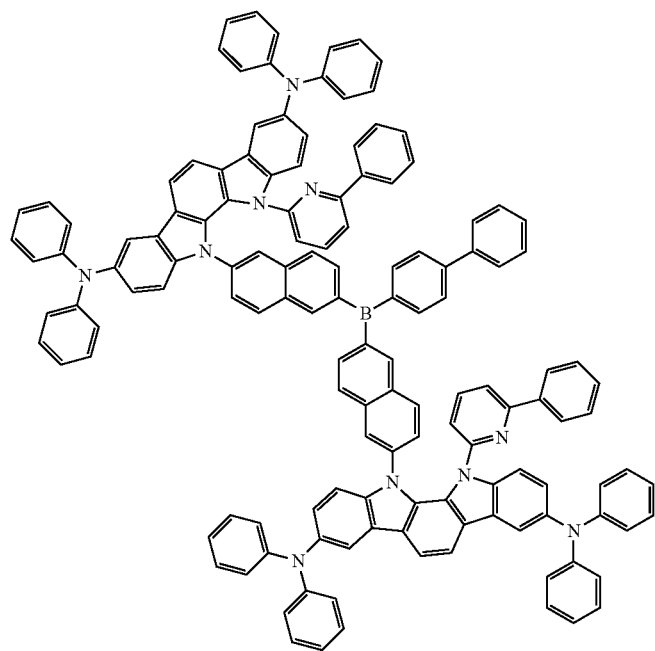
A31
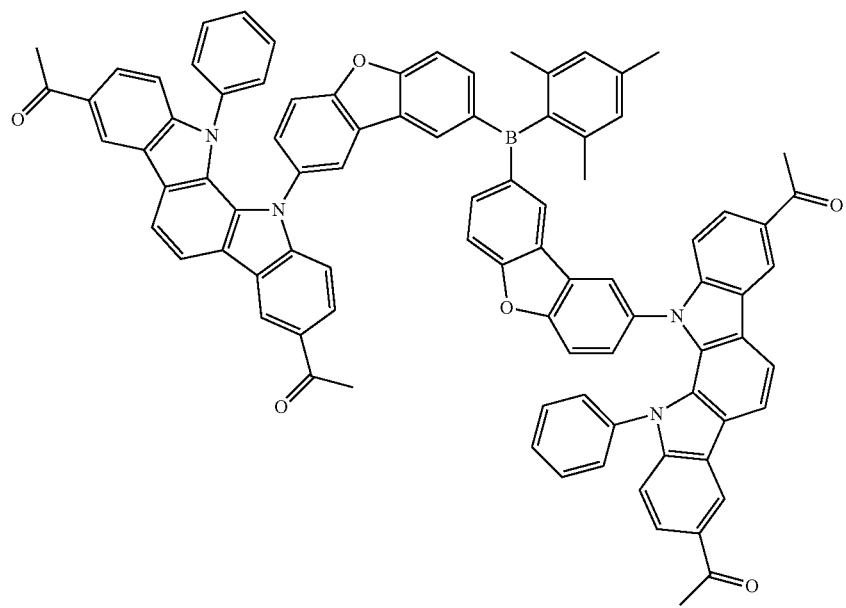
A32

-continued
A33
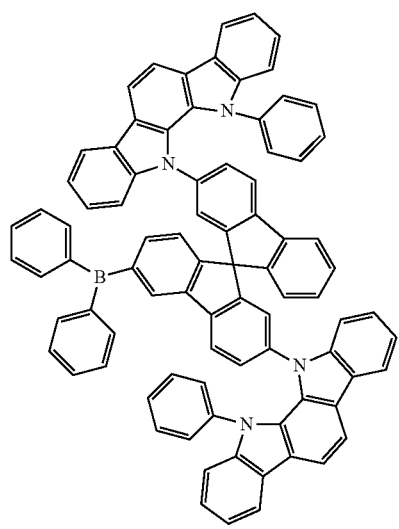
A34
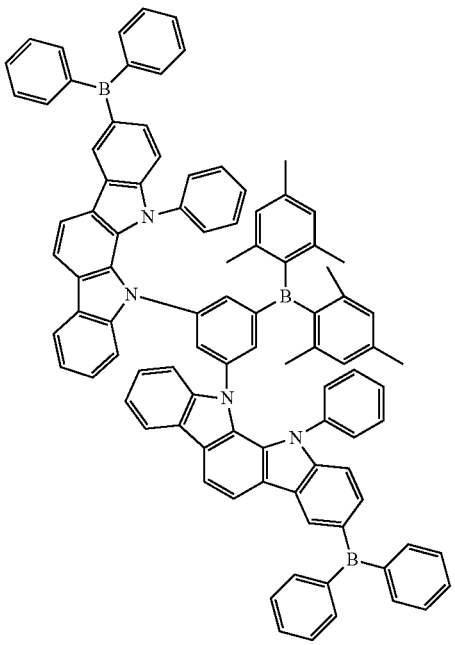
A35
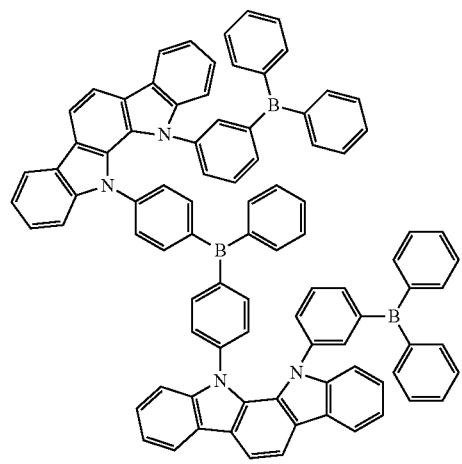
A35b
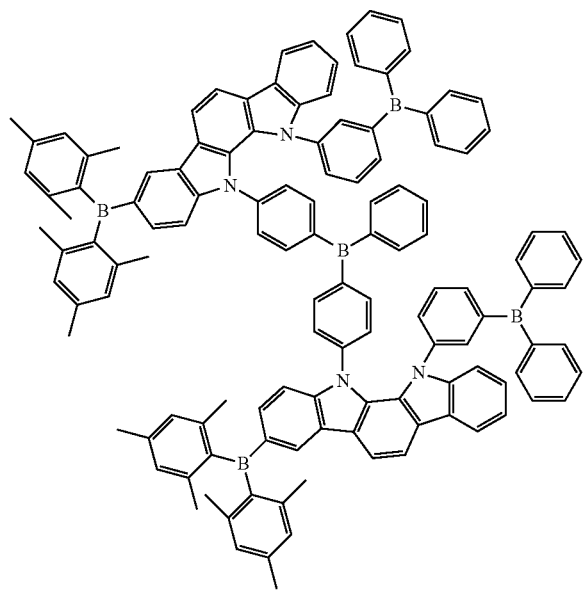

-continued
A36
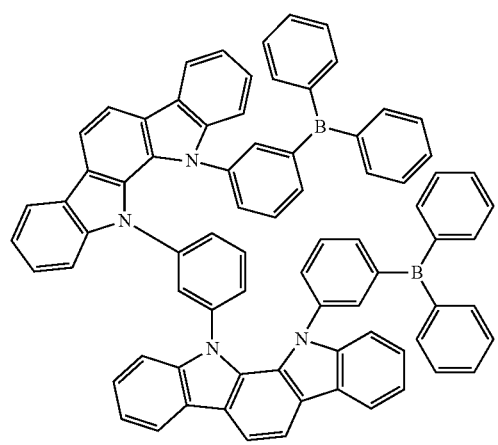
A37
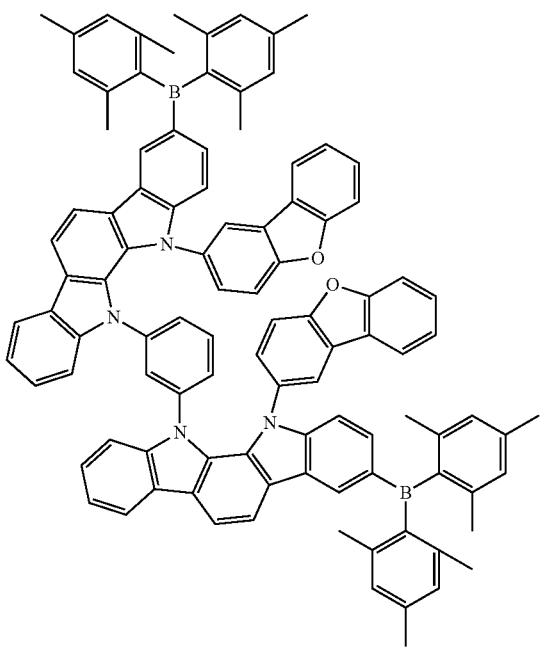
A38
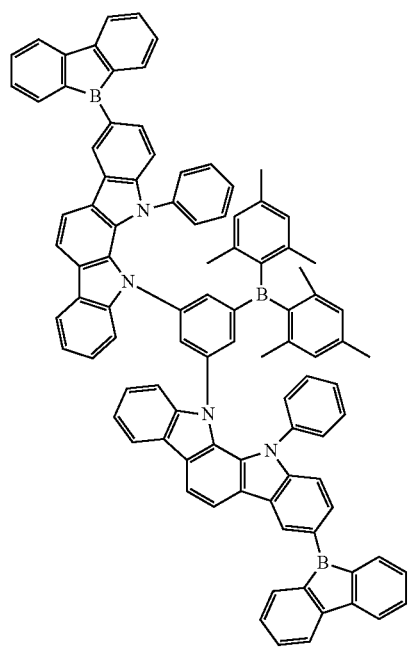
A39
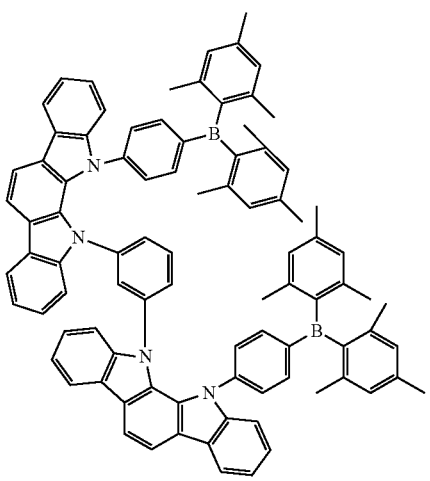

-continued
A40
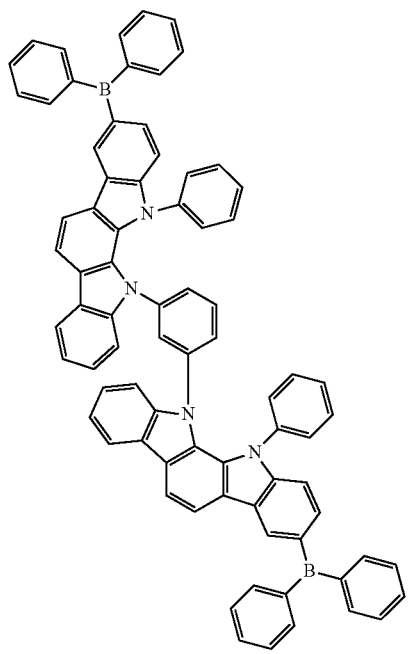
B1
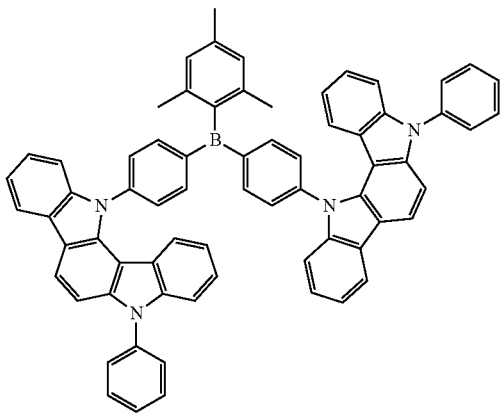
B2
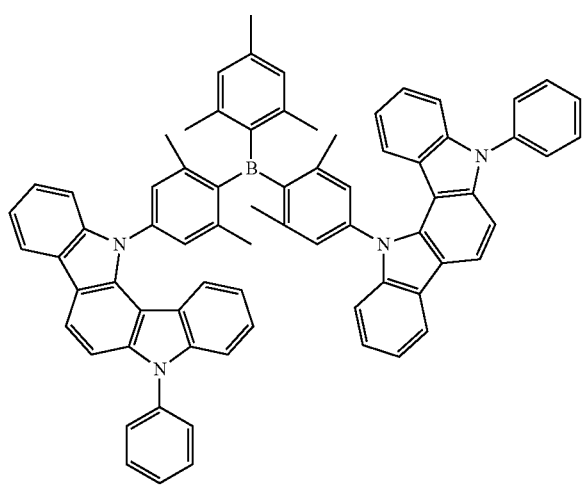
B3
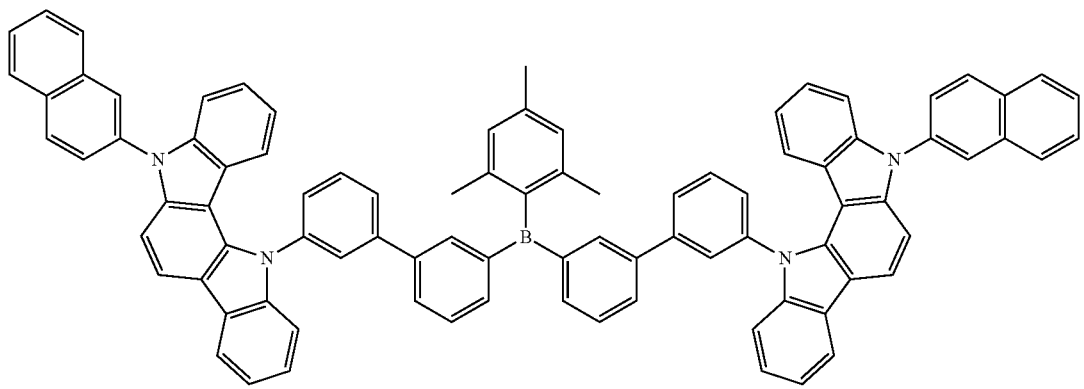

-continued
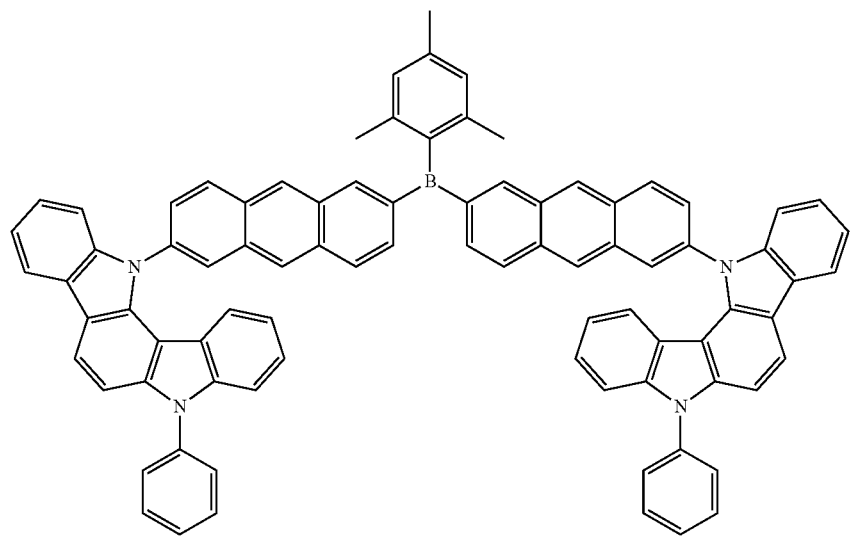
B4
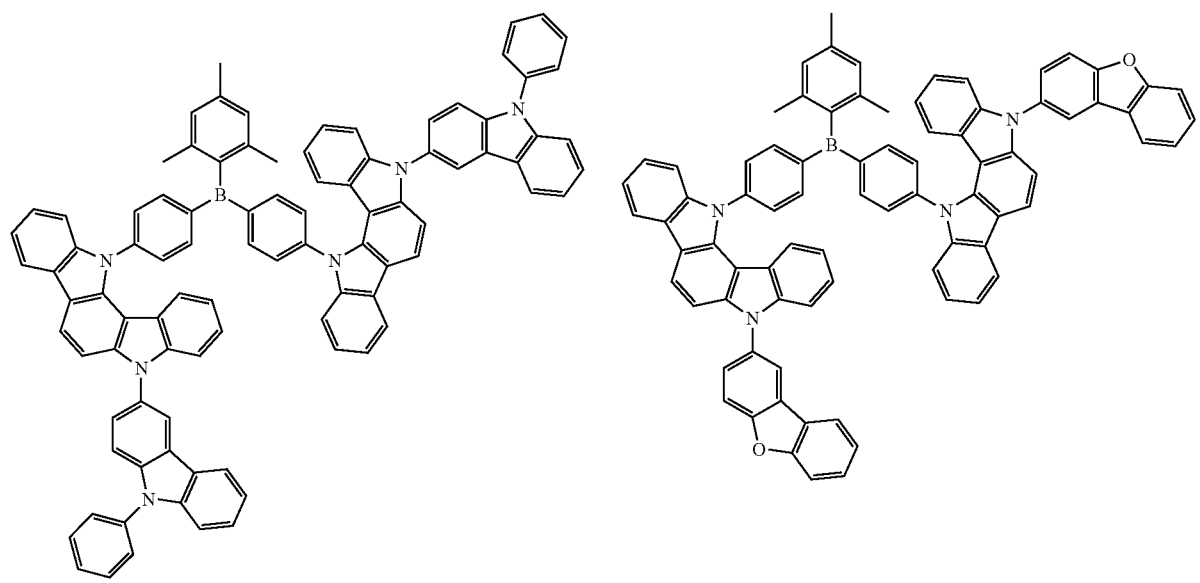
B5
B6
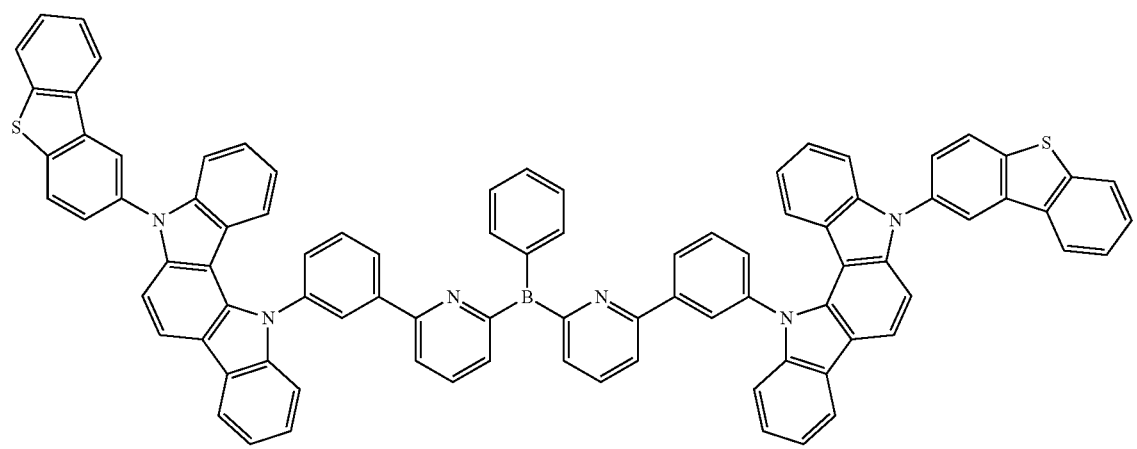
B7

-continued
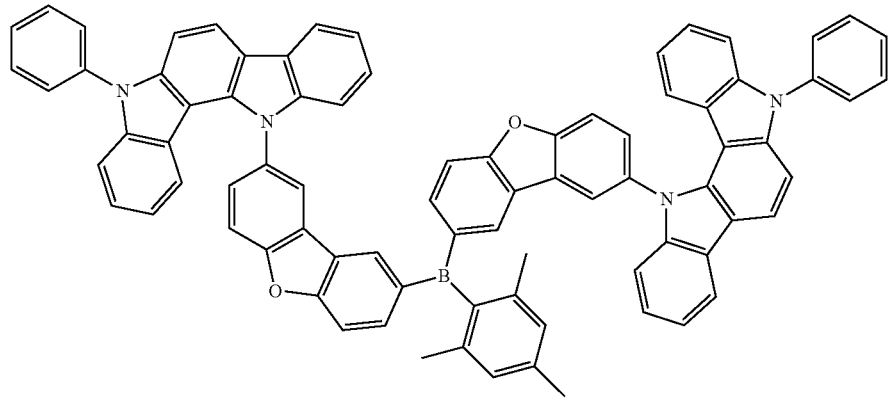
B8
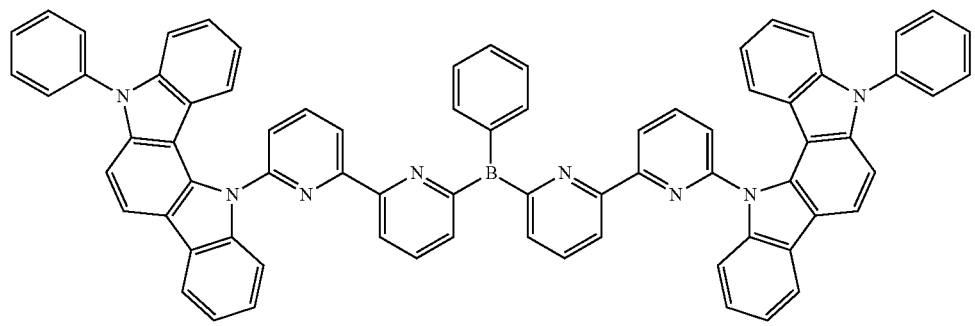
B9
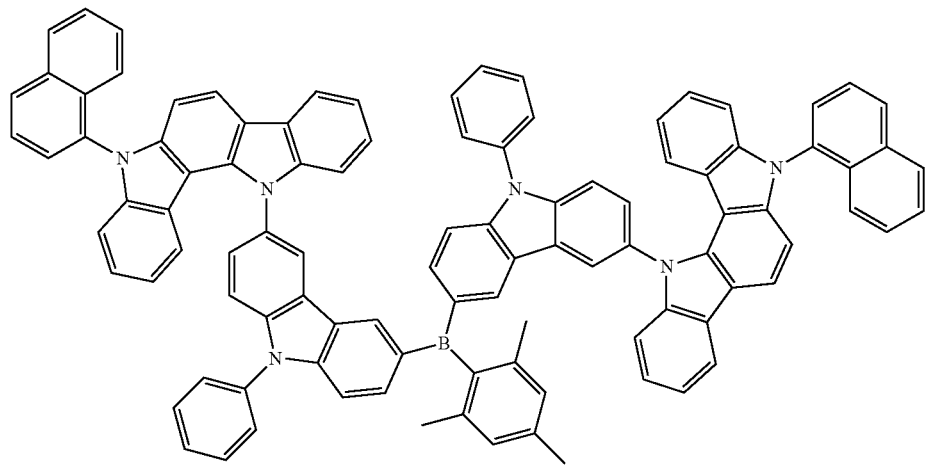
B10
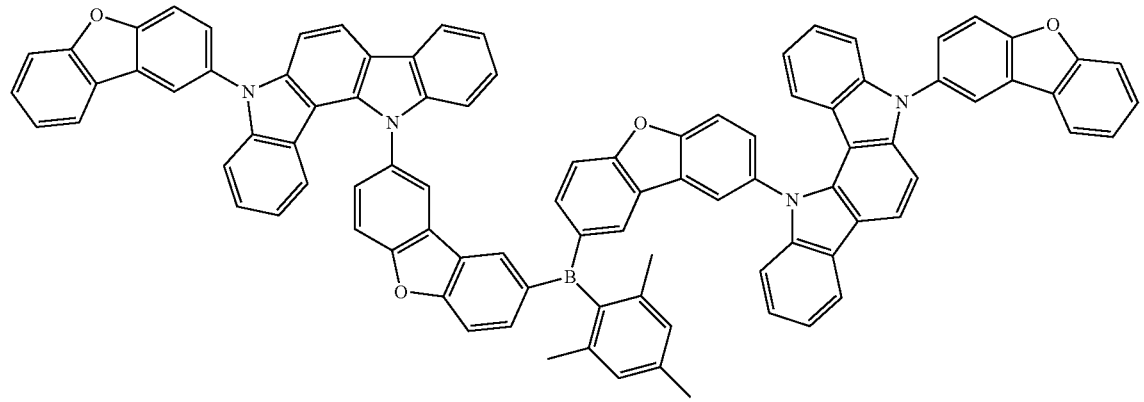
B11

-continued
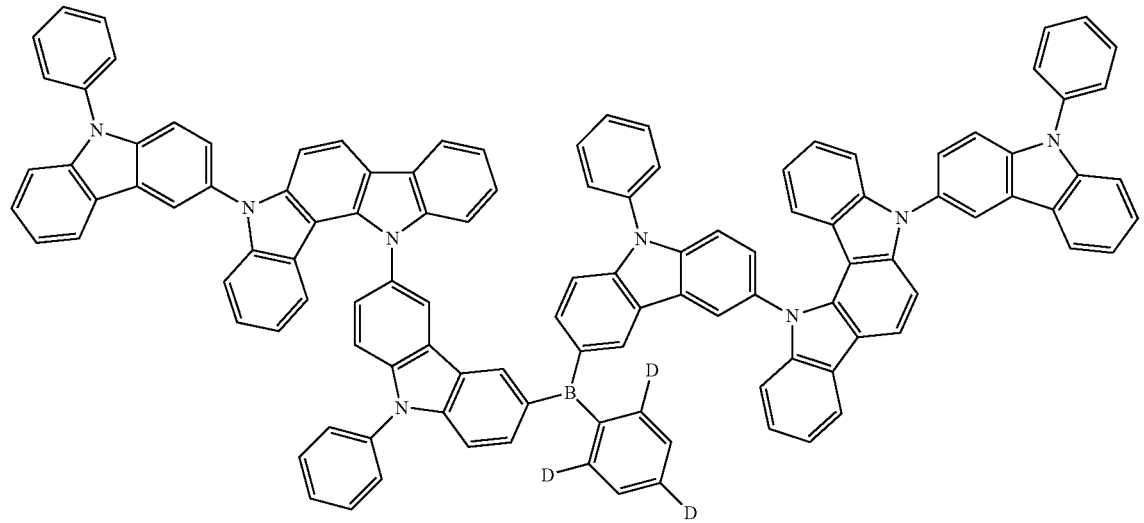
B12
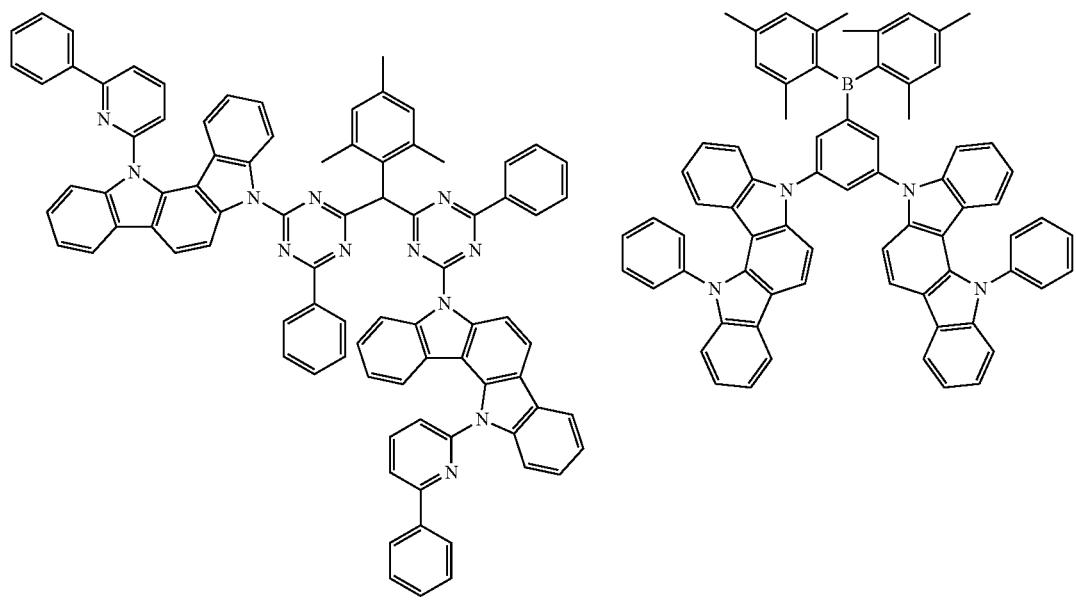
B13
B14
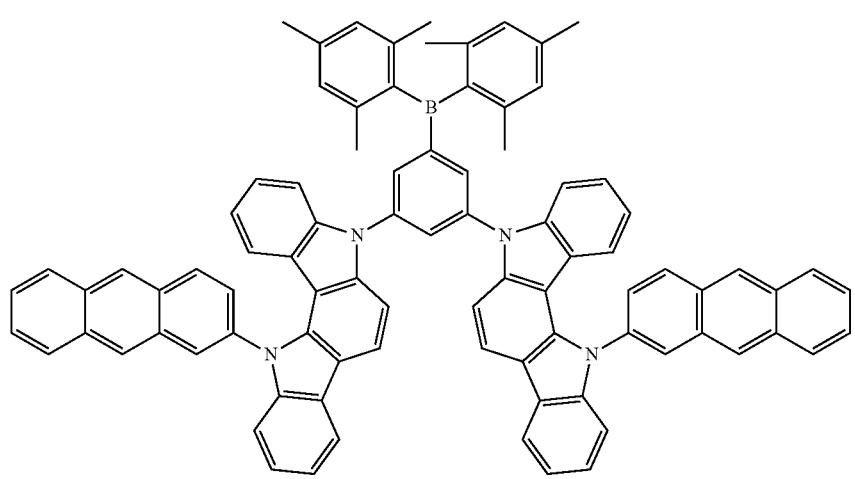
B15

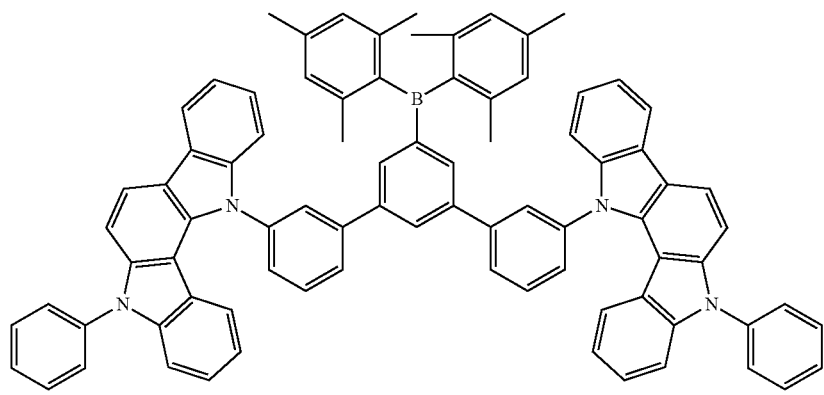
B16
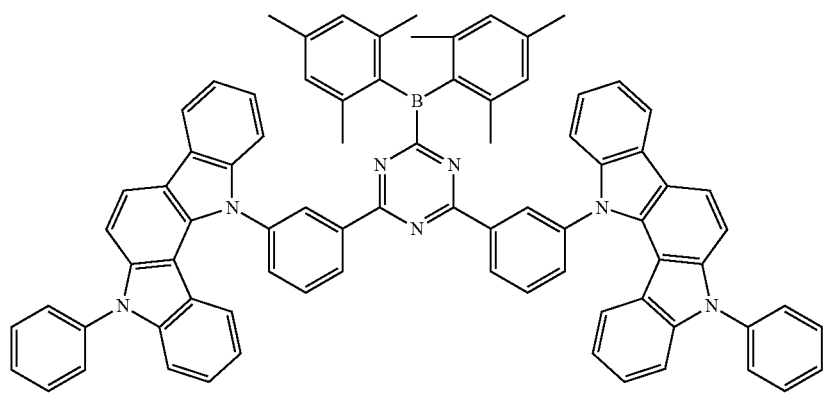
B17
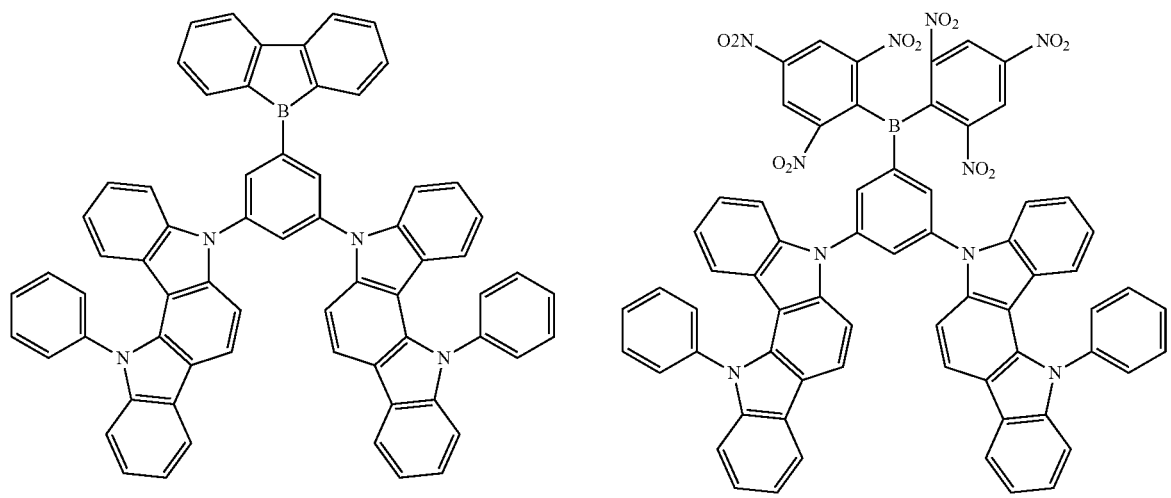
B18
B19

-continued
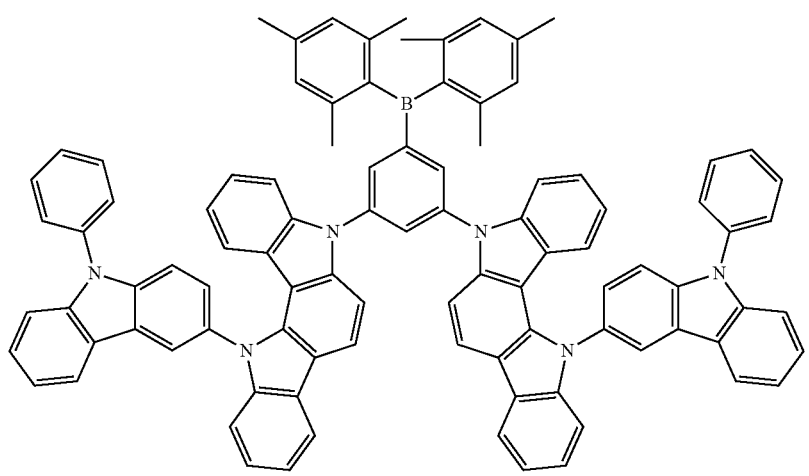
B20
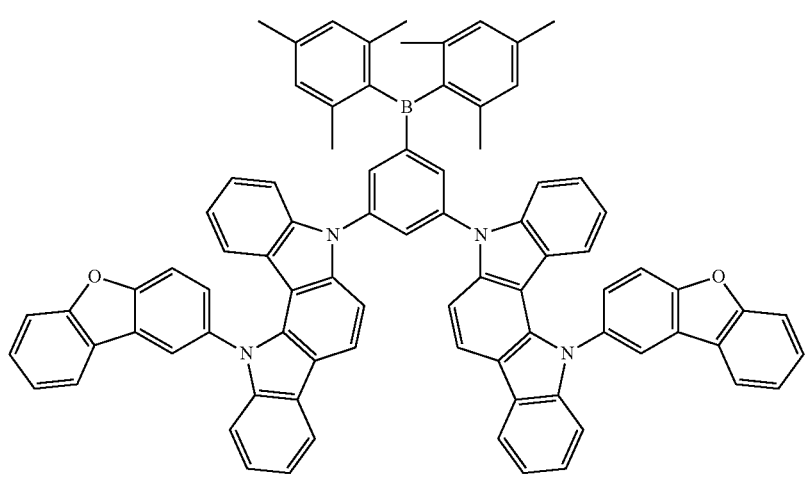
B21
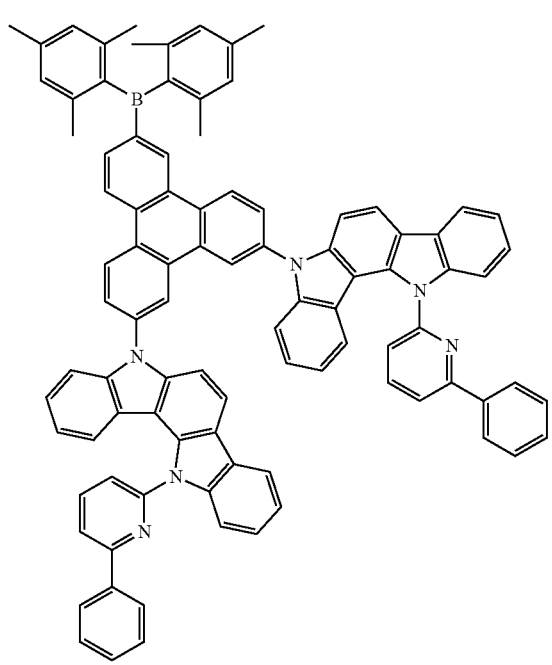
B22

-continued
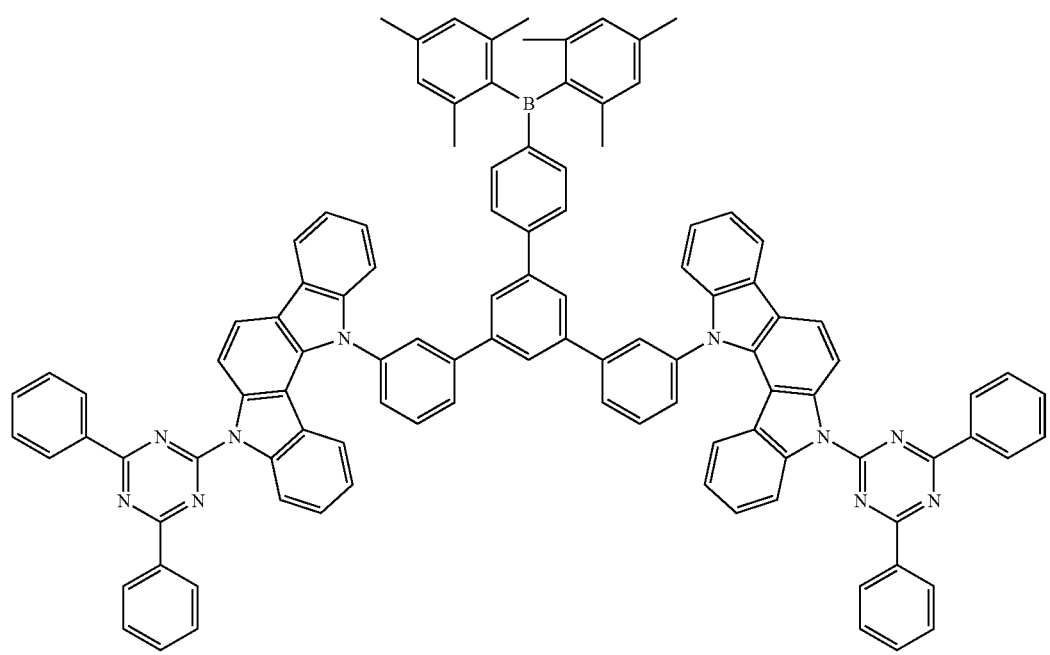
B23
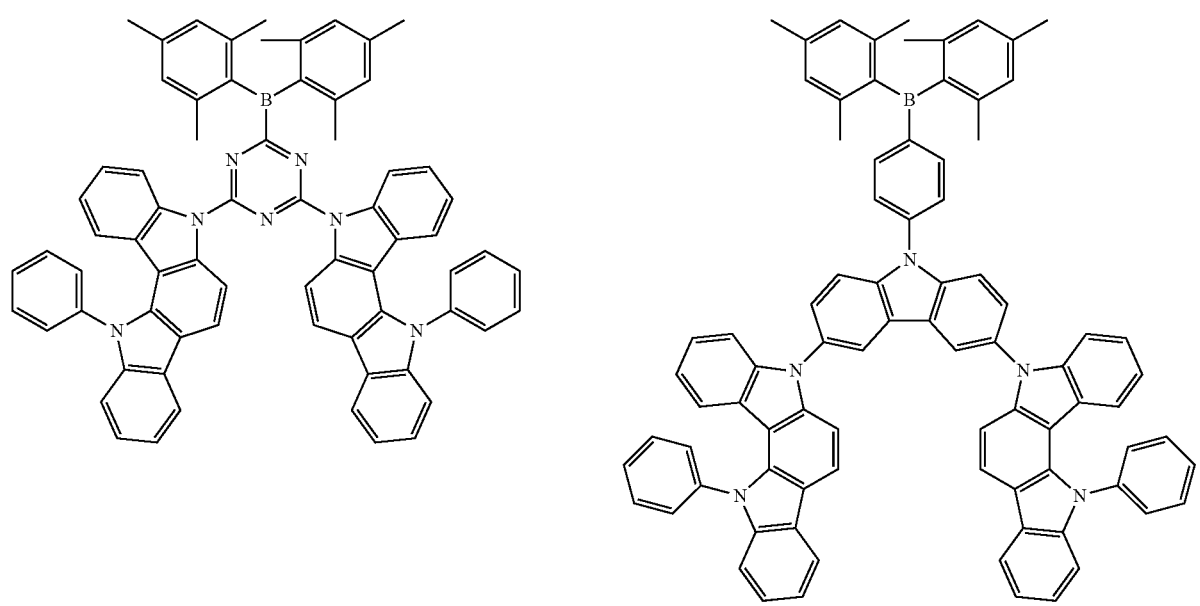
B24
B25

B26
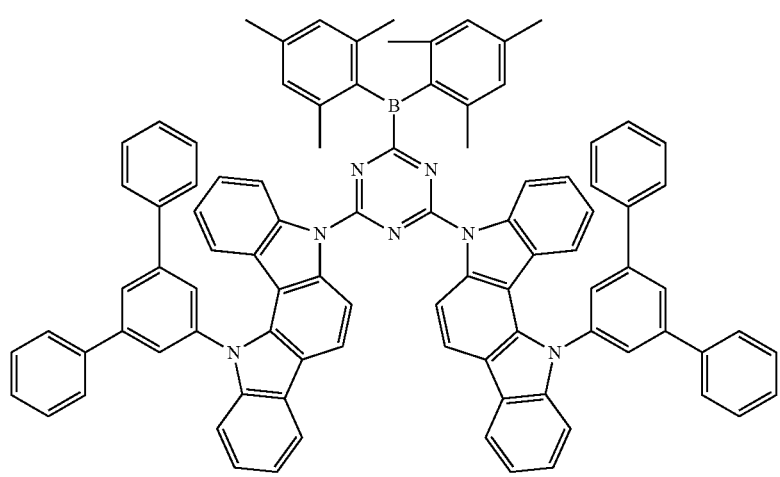
B27
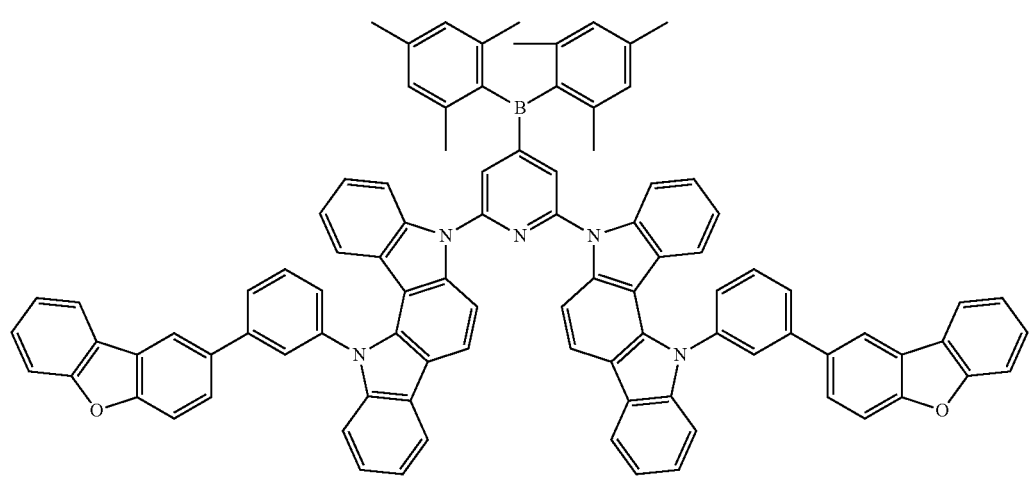
B28
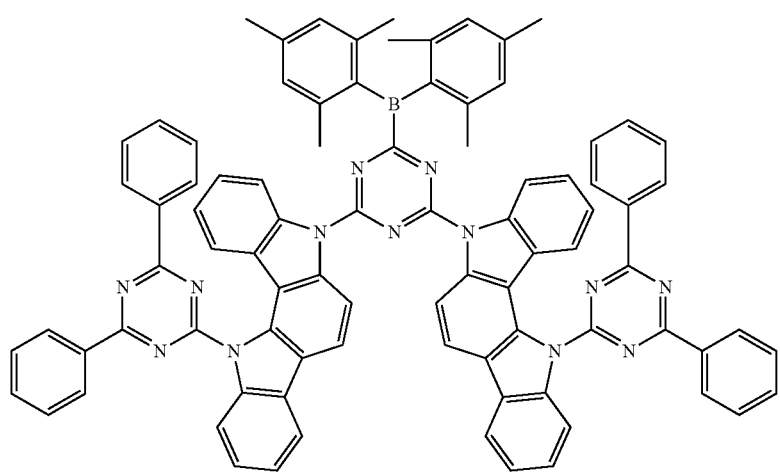

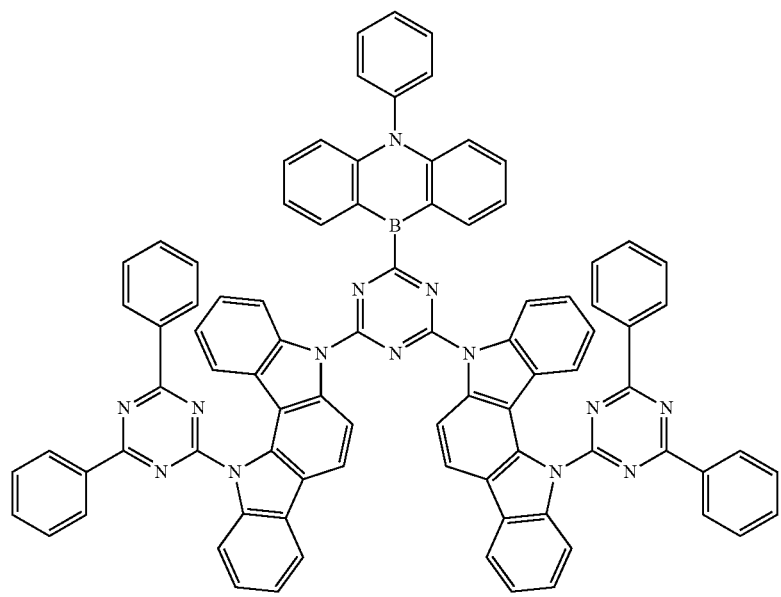
B29
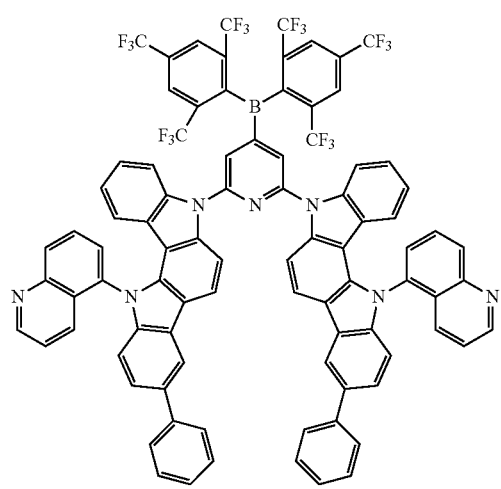
B30
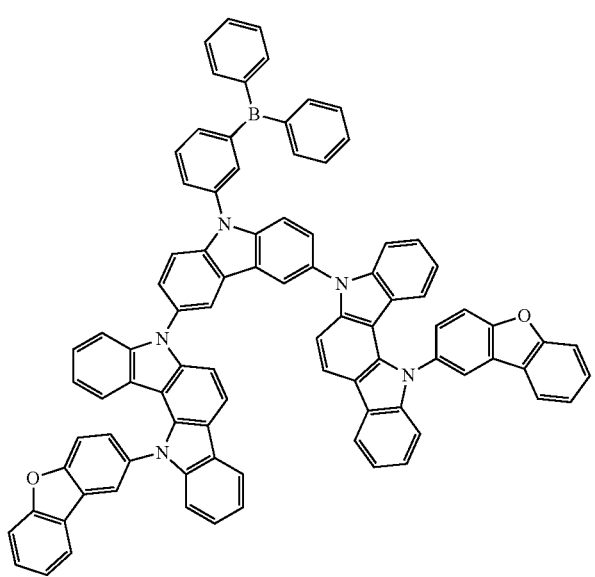
B31

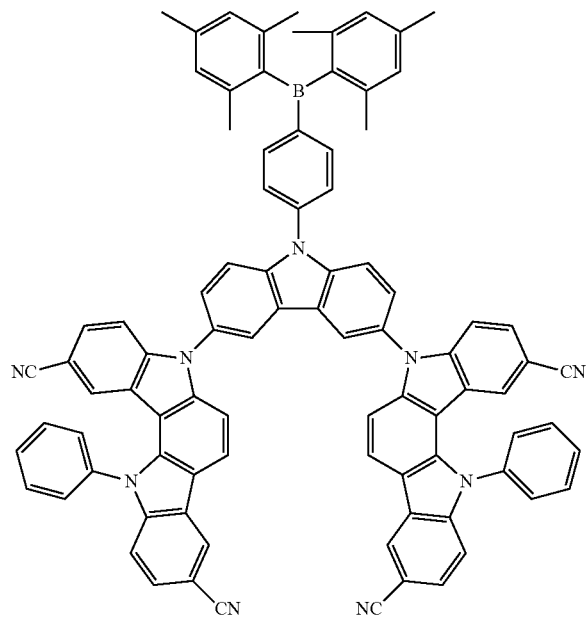
B32
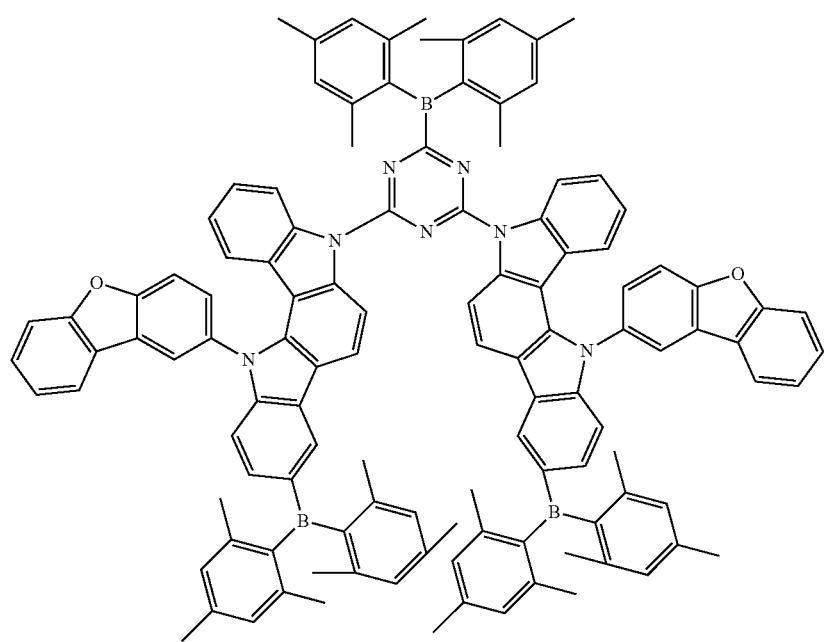
B33

-continued
B34
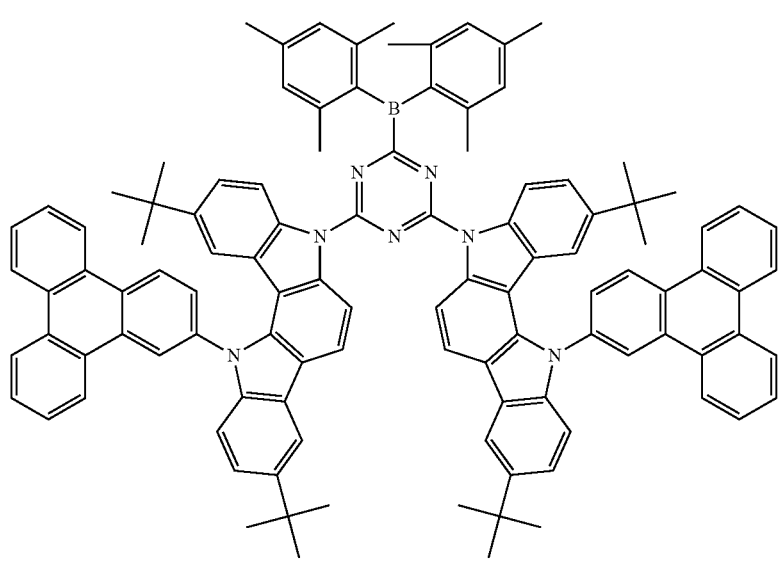
B35
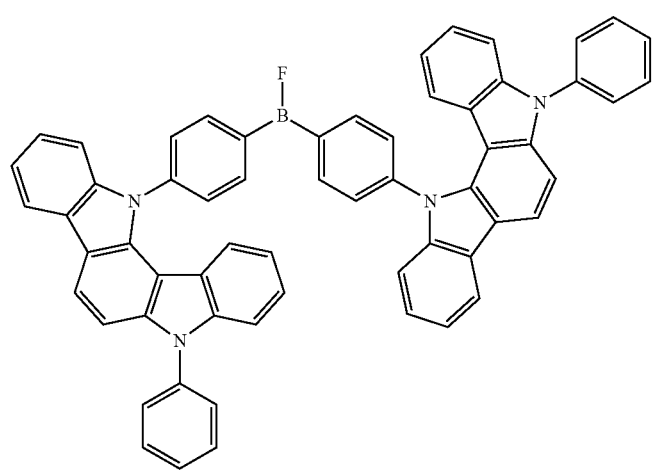
B36
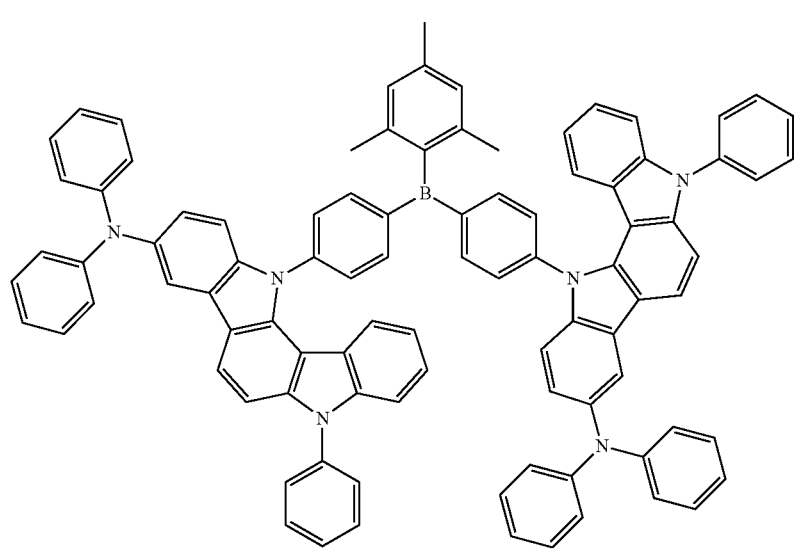

-continued
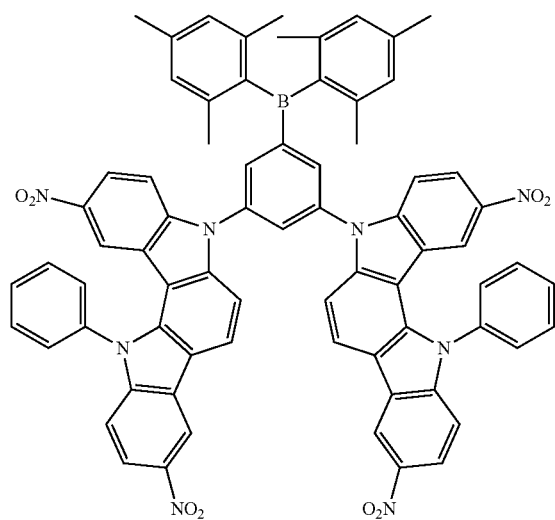
B37
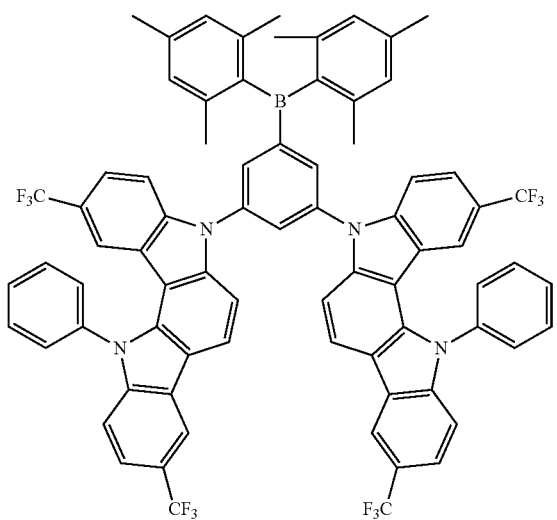
B38
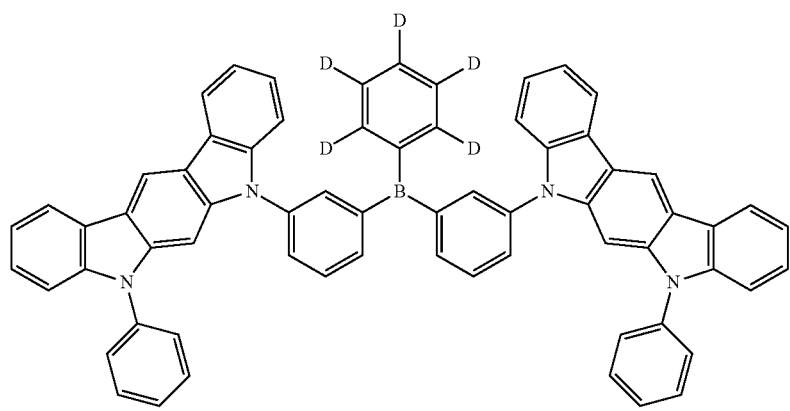
B39
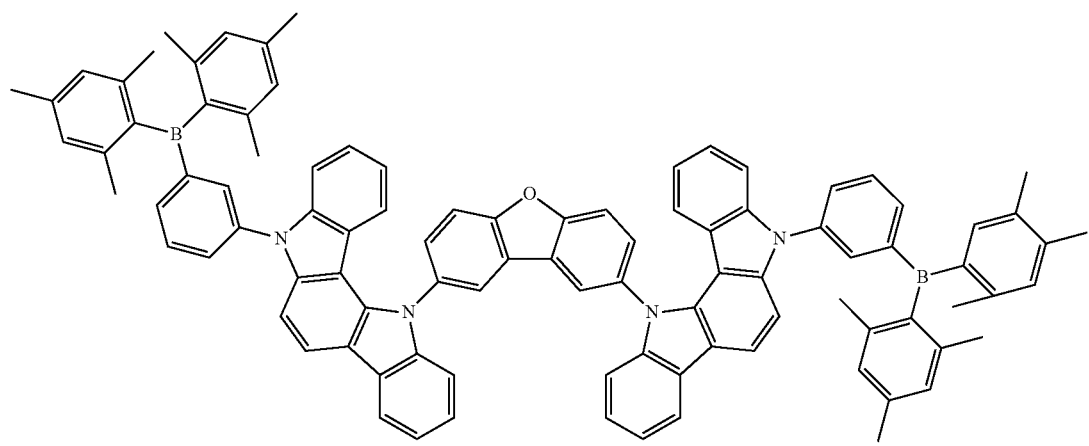
B40

B41
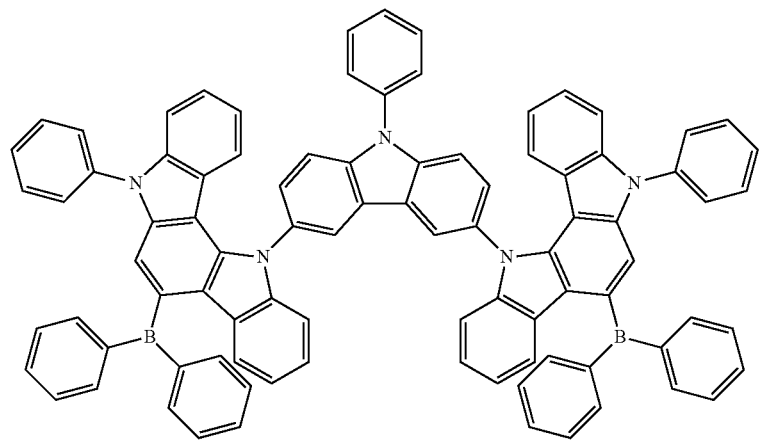
B42
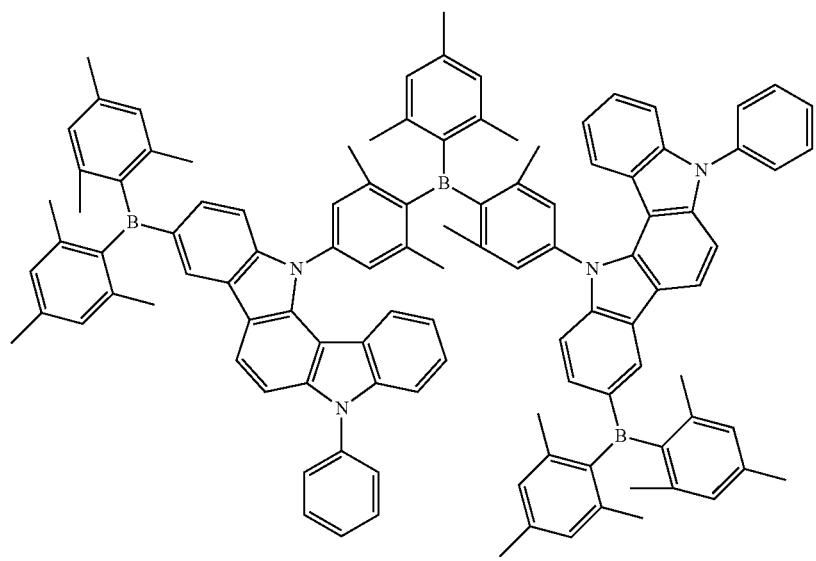
B43
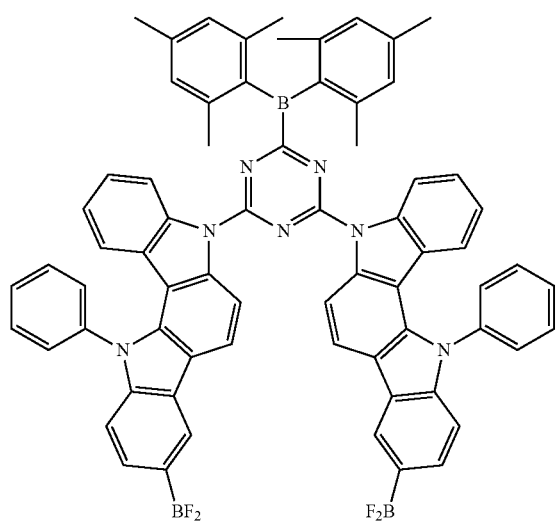

B44
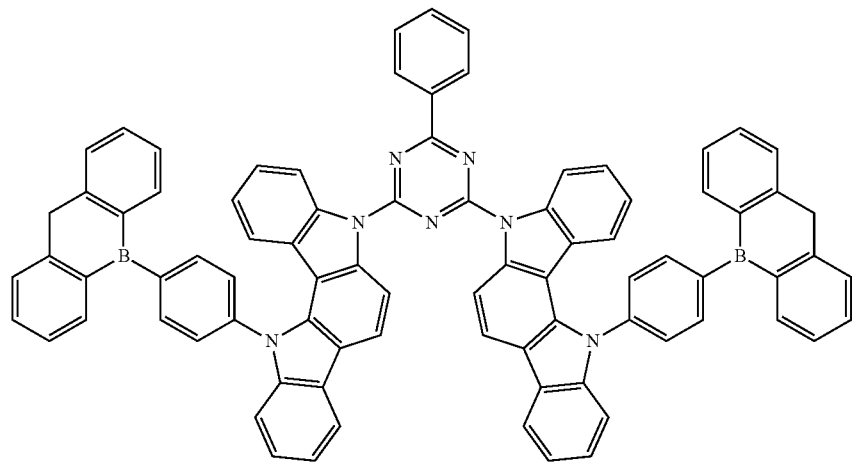
C1
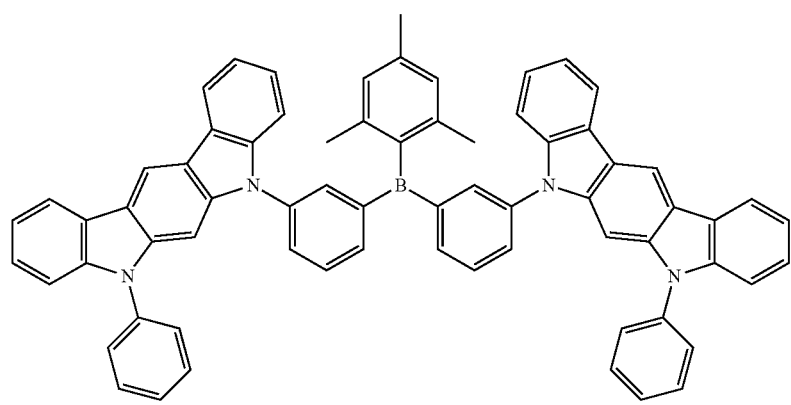
C2
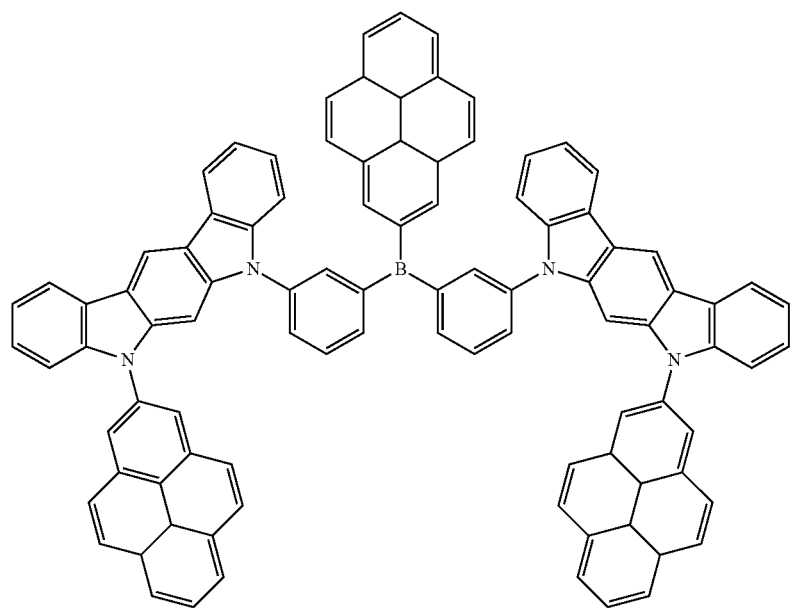

C3
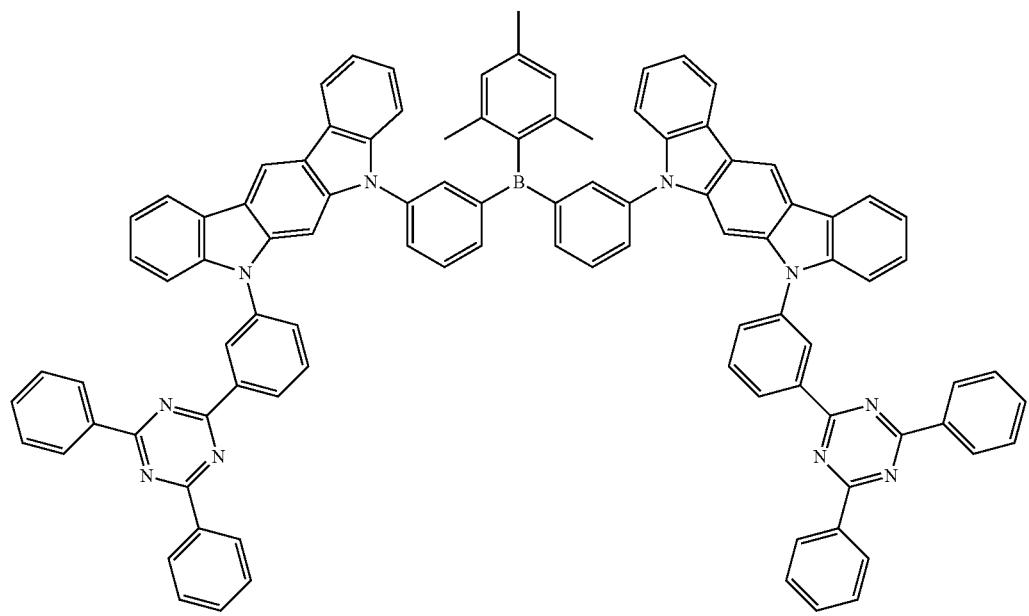
C4
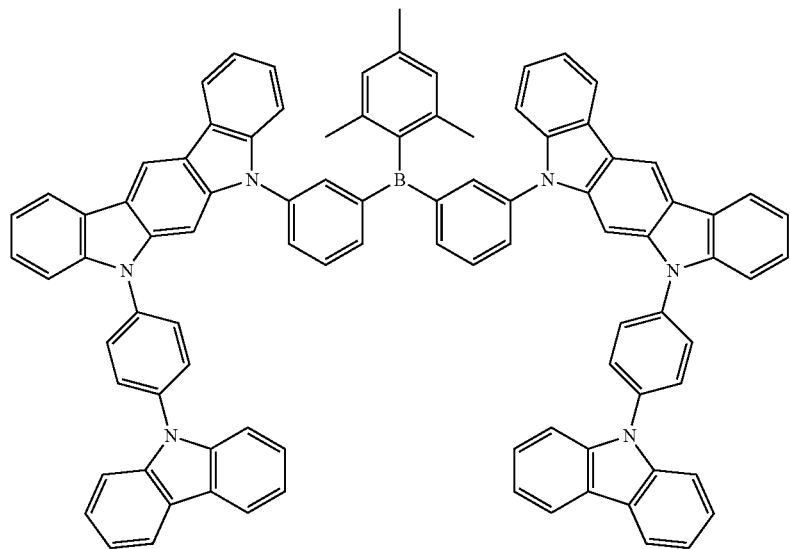

C5
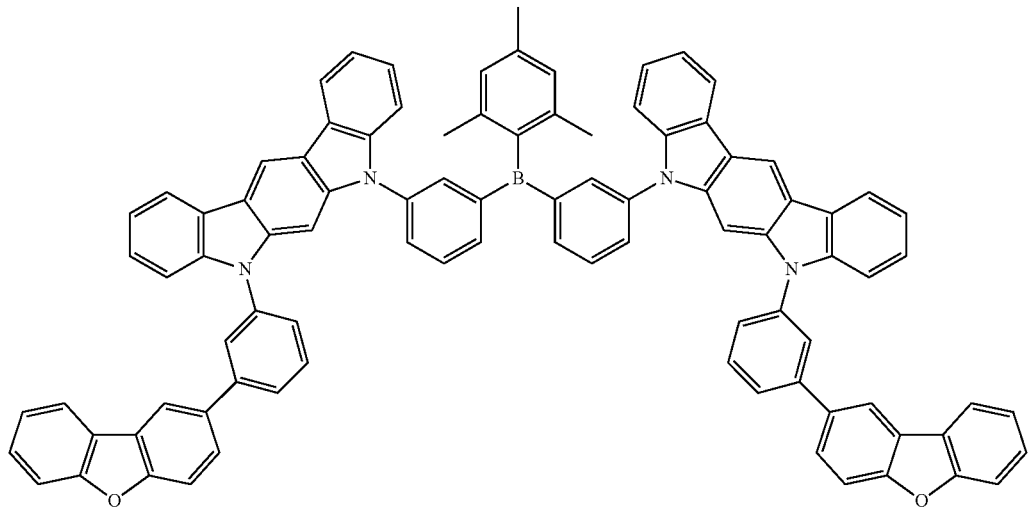
C6
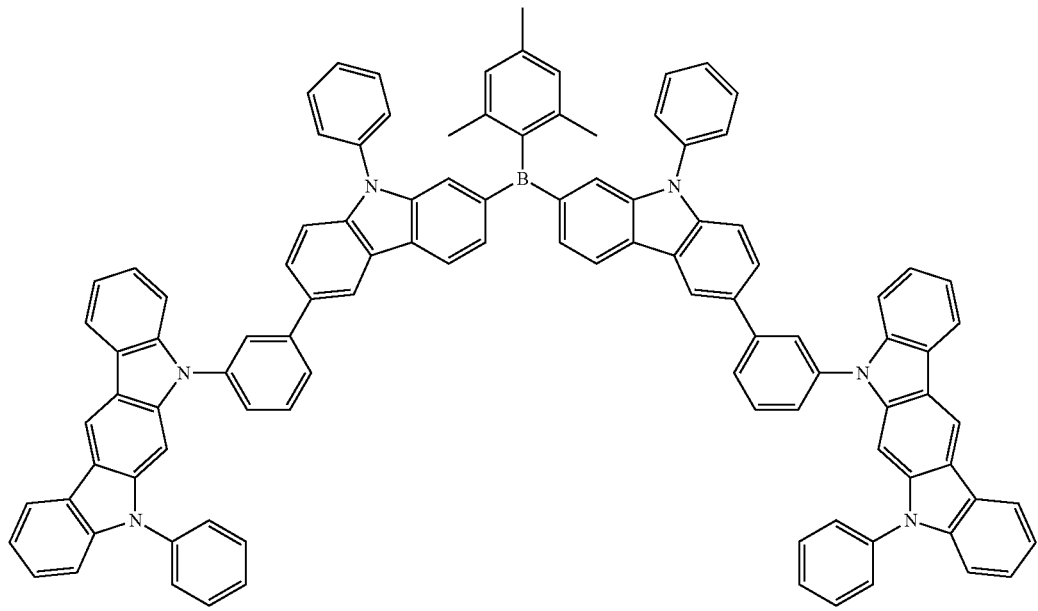
C7
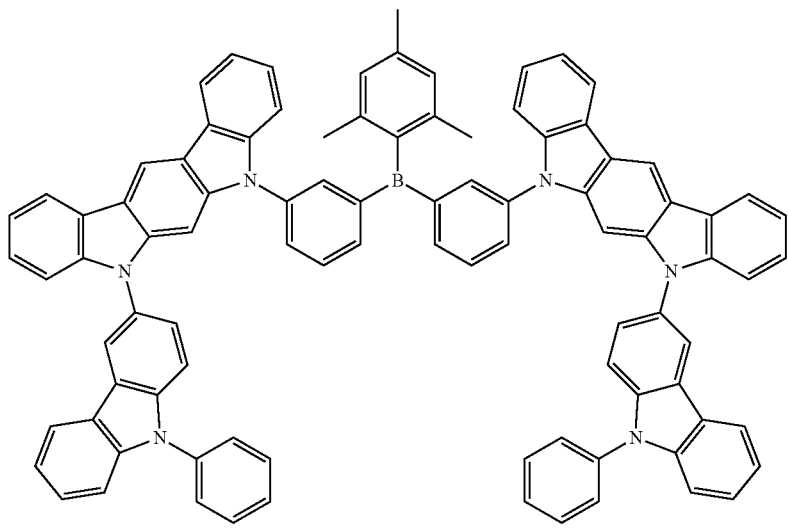

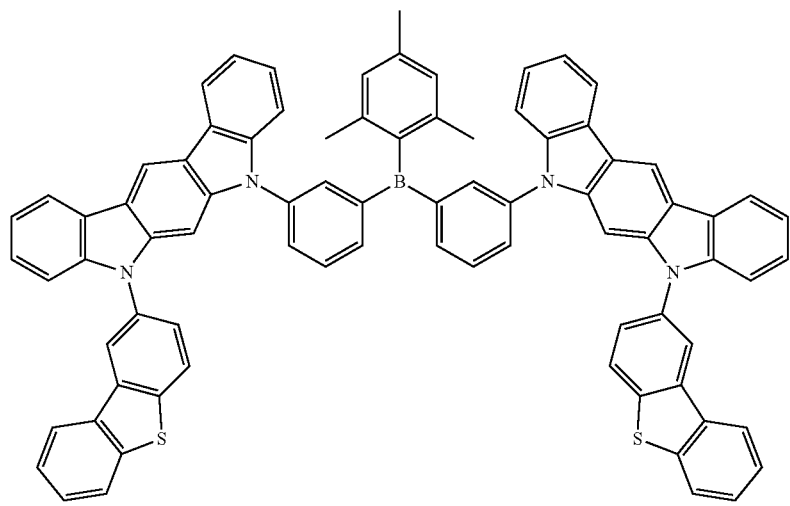
C8
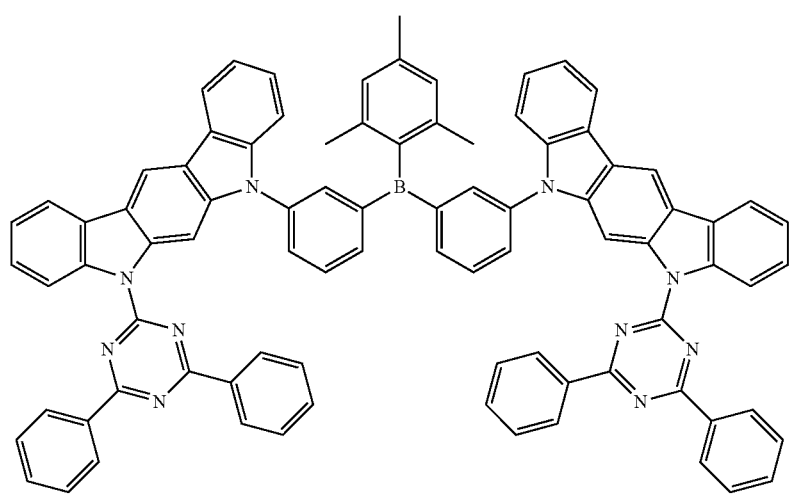
C9
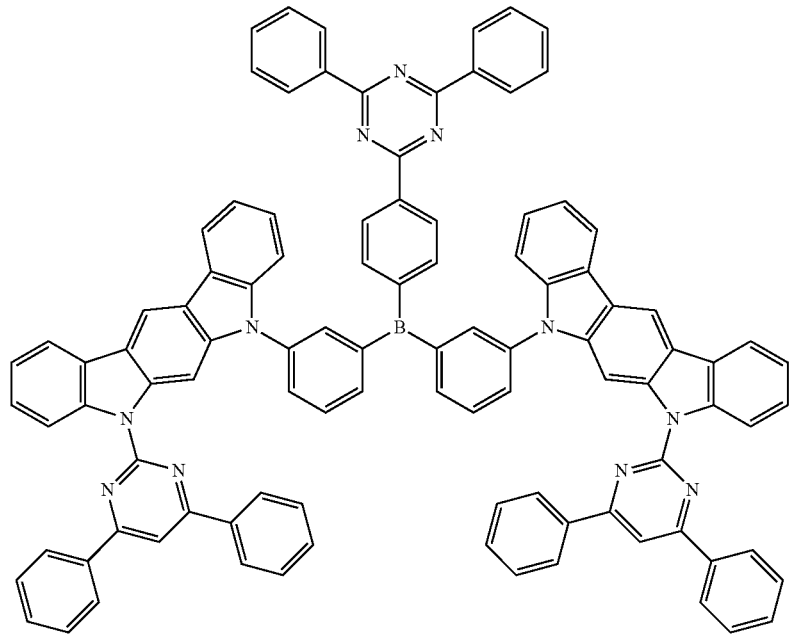
C10

C11
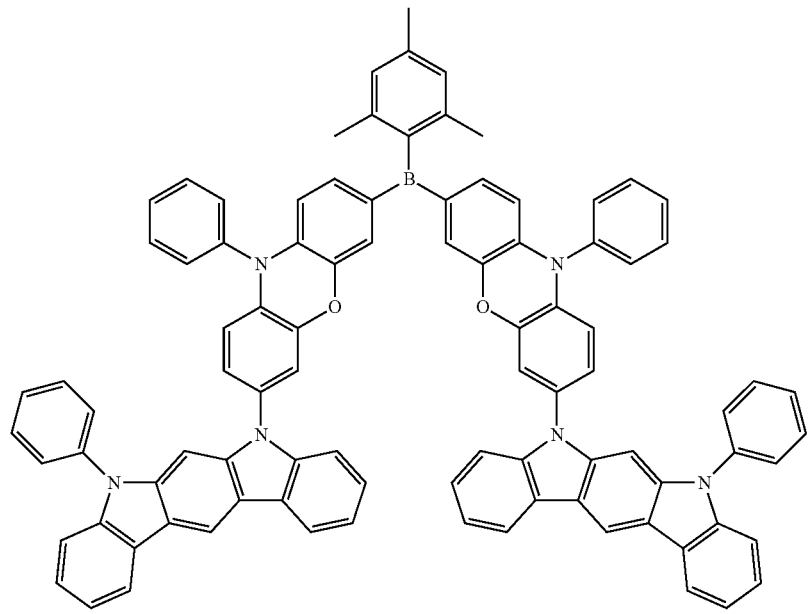
C12
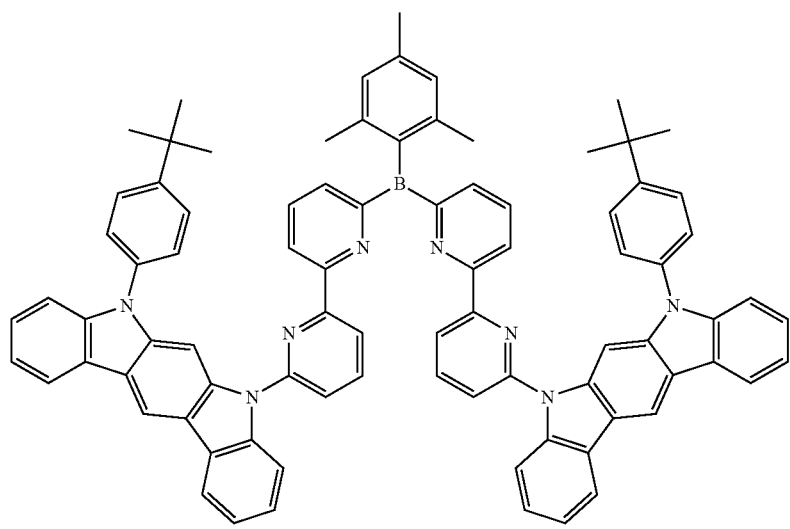
C13
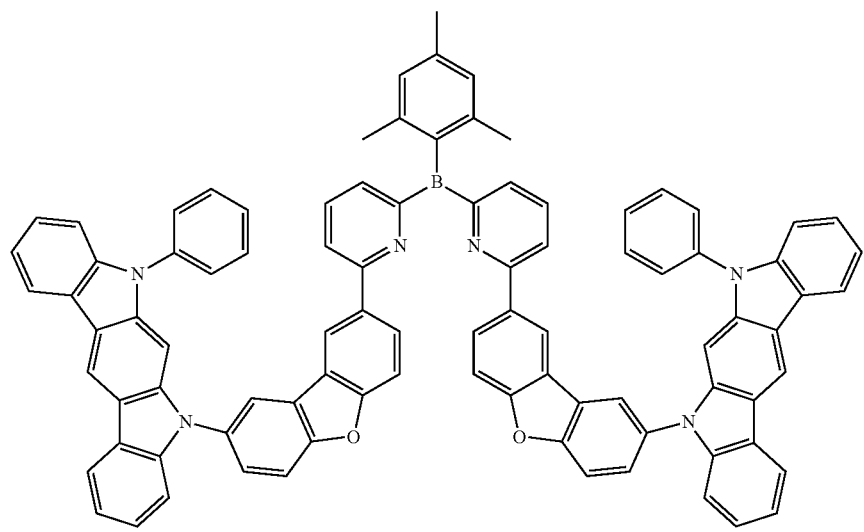

-continued
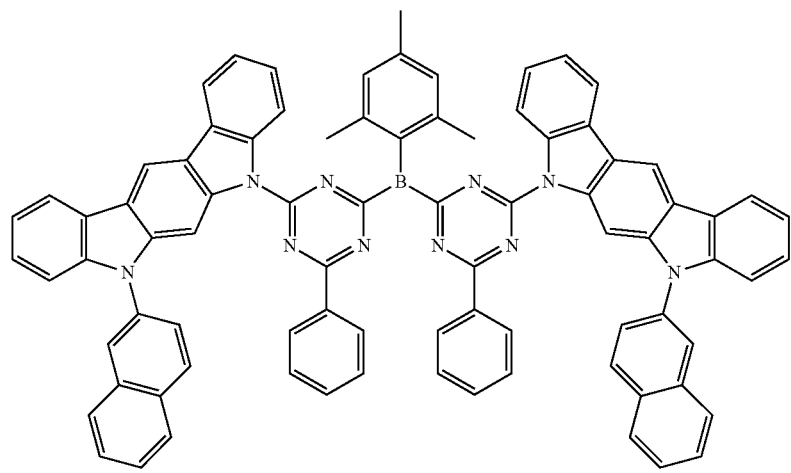
C14
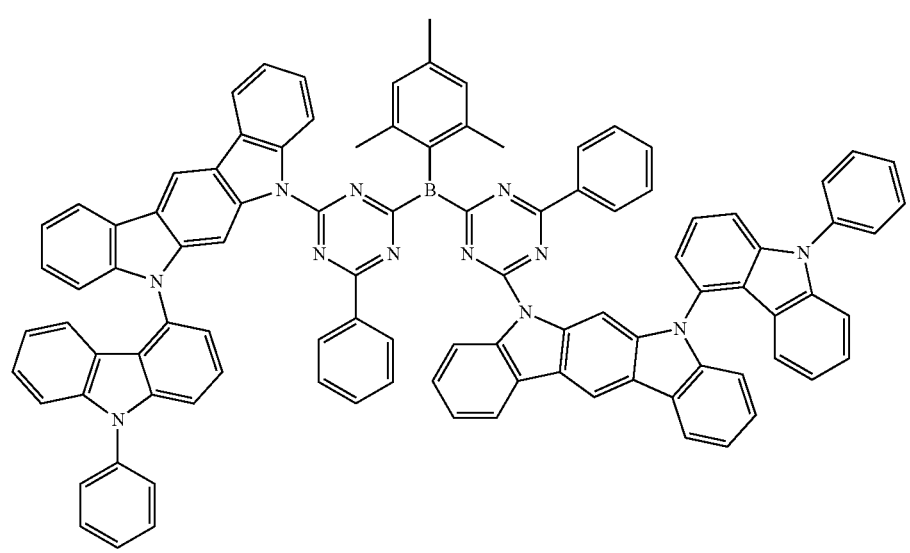
C15
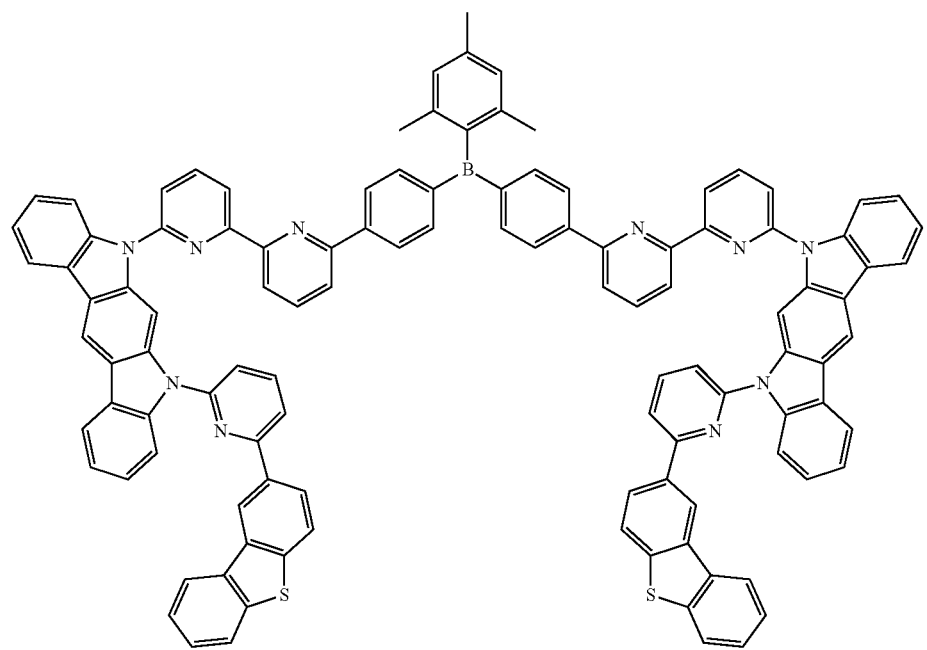
C16

-continued
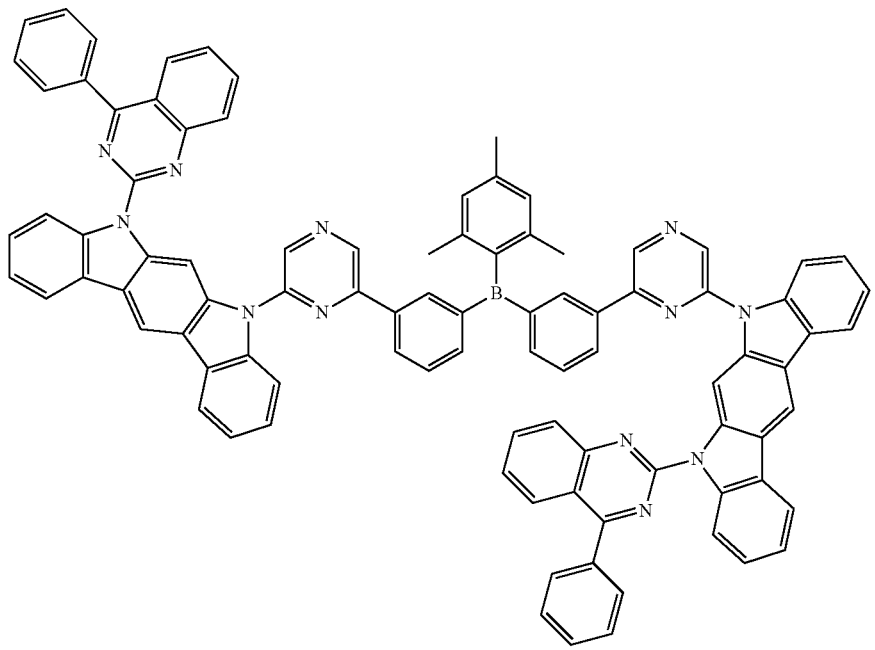
C17
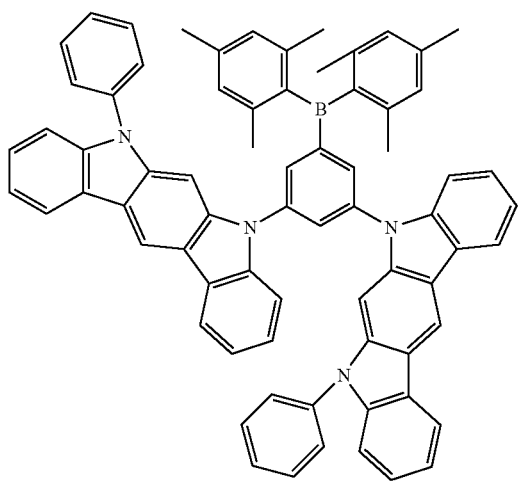
C18
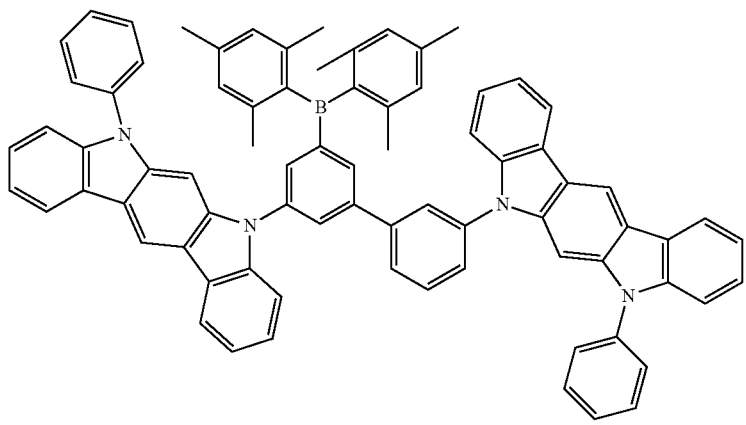
C19

-continued
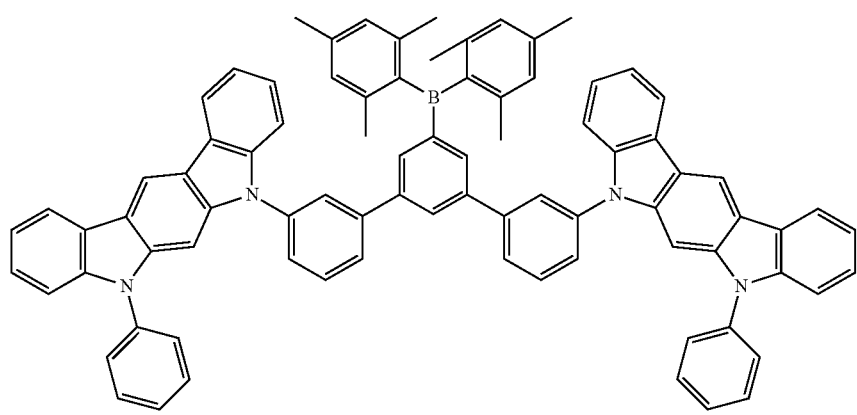
C20
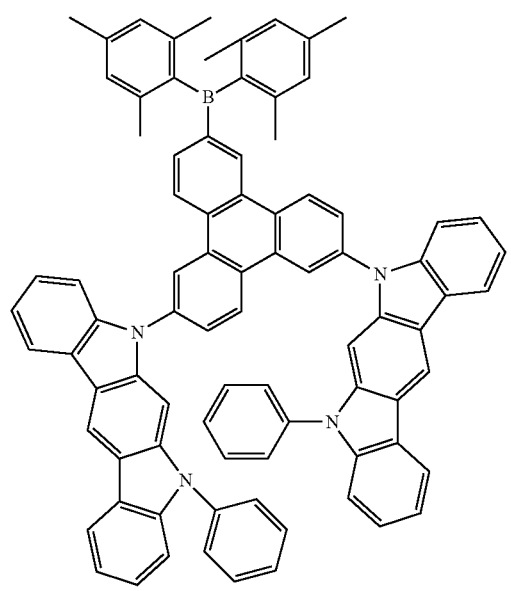
C21
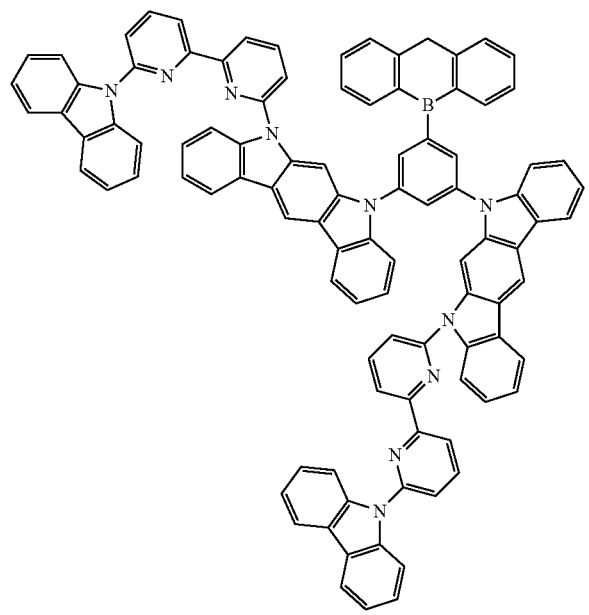
C22
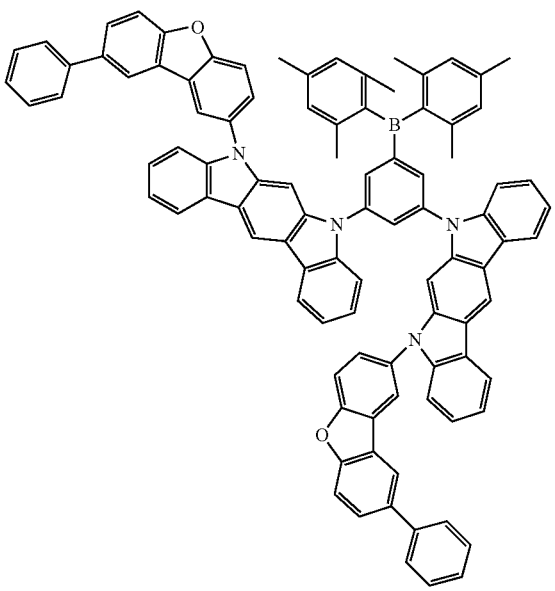
C23

C24
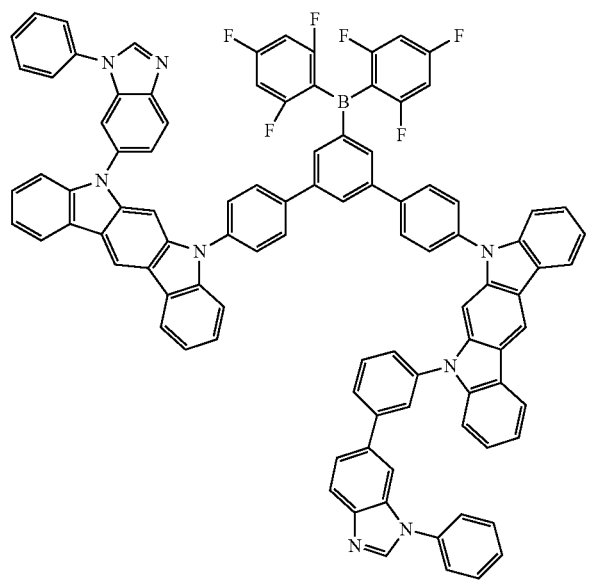
C25
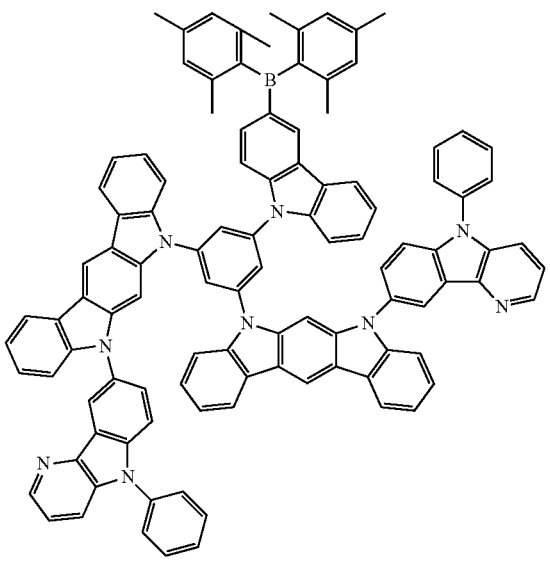
C26
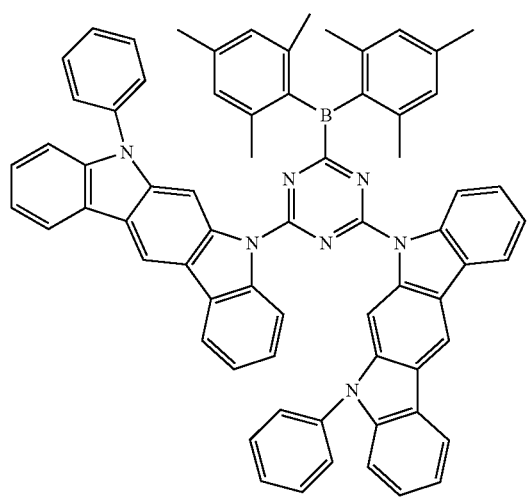
C27
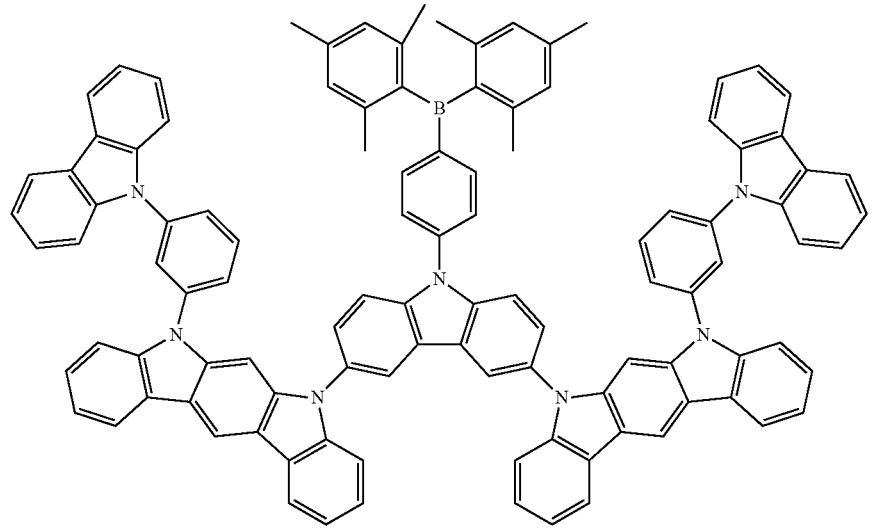

-continued
C28
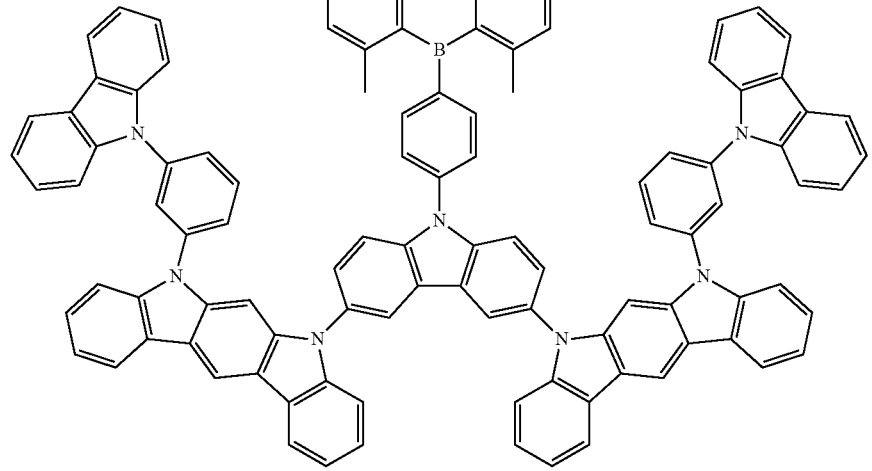
C29
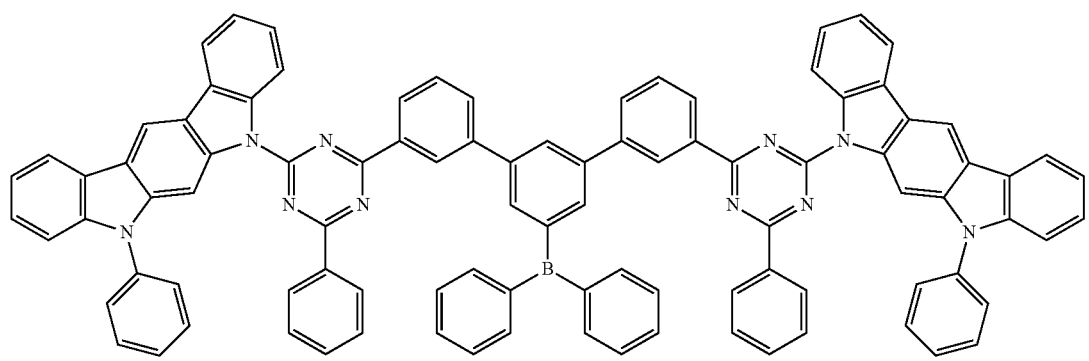
C30
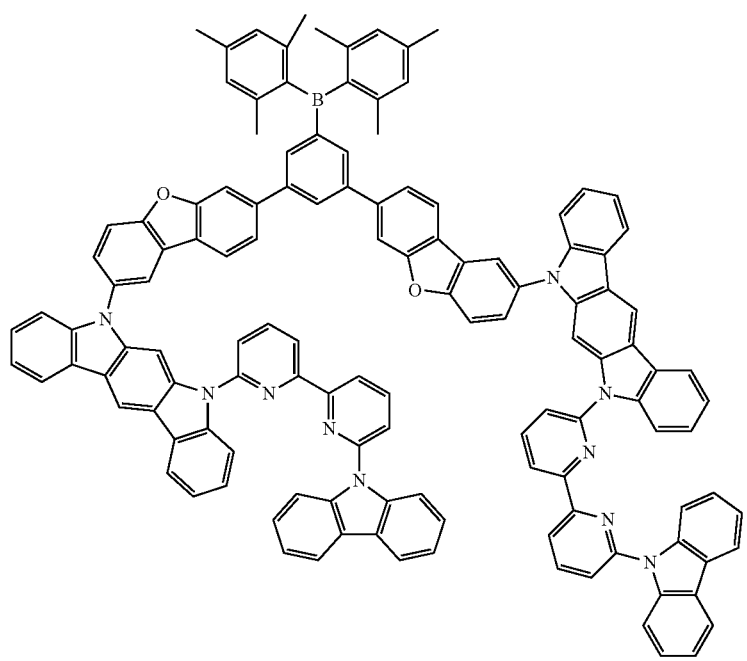

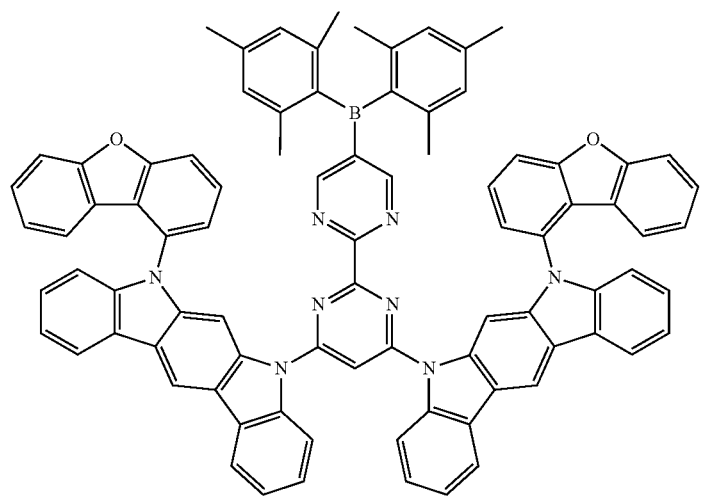
C31
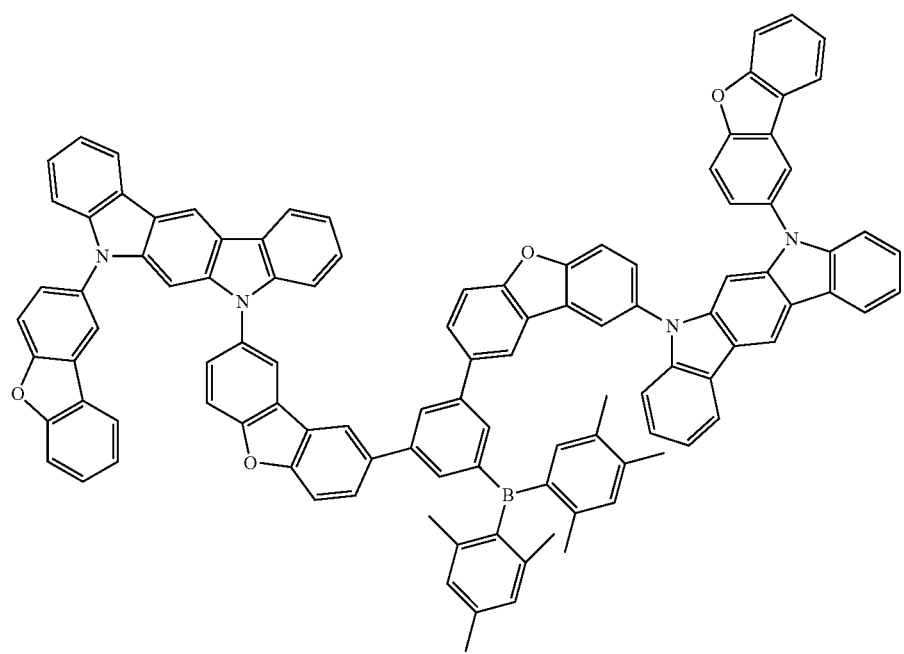
C32

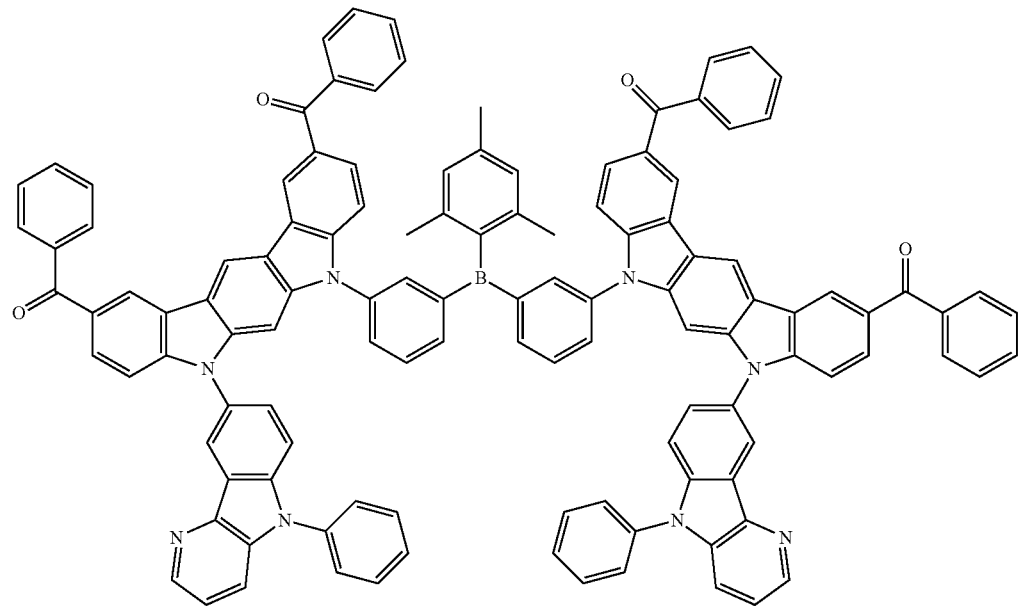
C33
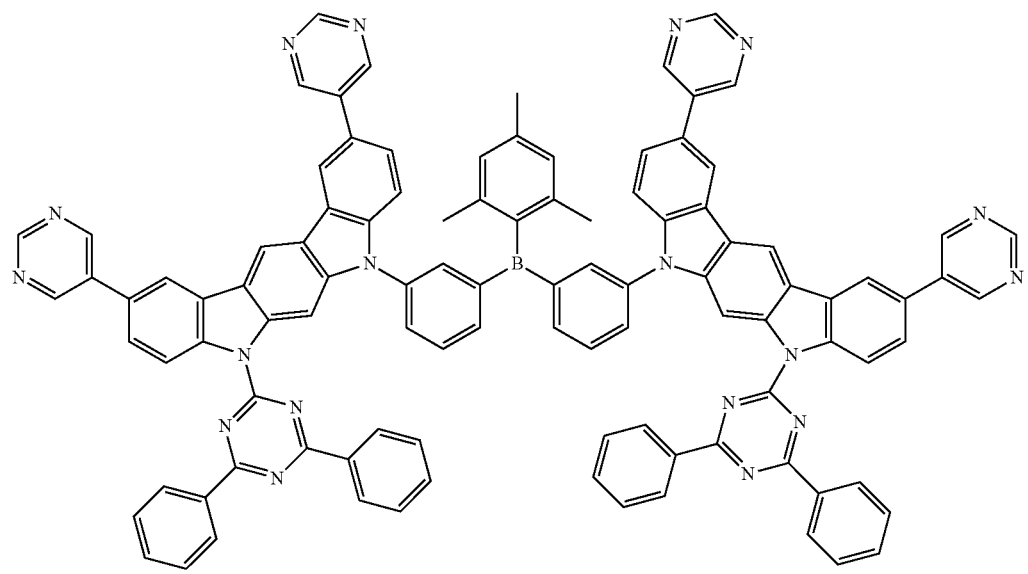
C34

C35
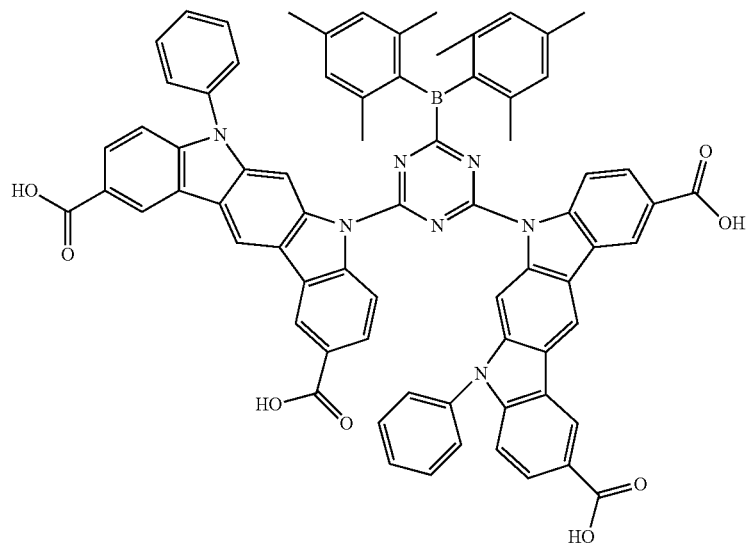
C36
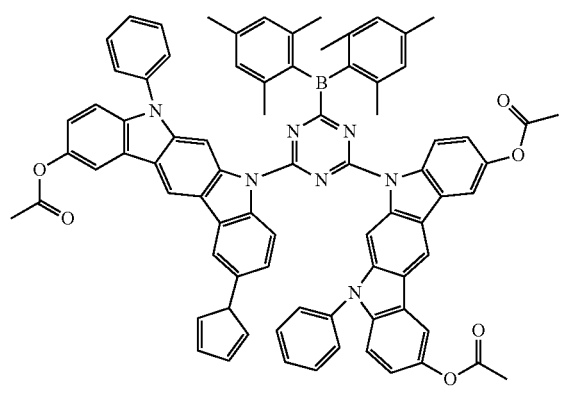
C37
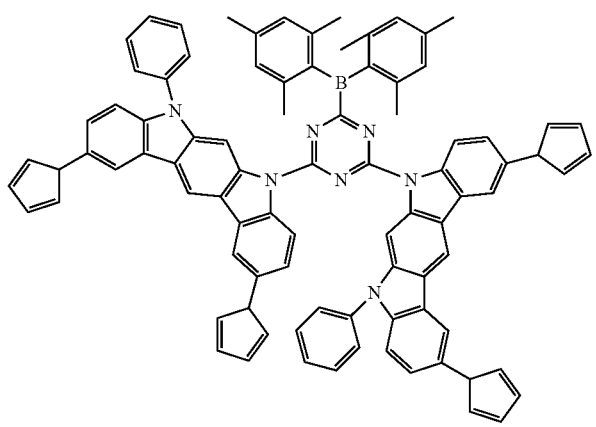
C38
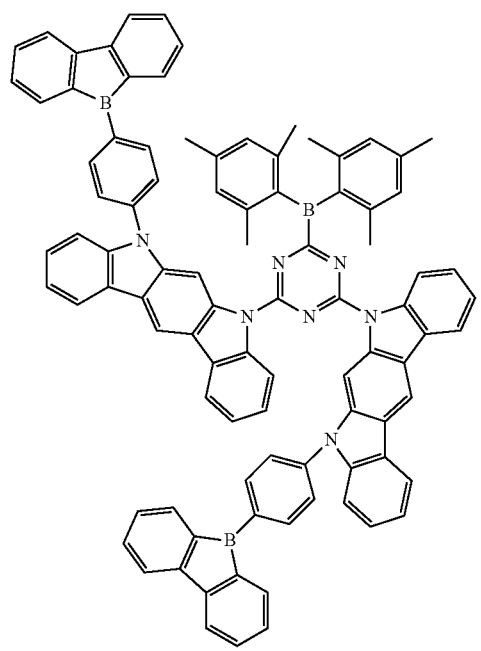

C39
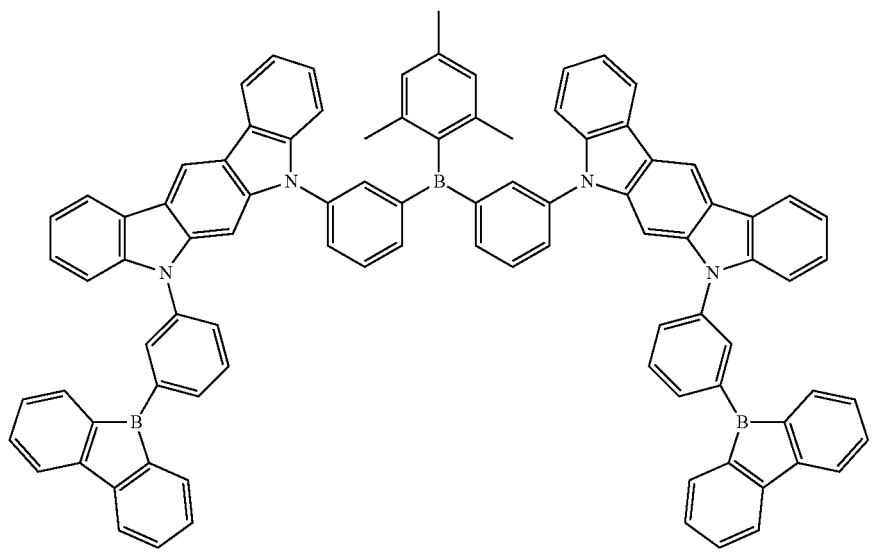
C40
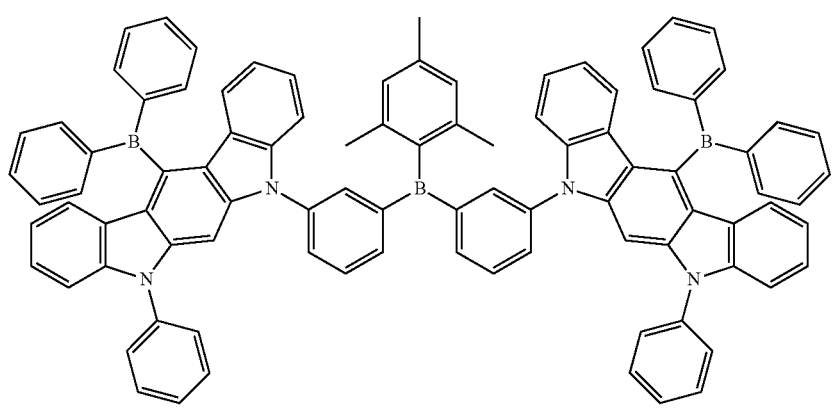
C41
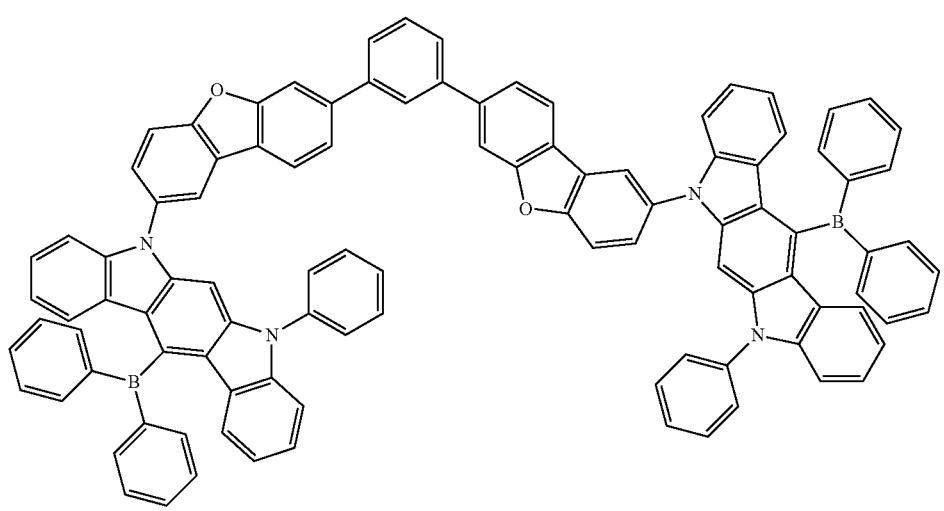

-continued
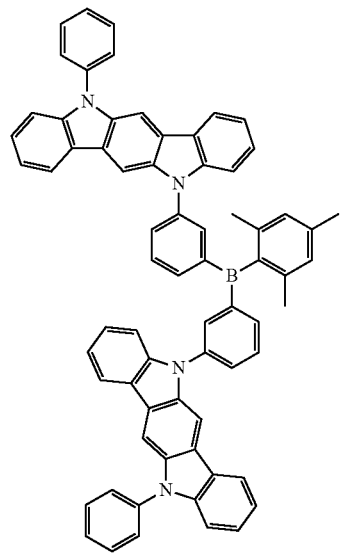
D1
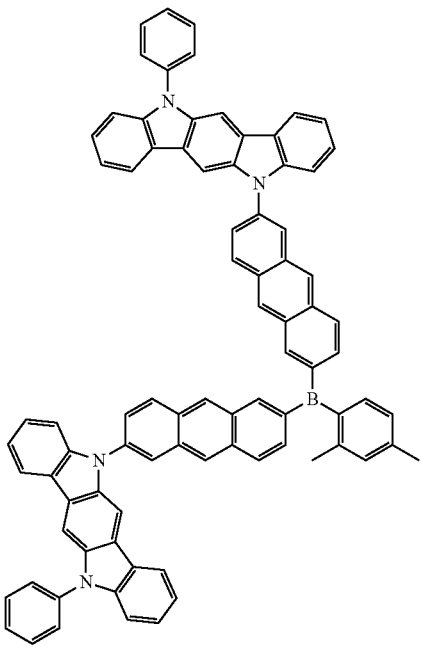
D2
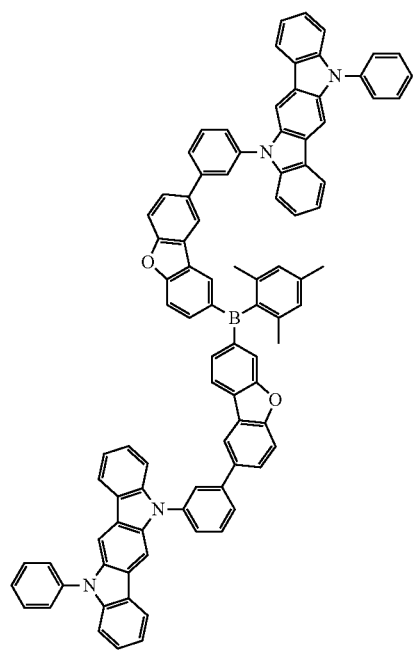
D3
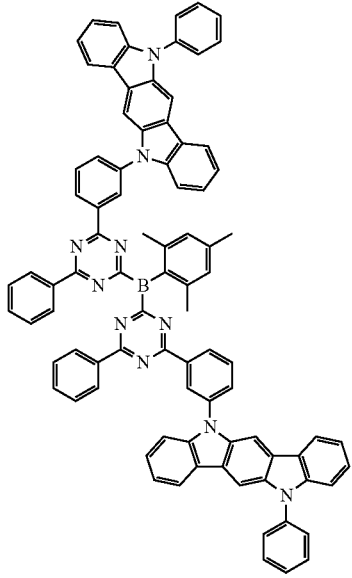
D4

-continued
D5
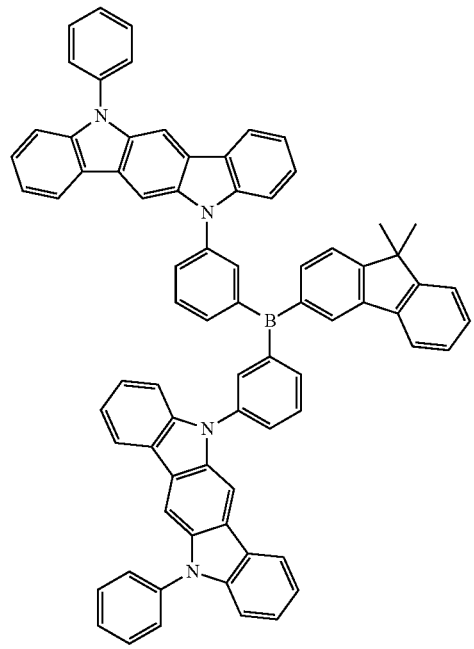
D6
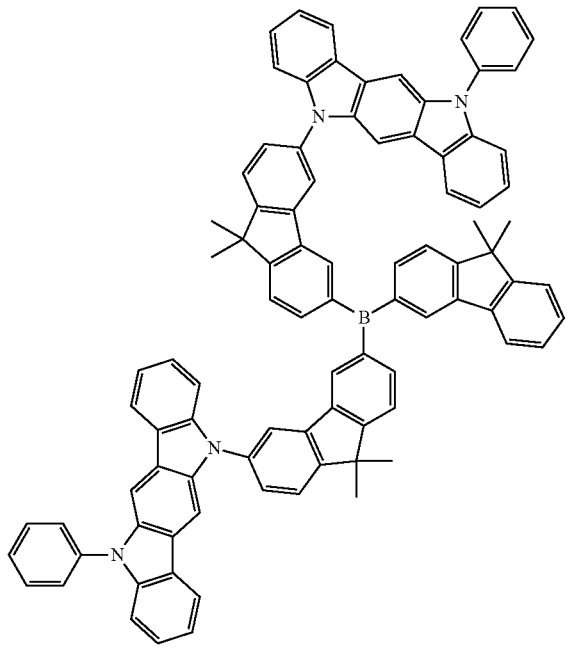
D7
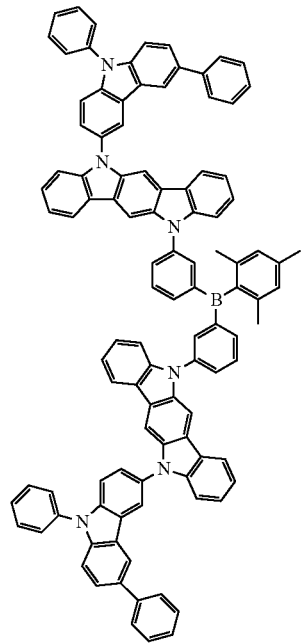
D8
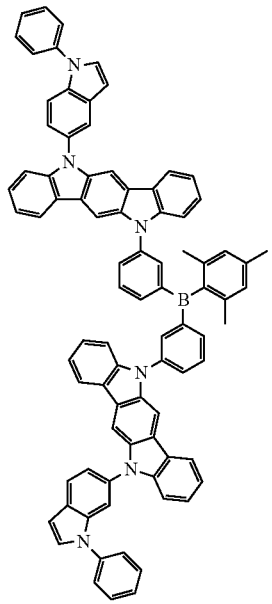

D9
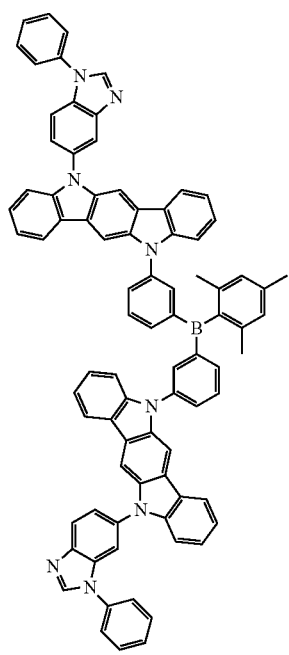
D10
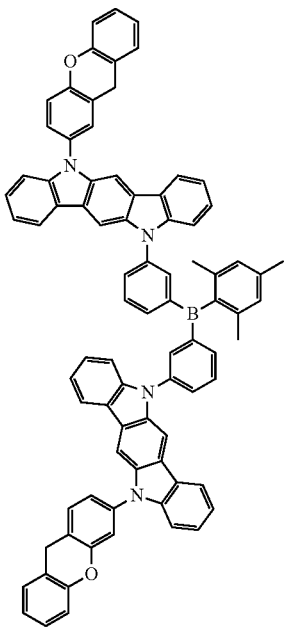
D11
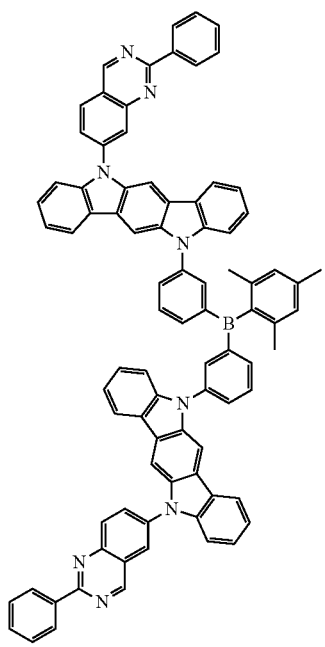
D12
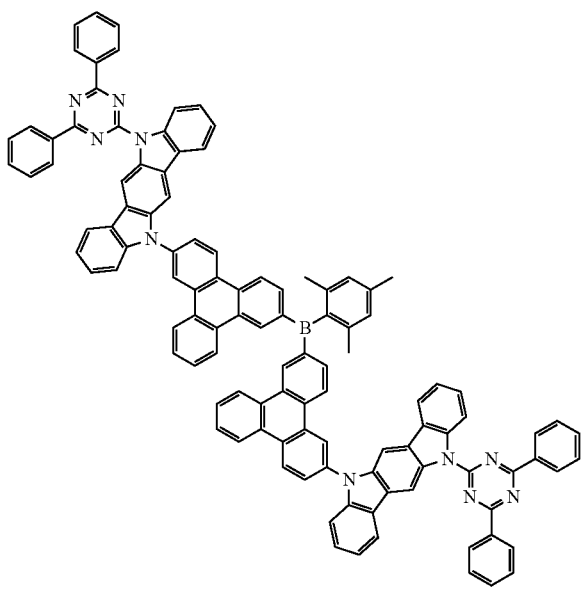

-continued
D13
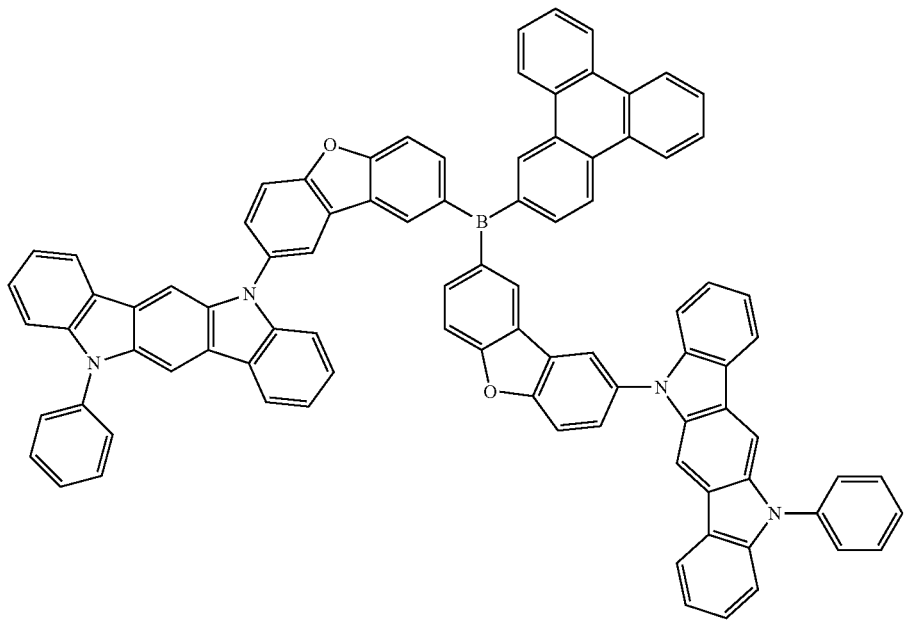
D14
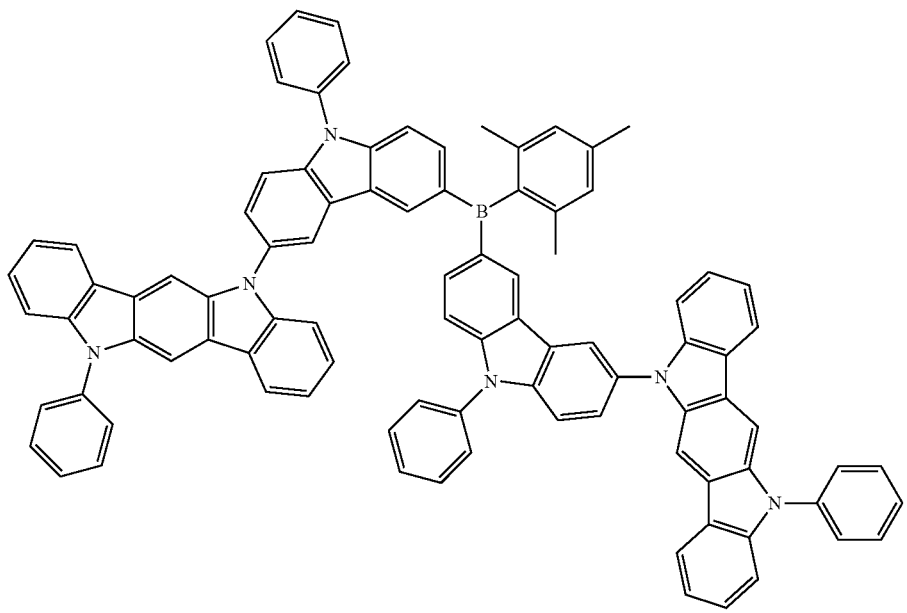

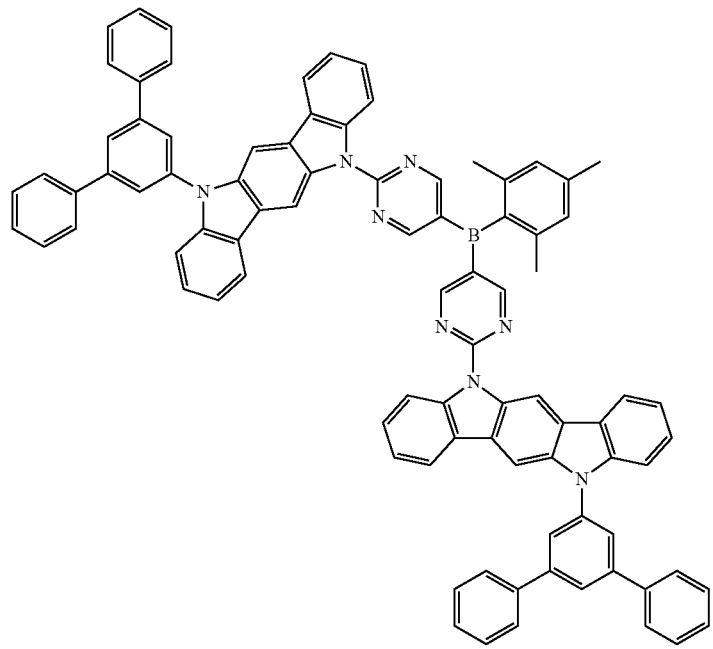
D15
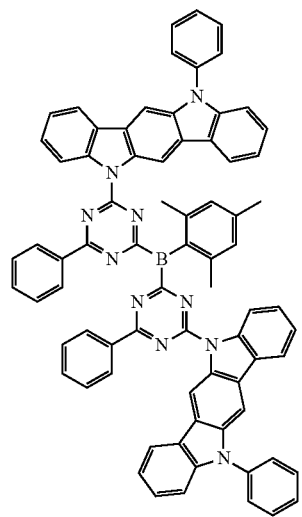
D16
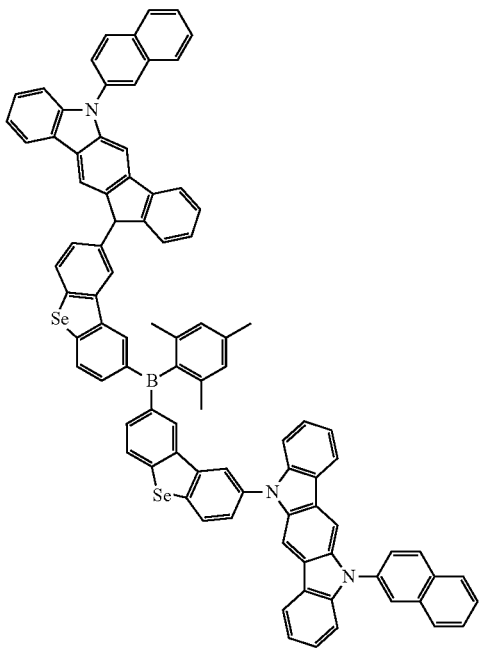
D17

-continued
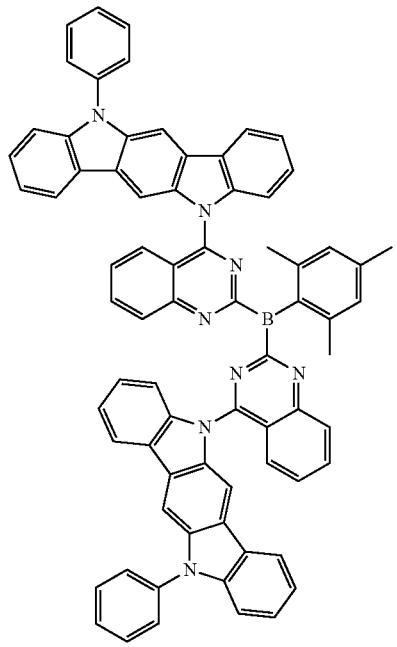
D18
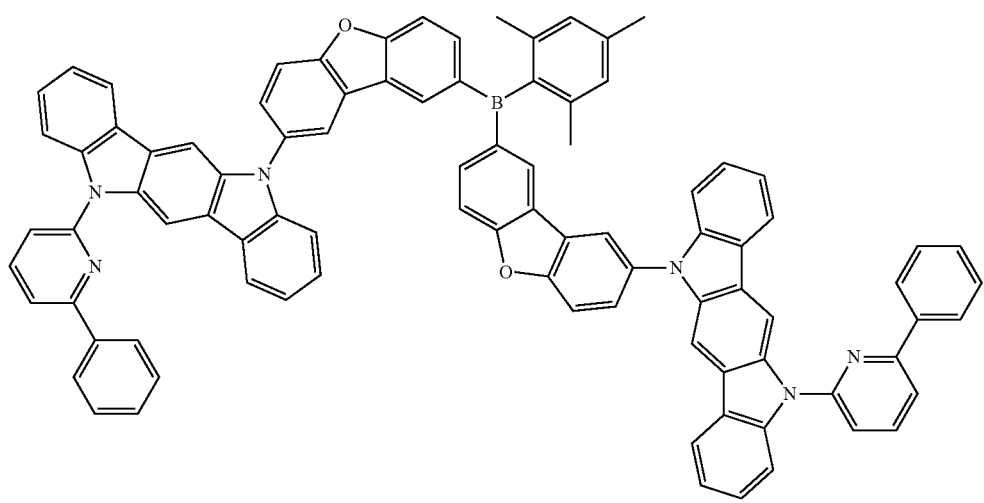
D19

-continued
D20
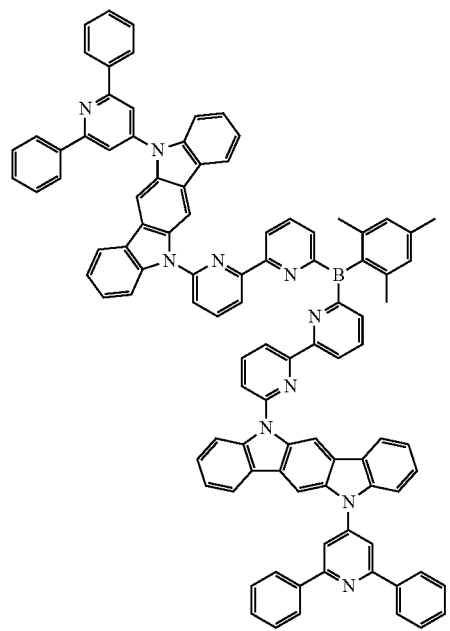
D21
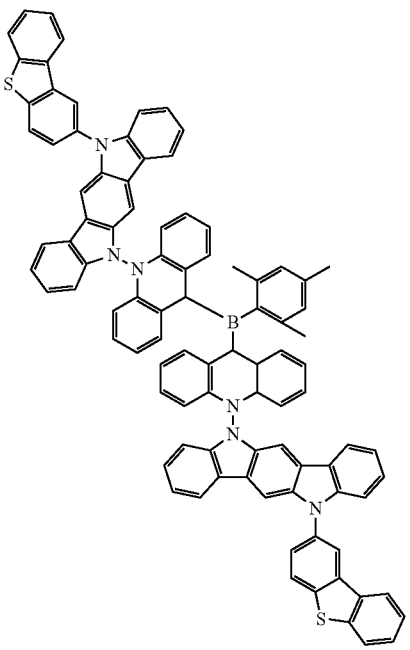
D22
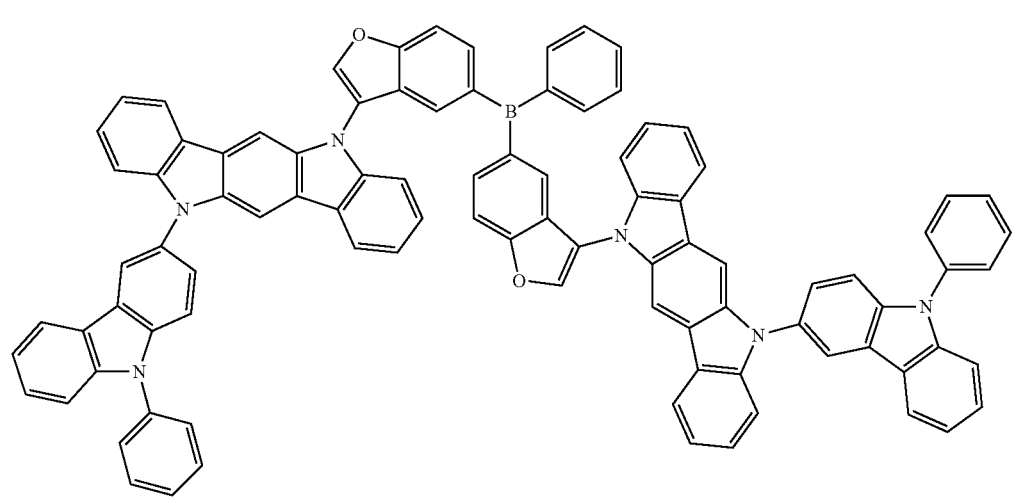

-continued
D23
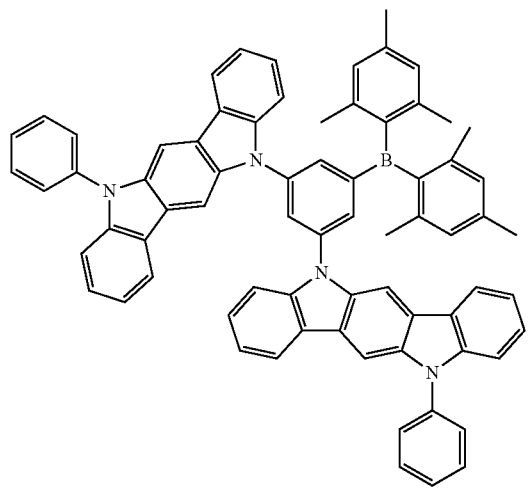
D24
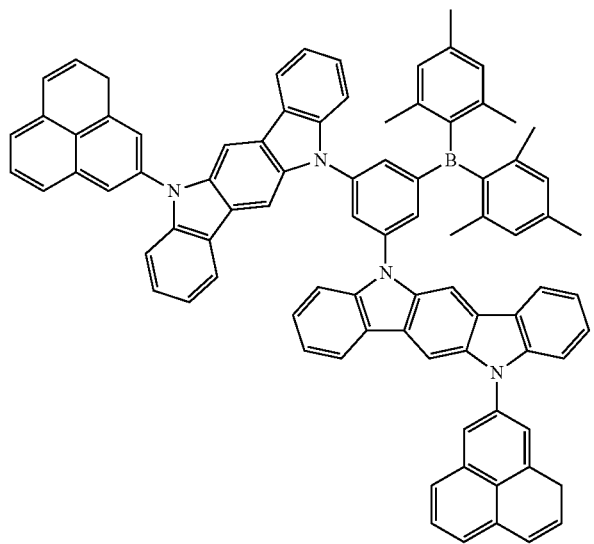
D25
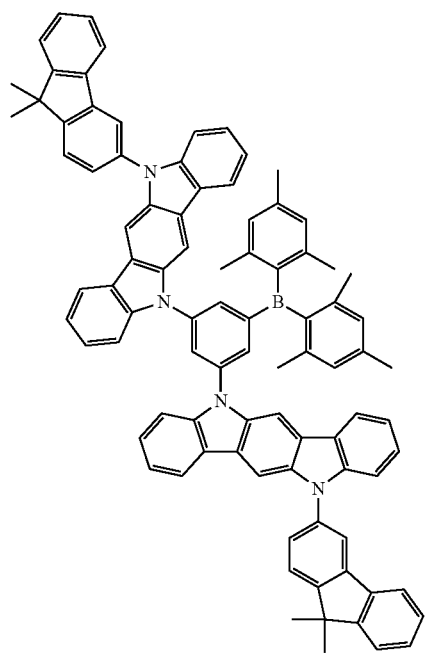
D26
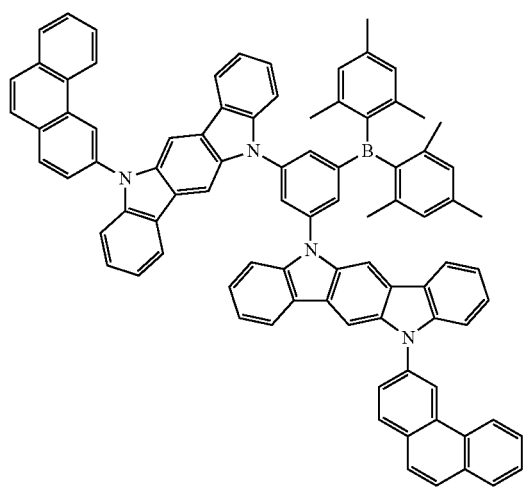

-continued
D27
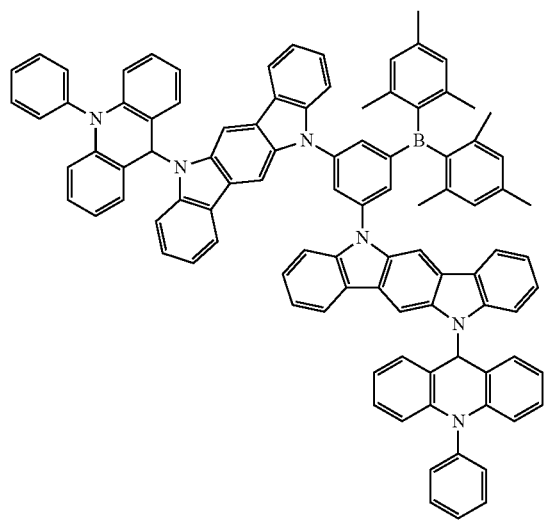
D28
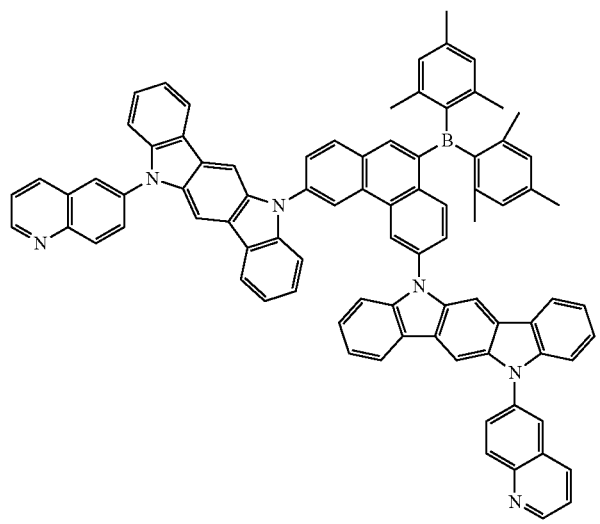
D29
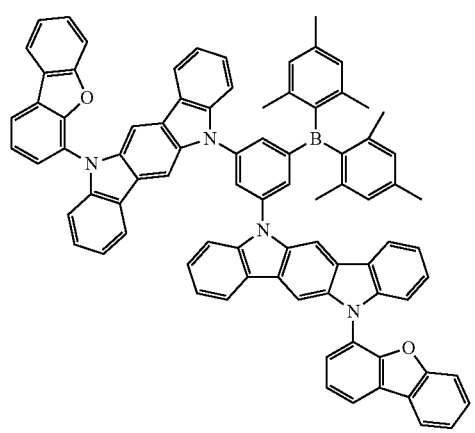
D30
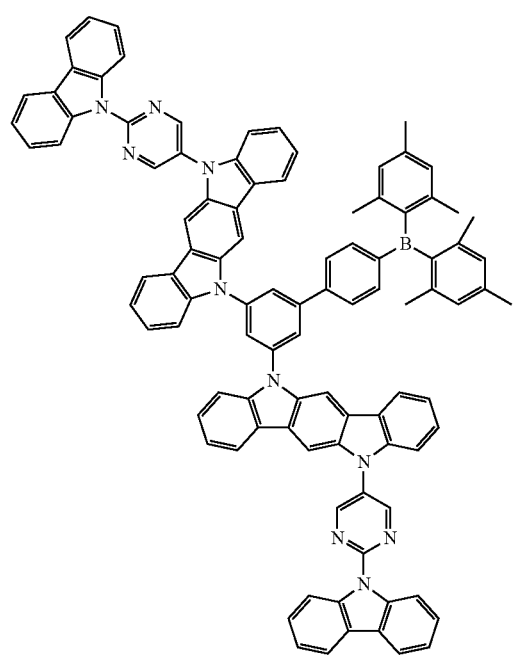

-continued
D31
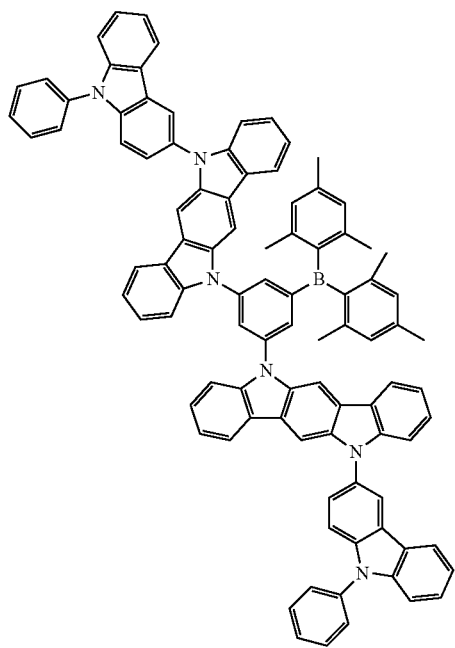
D32
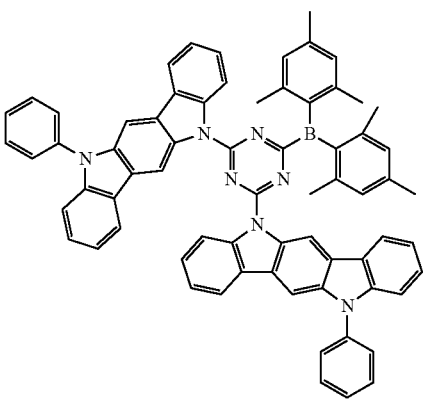
D33
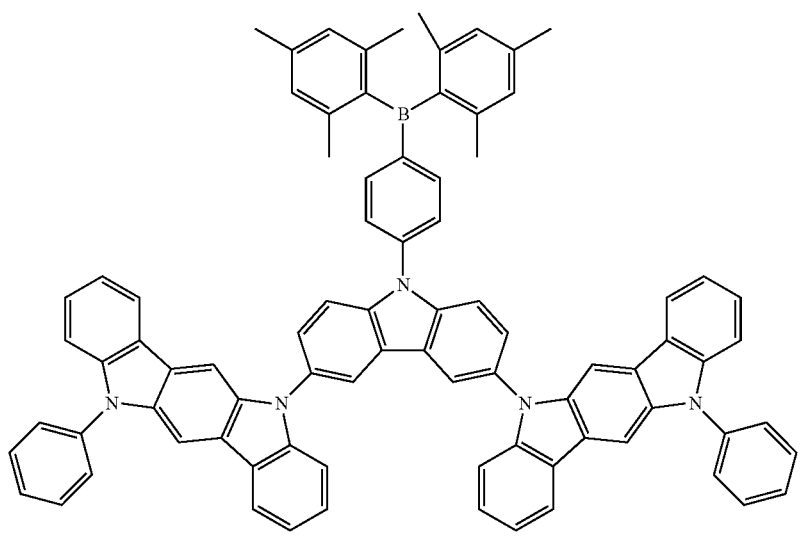

D34
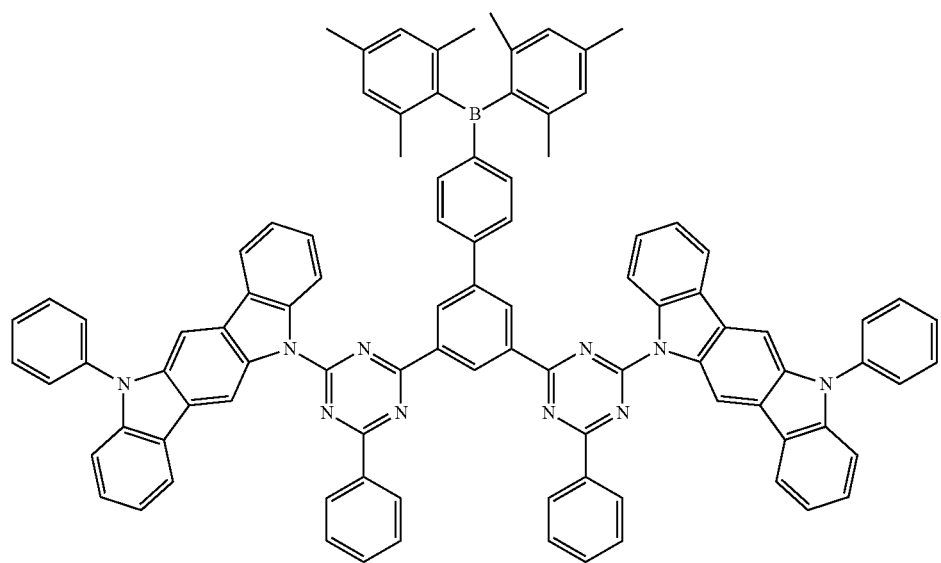
D35
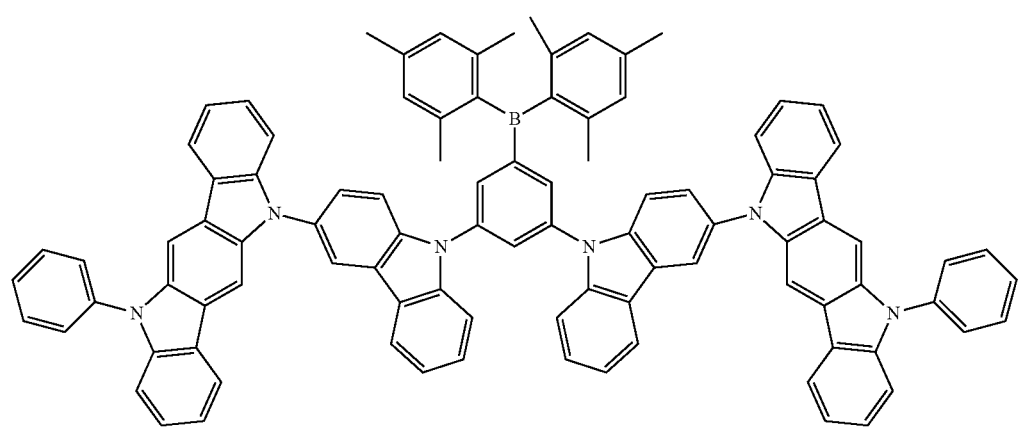
D36
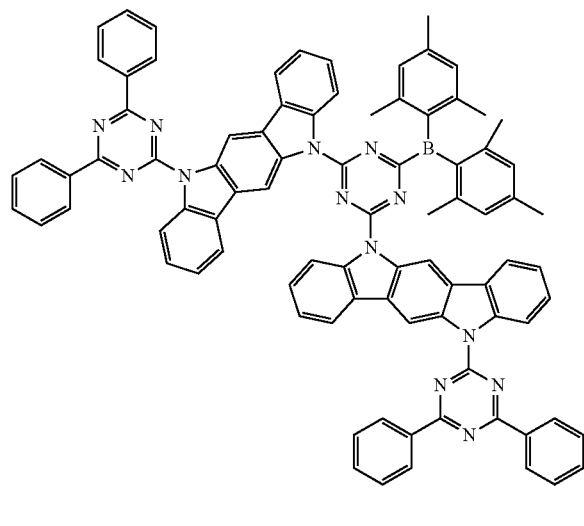
D37
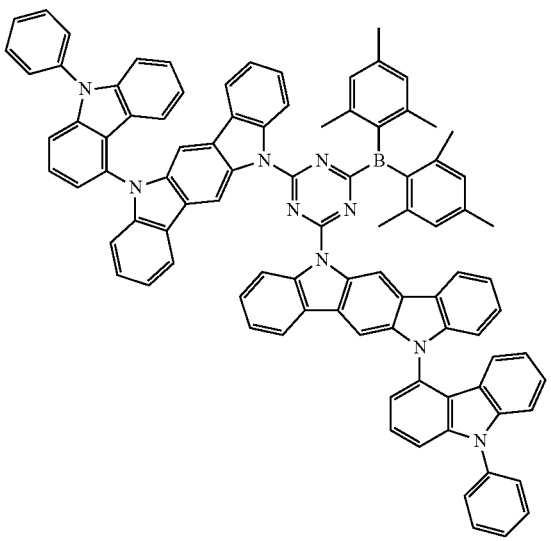

-continued
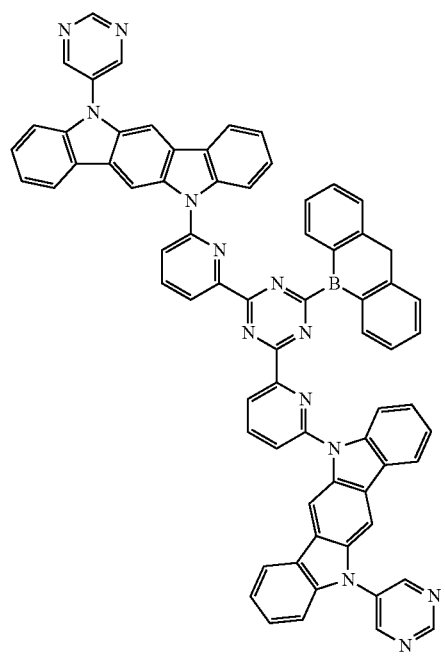
D38
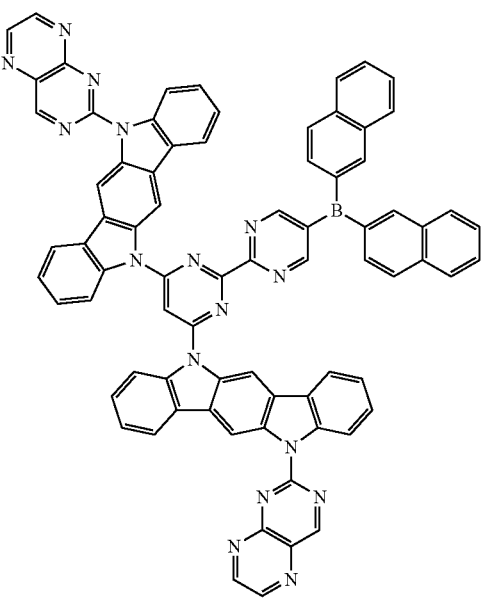
D39
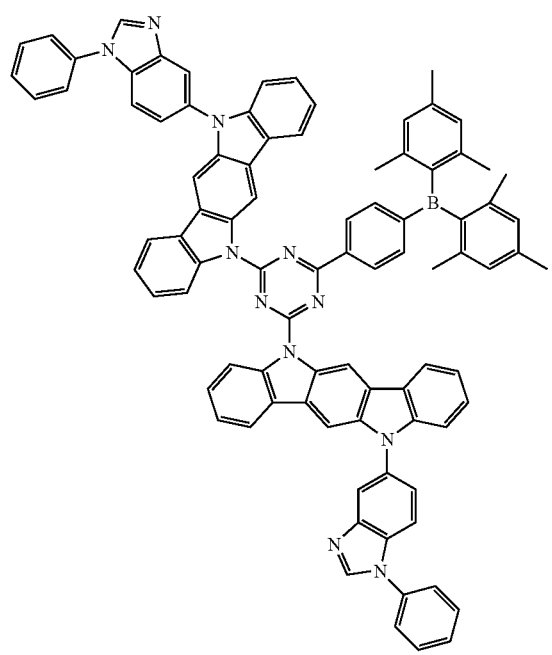
D40
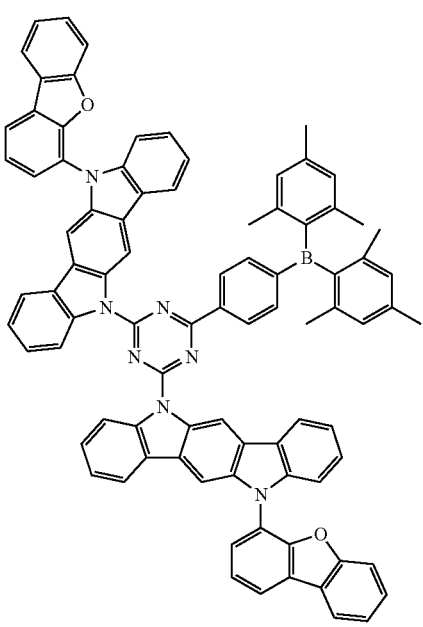
D41

123
-continued
D42
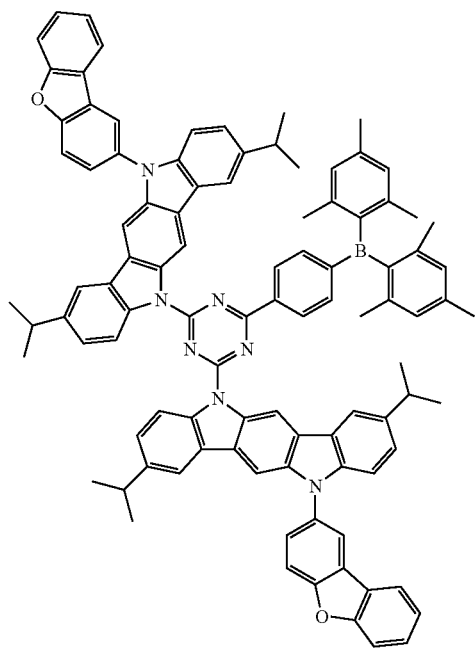
124
D43
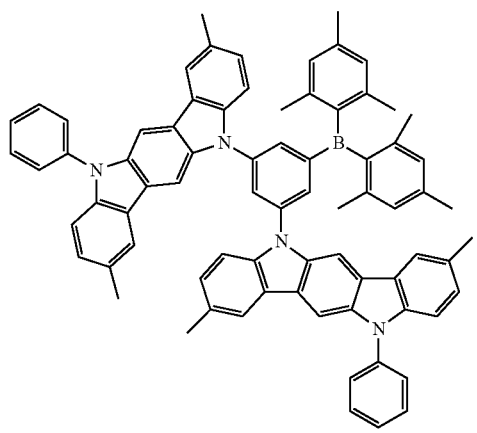
D44
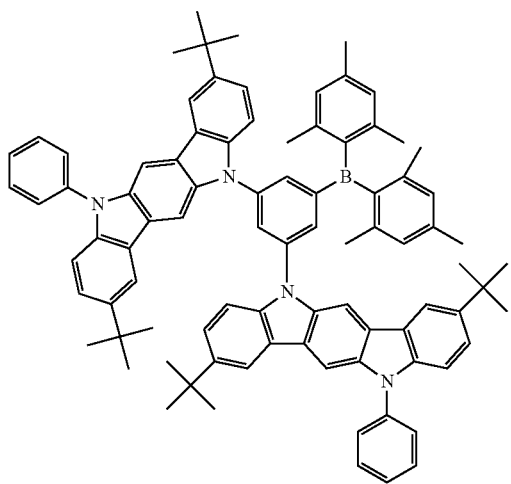
D45
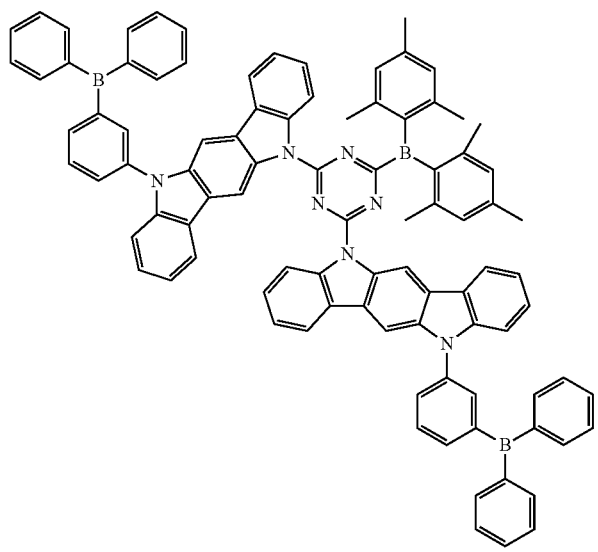

-continued
D46
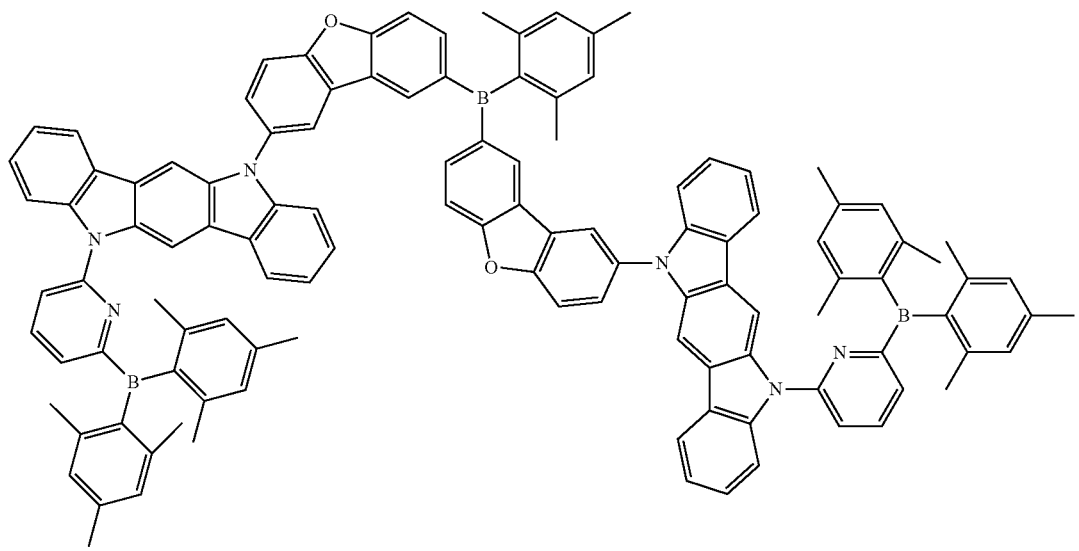
D47
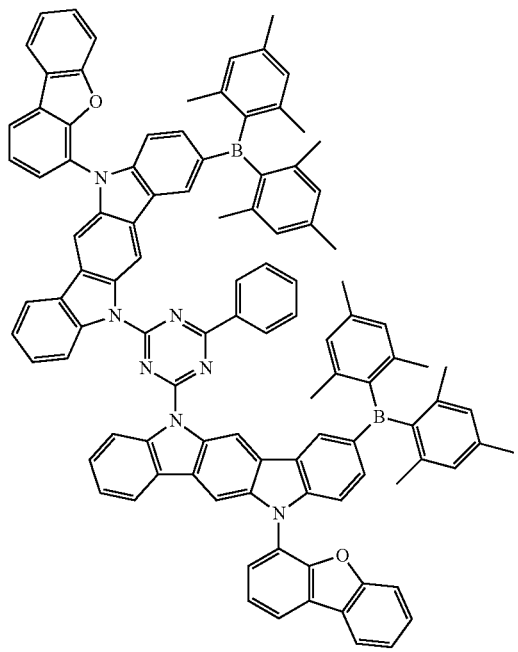
D48
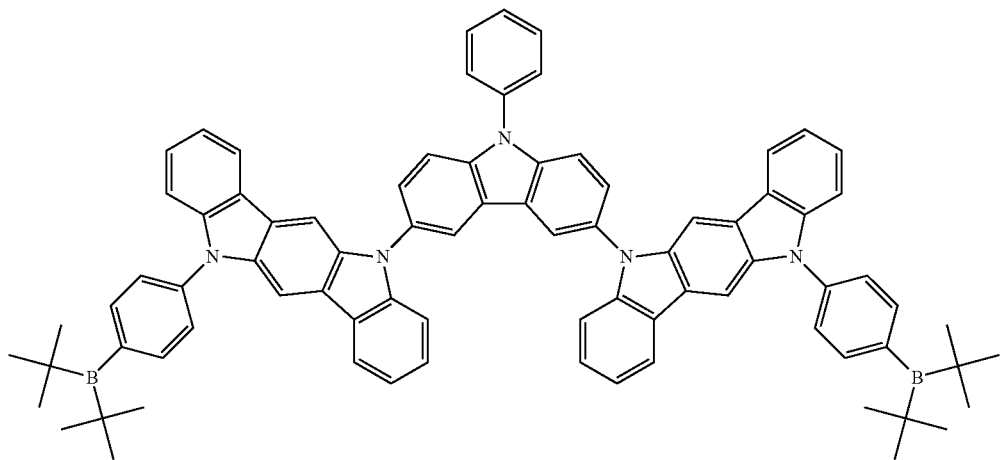

-continued
E1
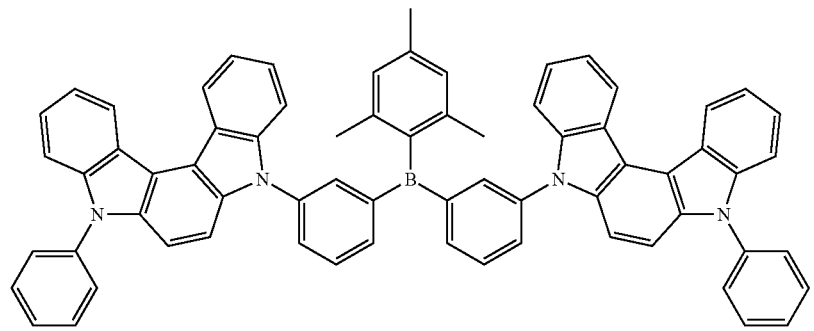
E2
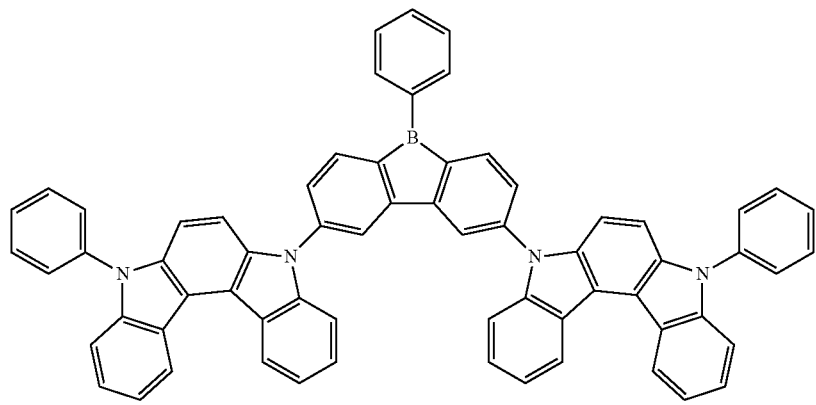
E3
E4
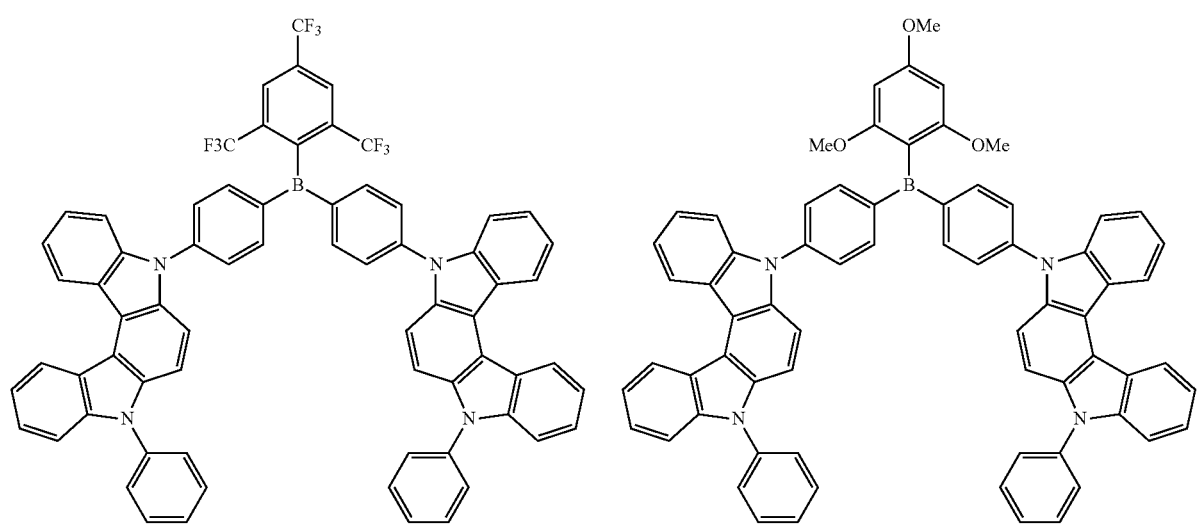

-continued
E5
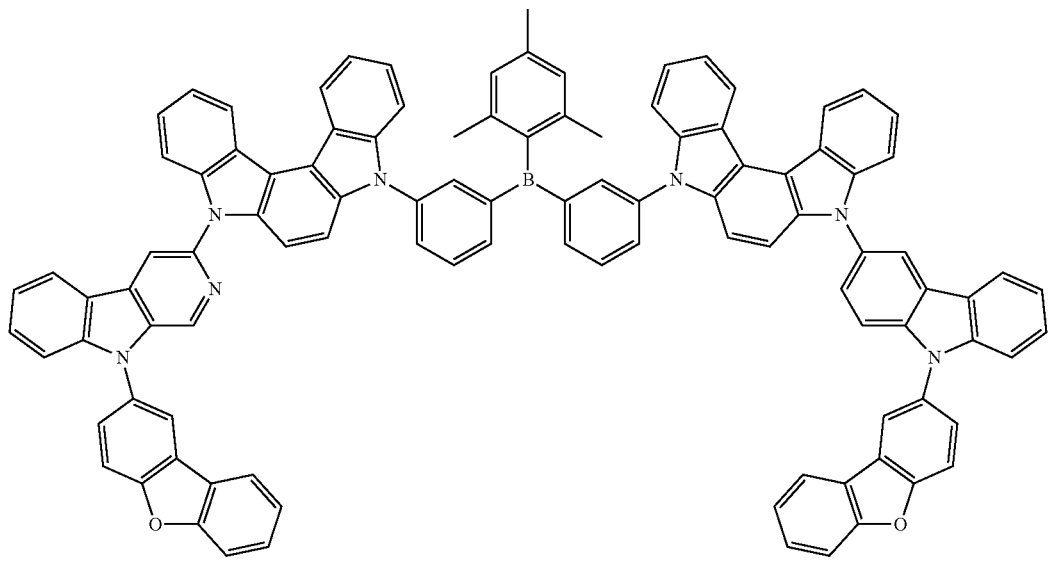
E6
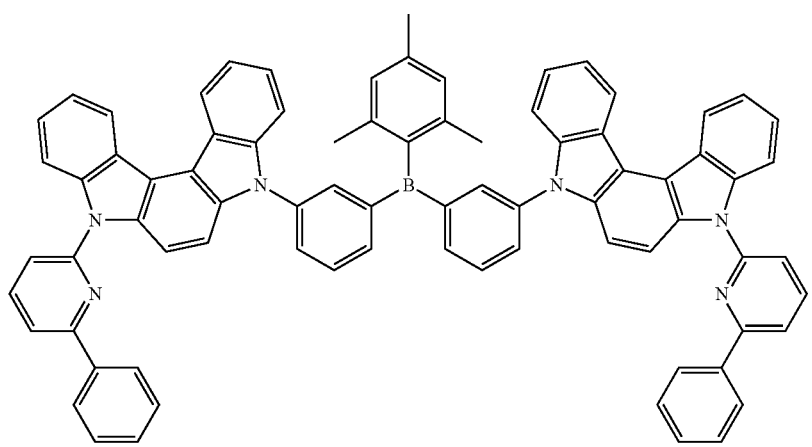
E7
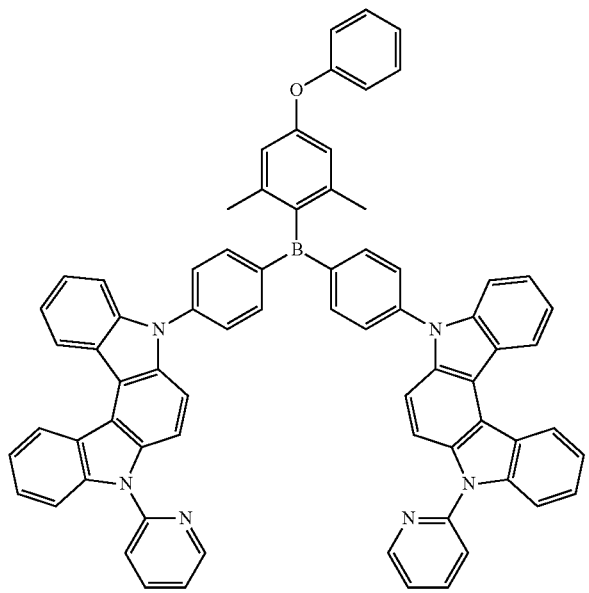

-continued
E8
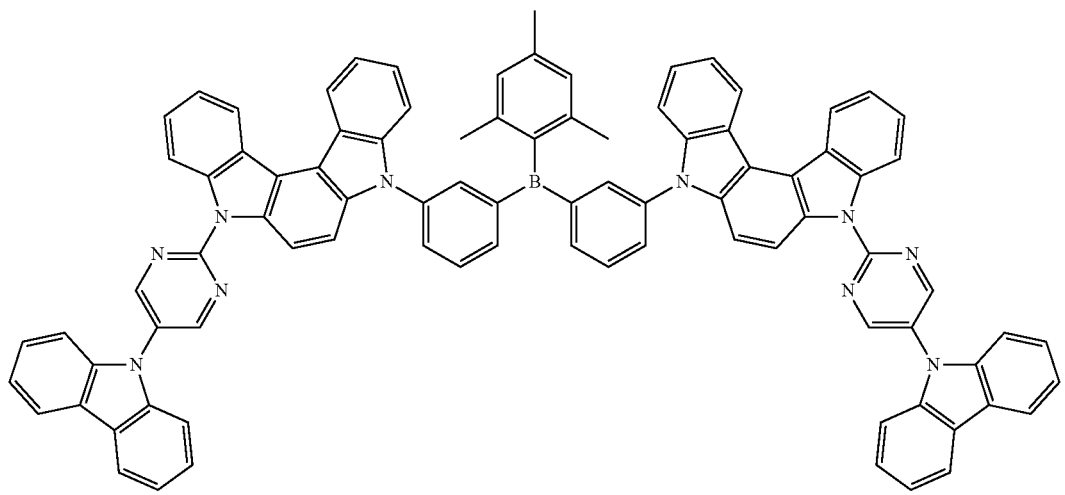
E9
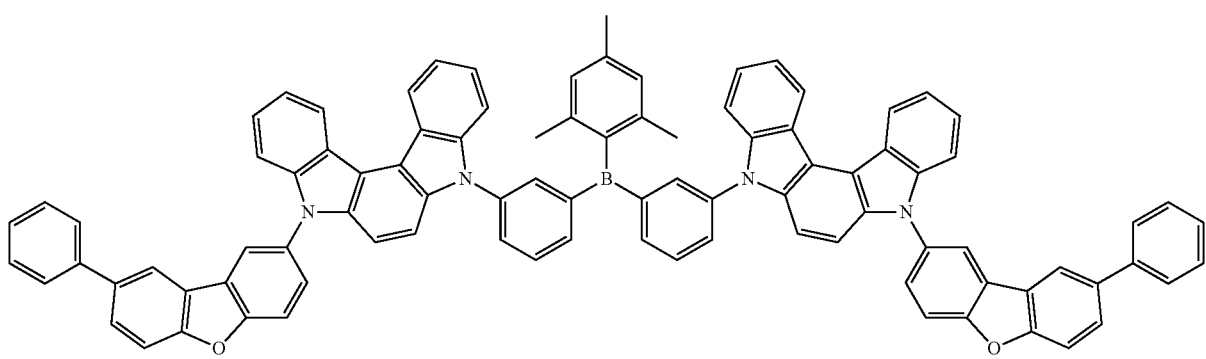
E10
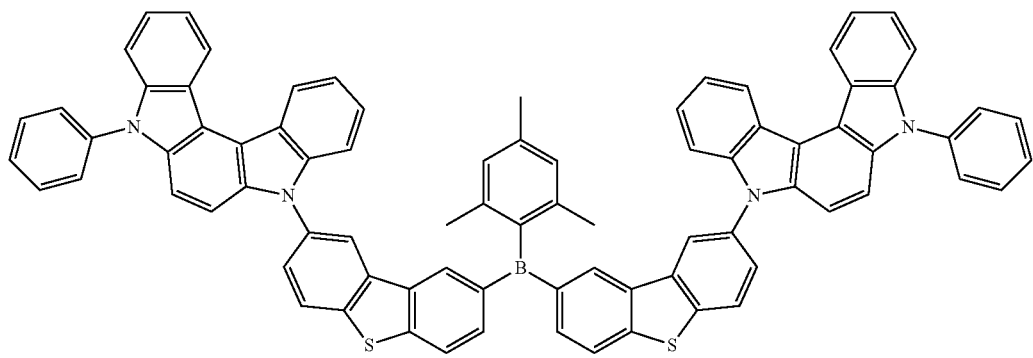
E11
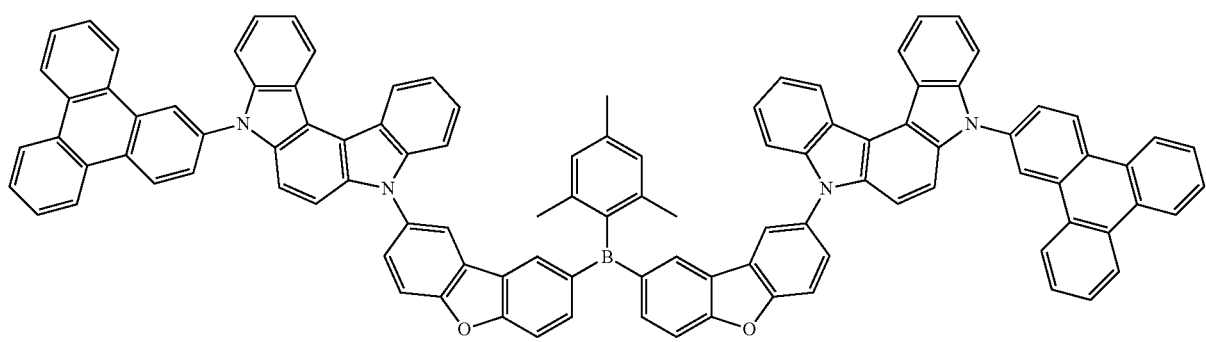

-continued
E12
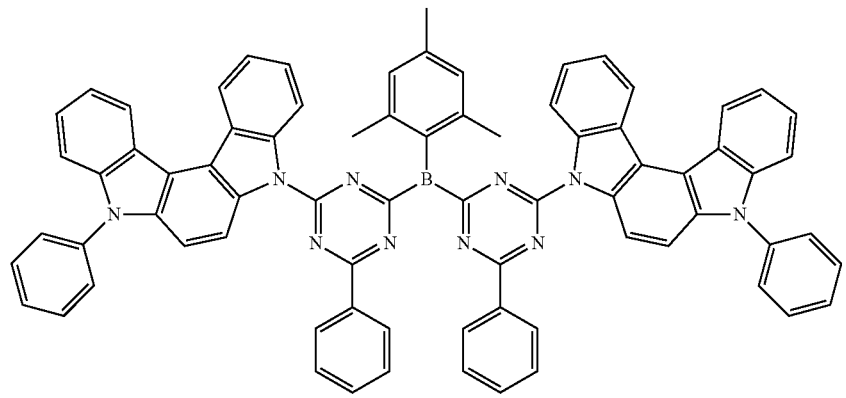
E13
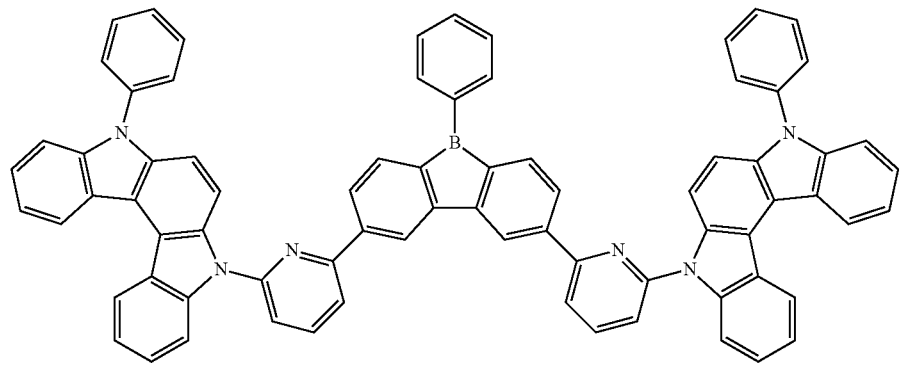
E14
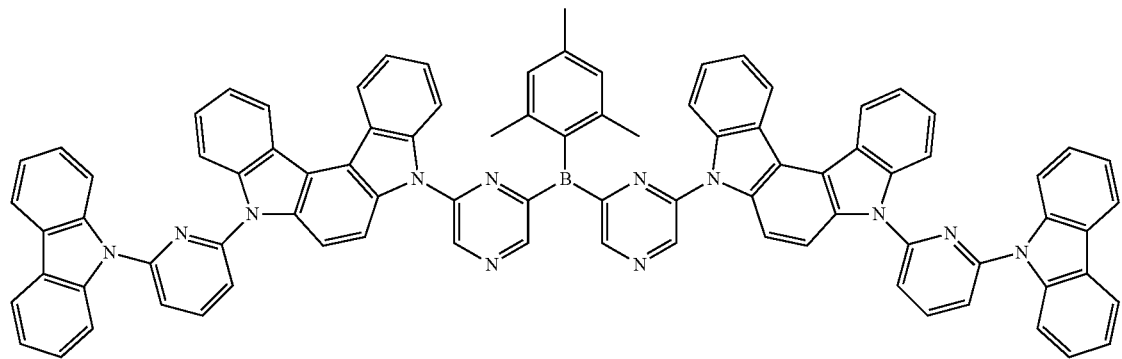
E15
E16
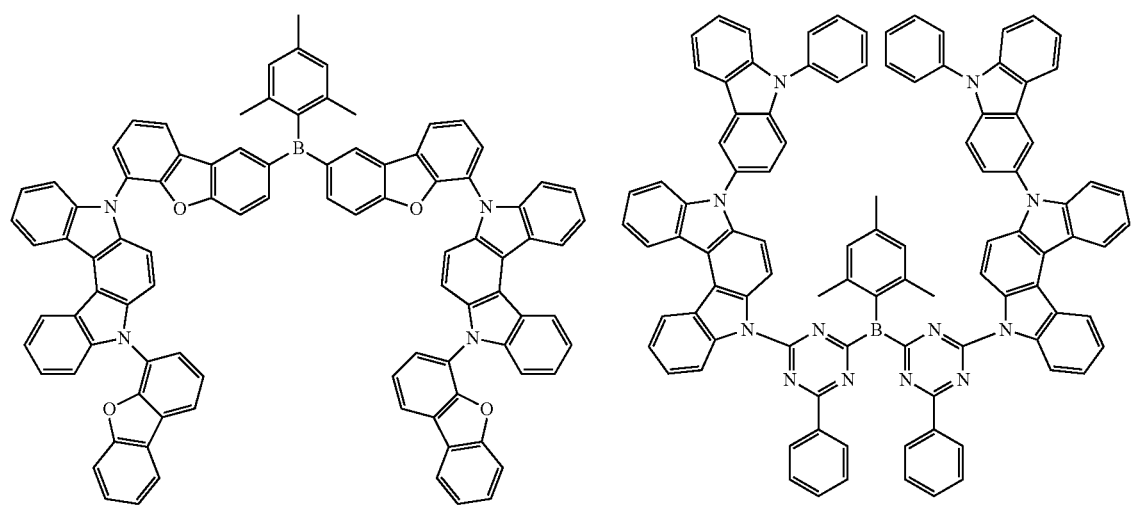

-continued
E17
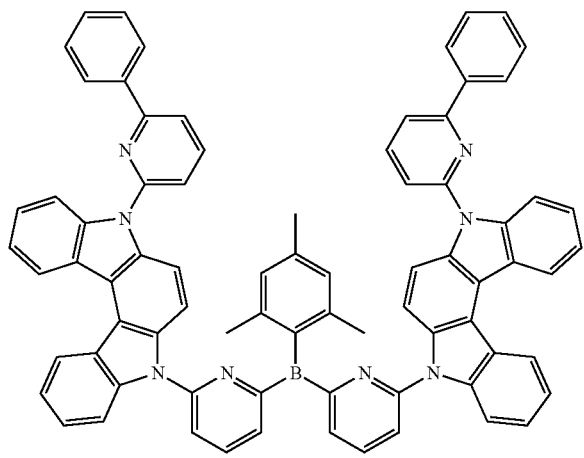
E18
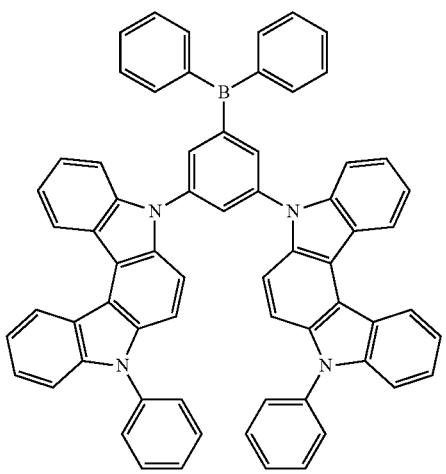
E19
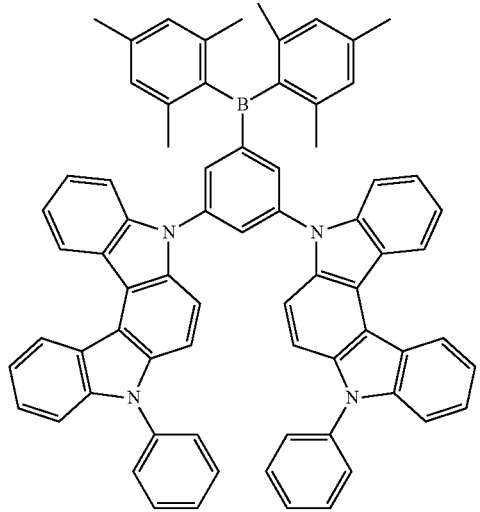
E20
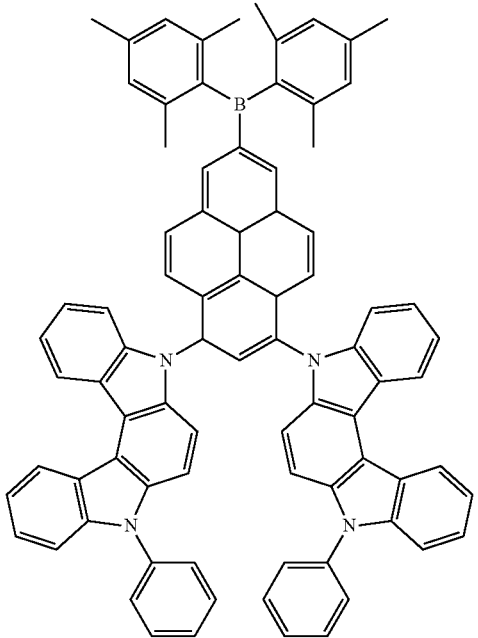

E21
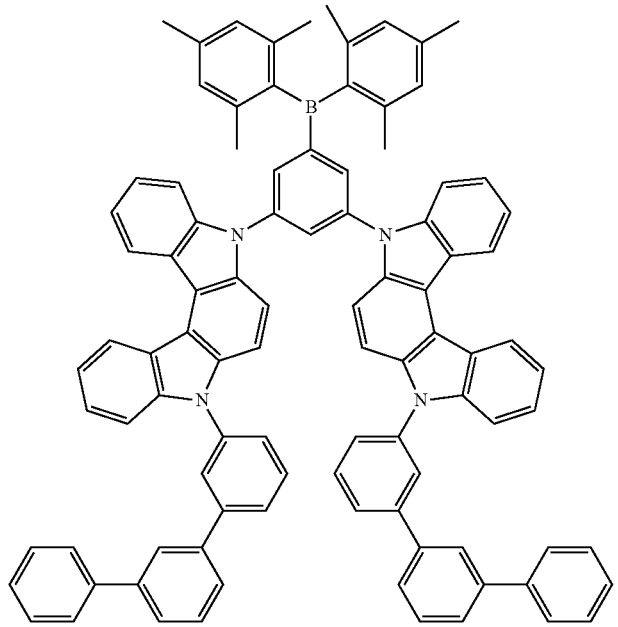
E22
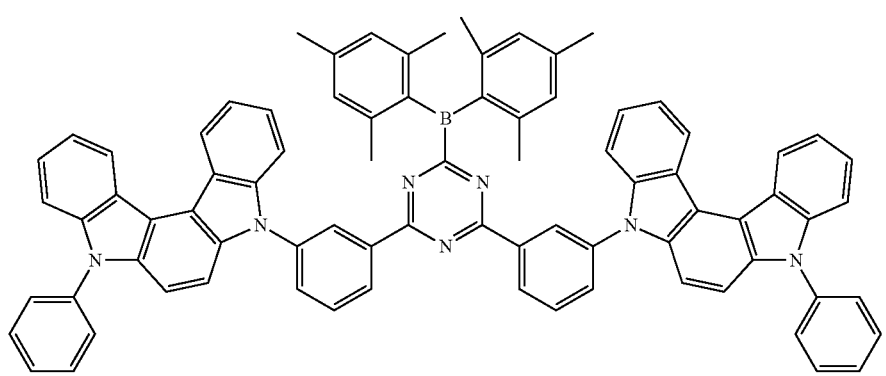
E23
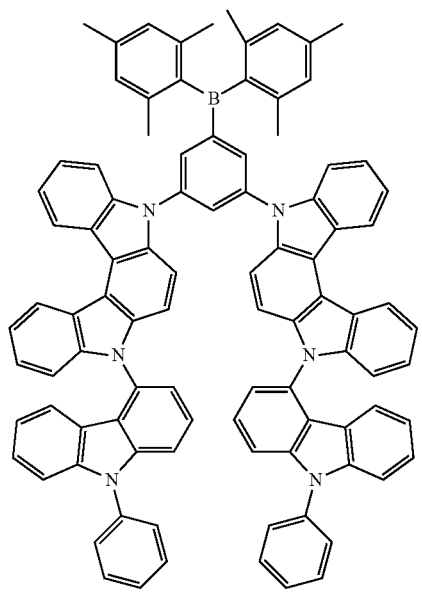
E24
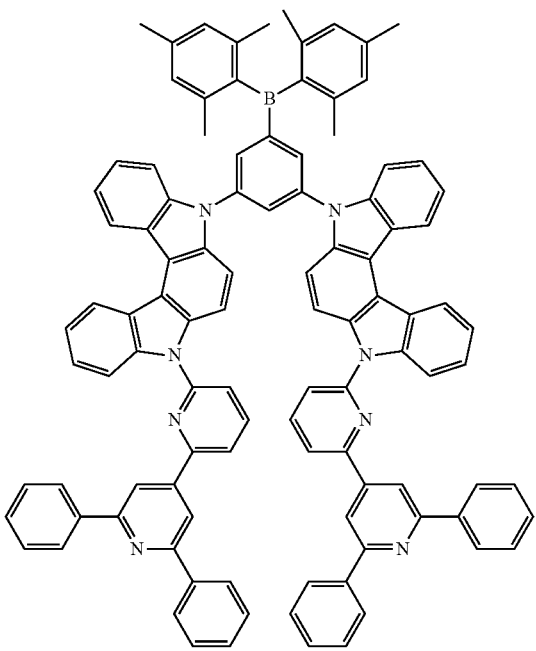

-continued
E25
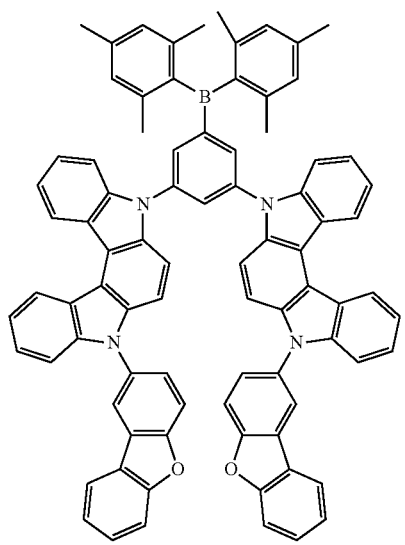
E26
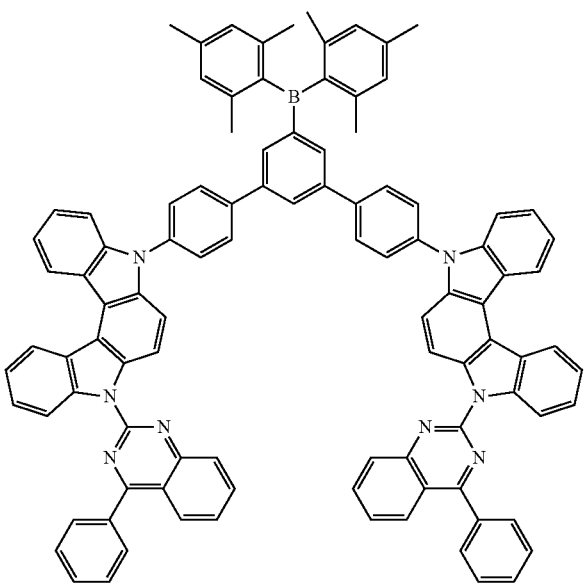
E27
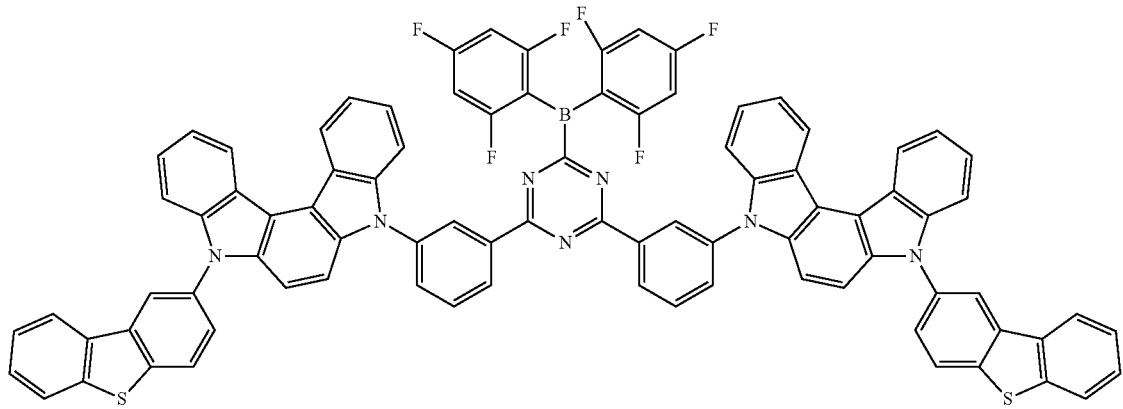
E28
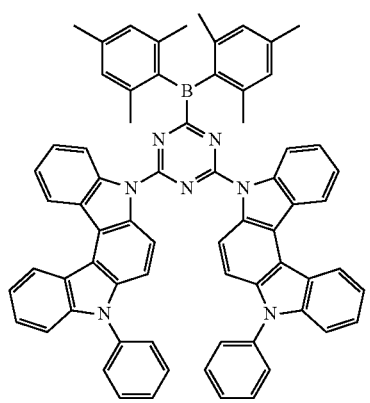
E29
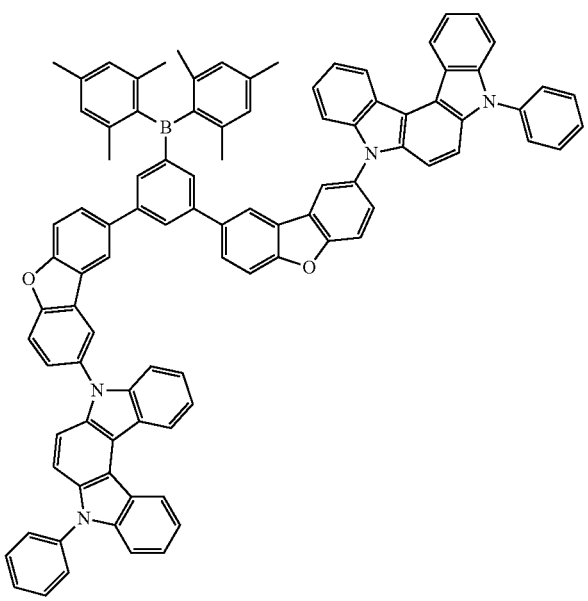

-continued
141
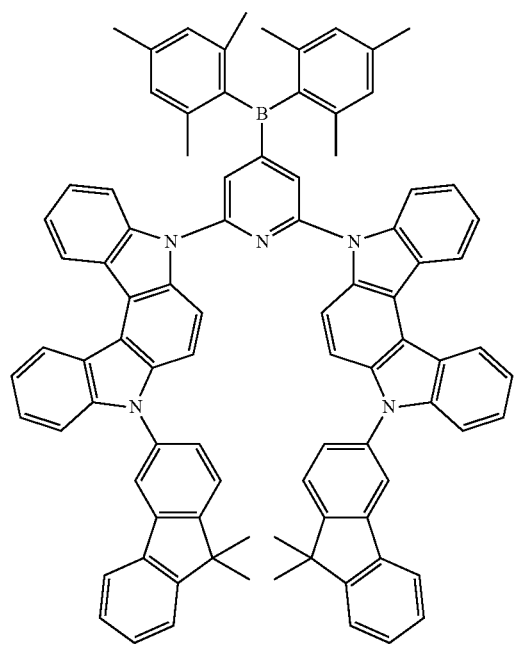
E30
142
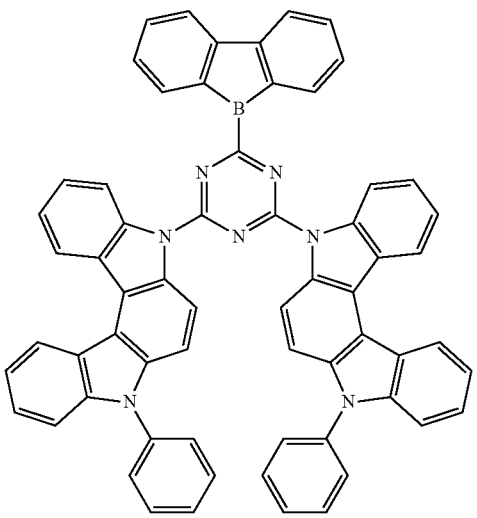
E31
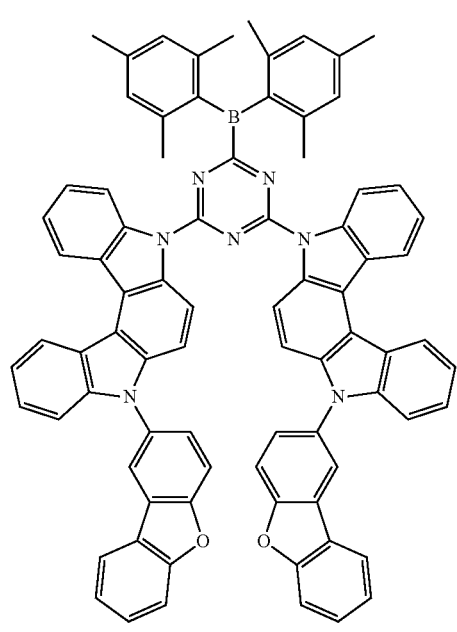
E32
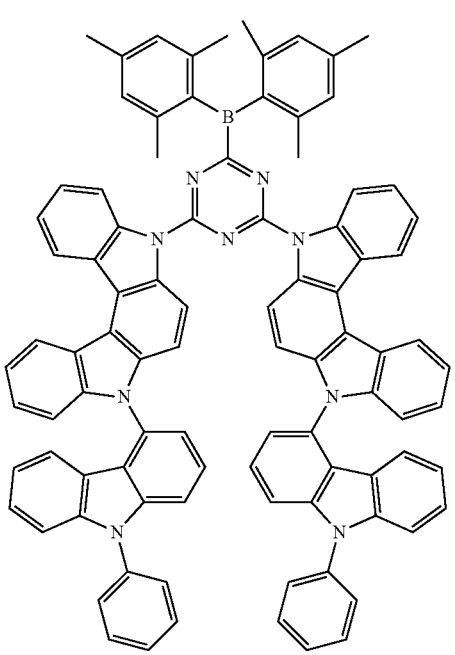
E33

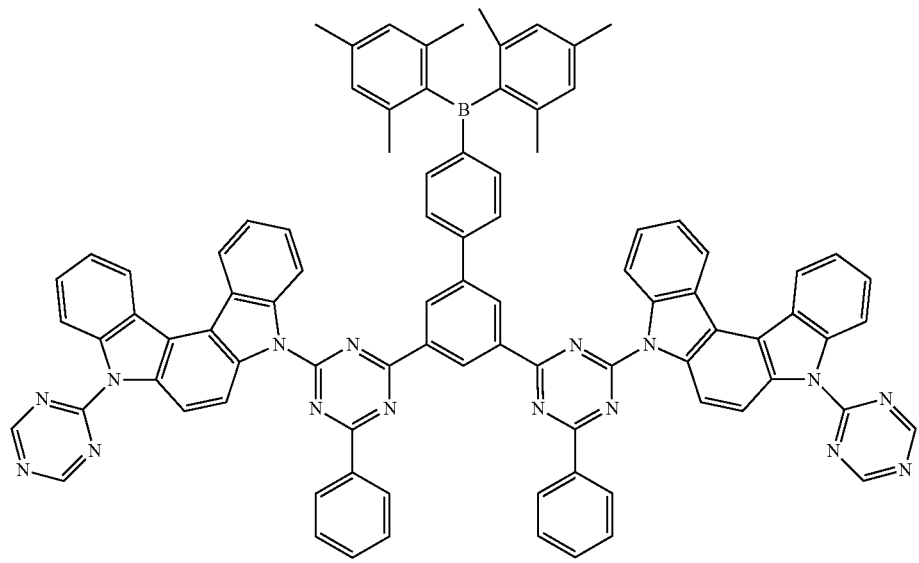
E34
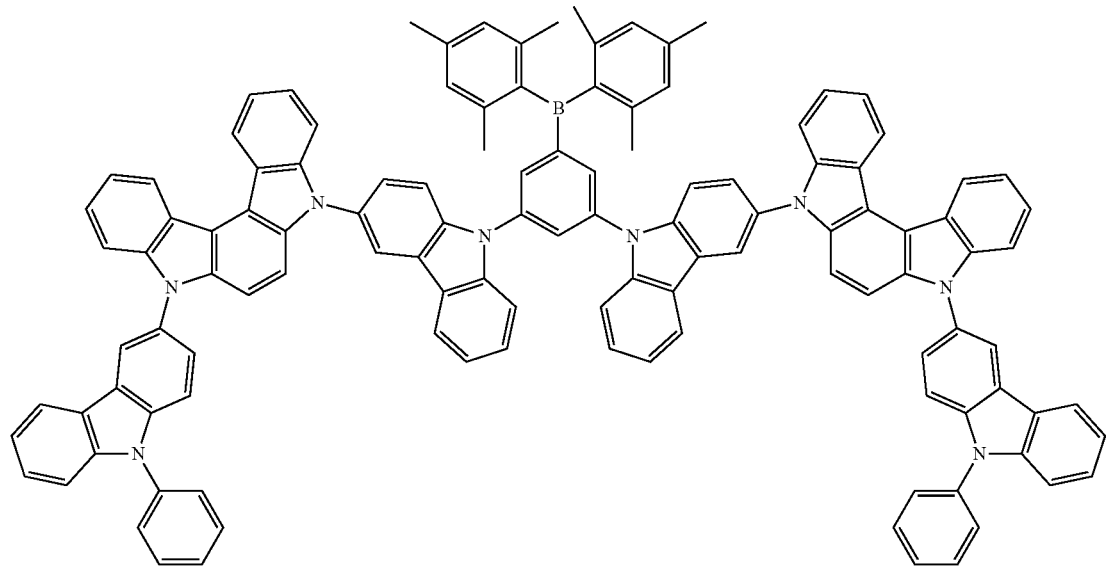
E35
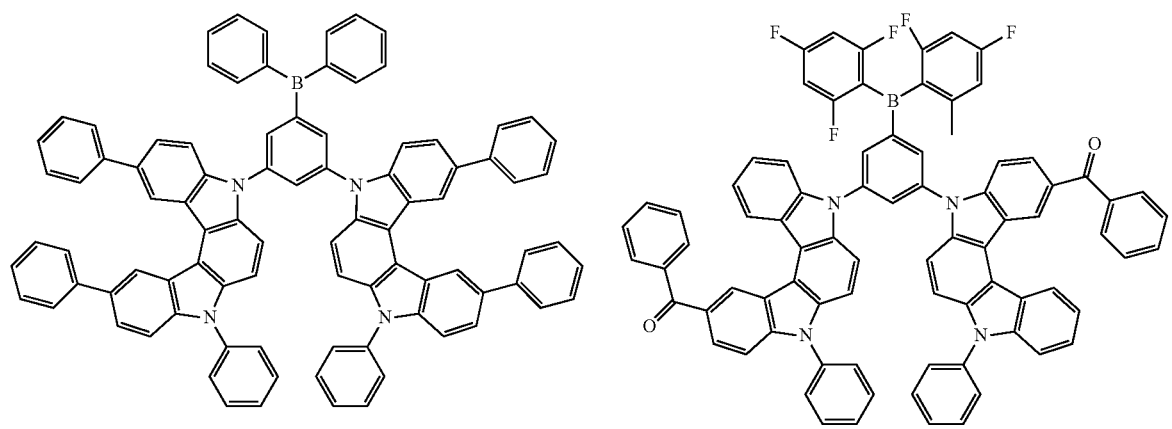
E36
E37

-continued
E38
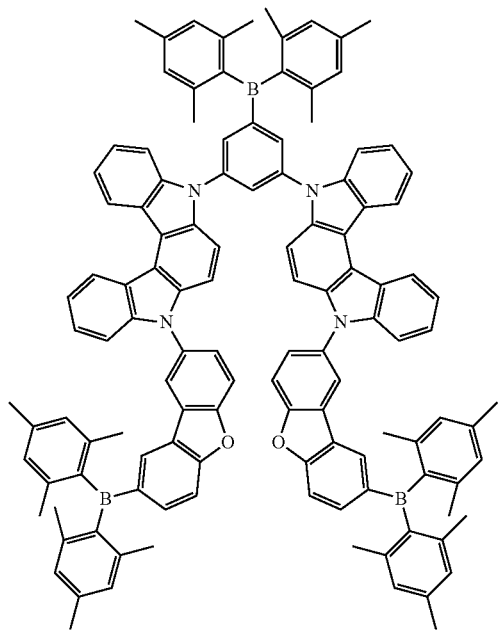
E39
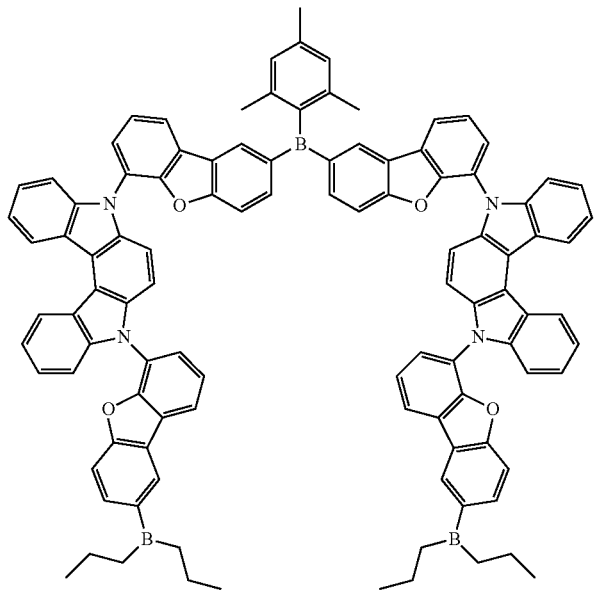
E40
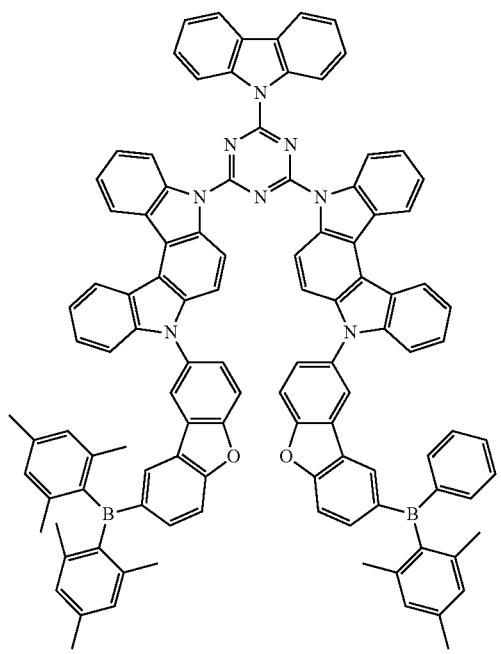
E41
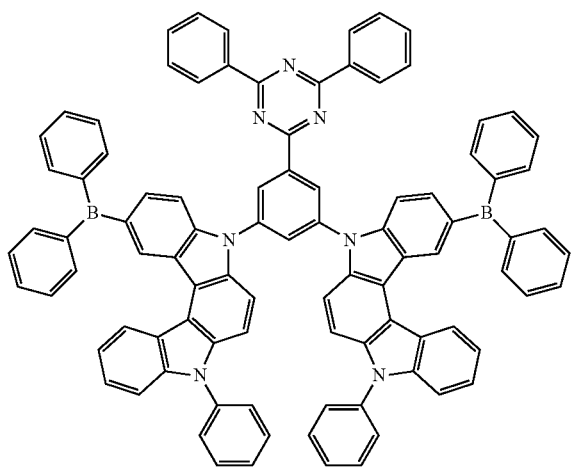
F1
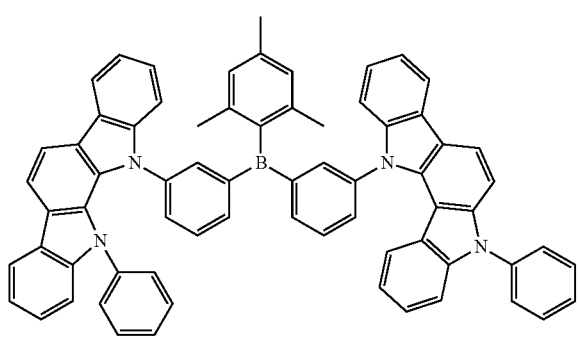
F2
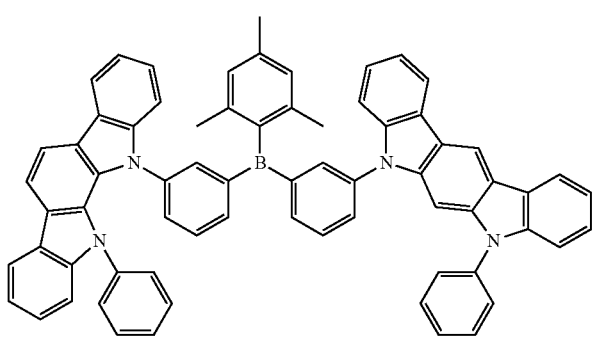

-continued
F3
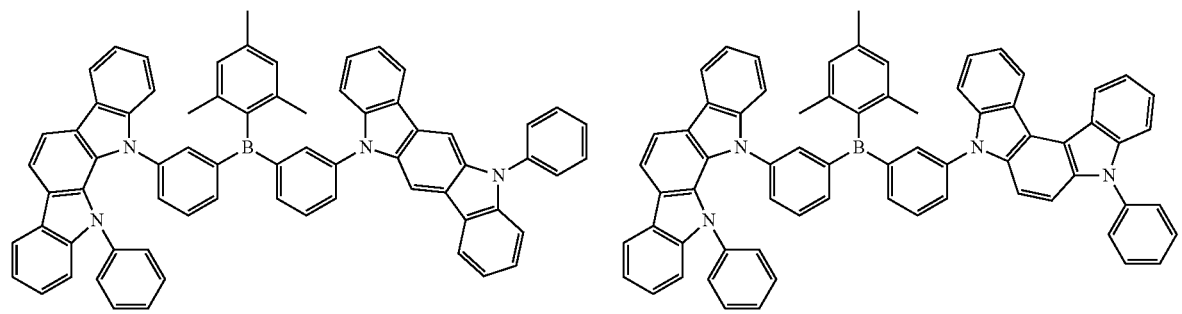
F4
F5
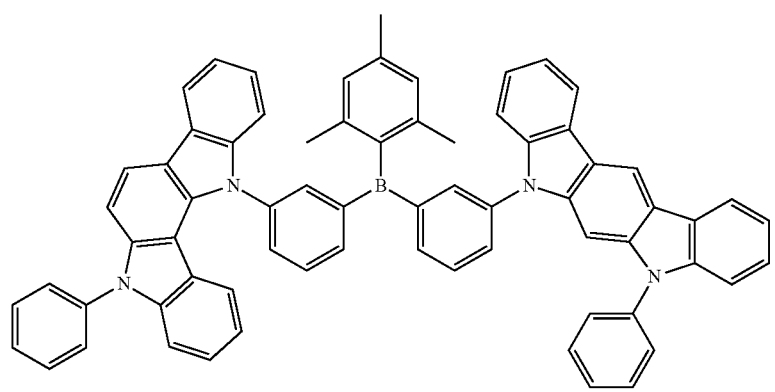
F6
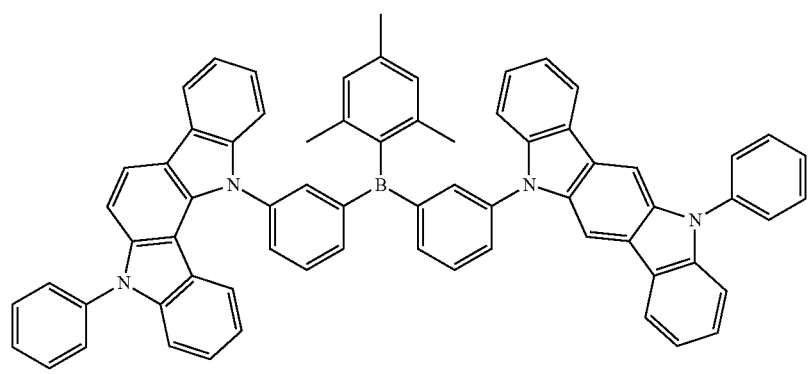
F7
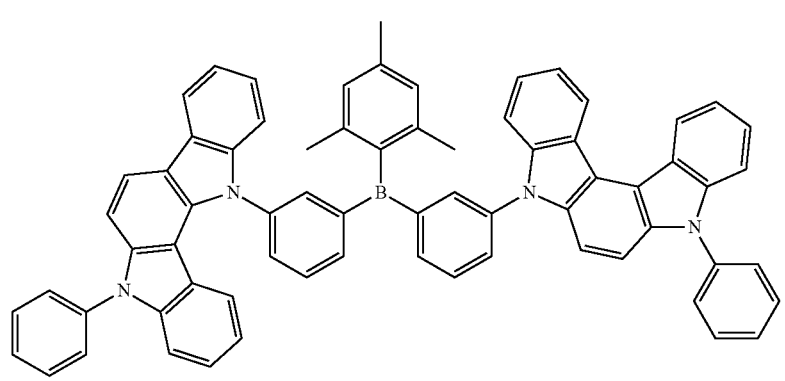

-continued
F8
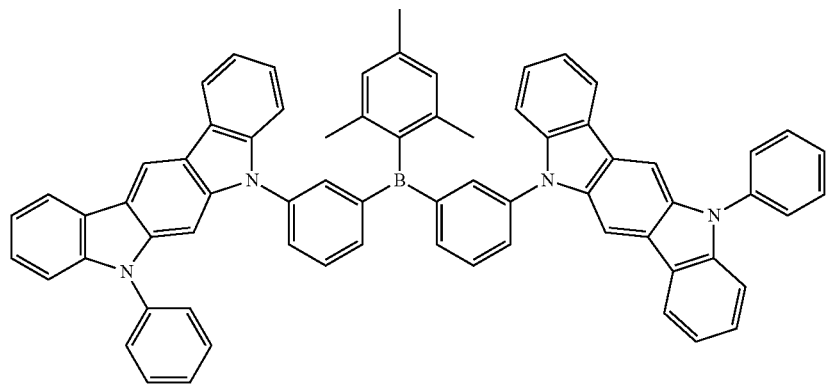
F9
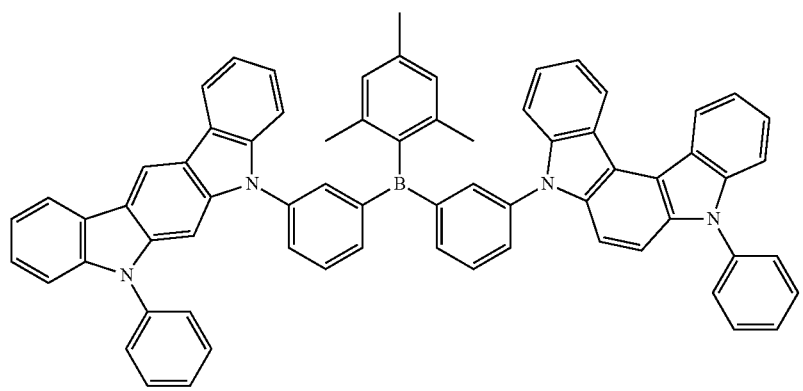
F10
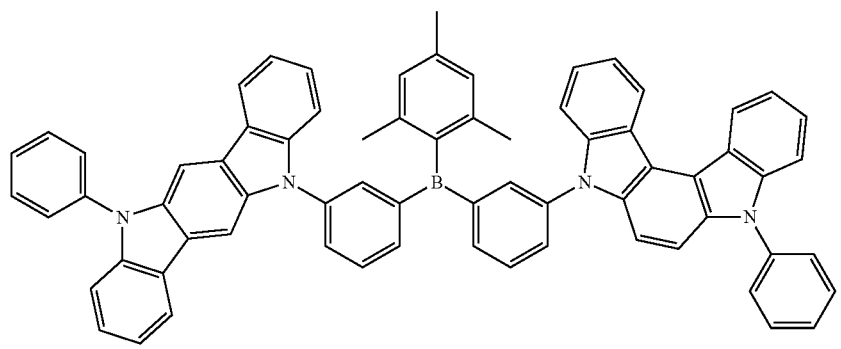
F11 F12
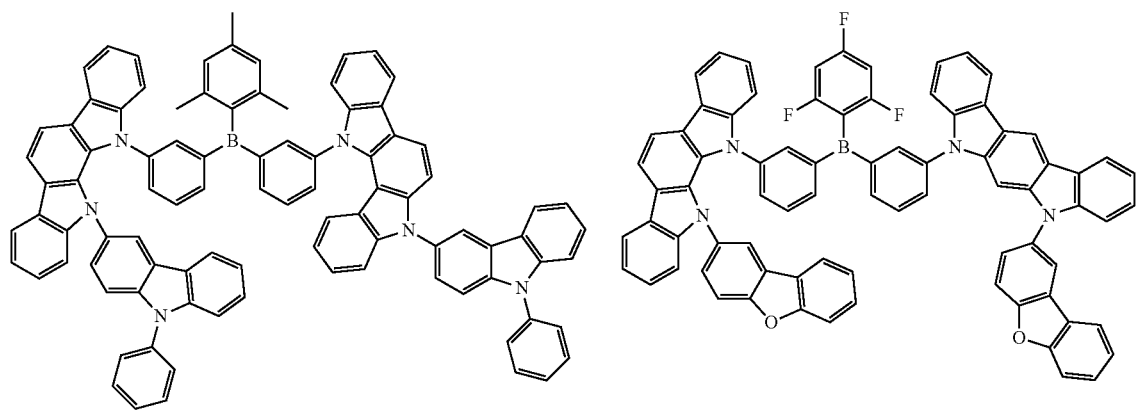

-continued
F13
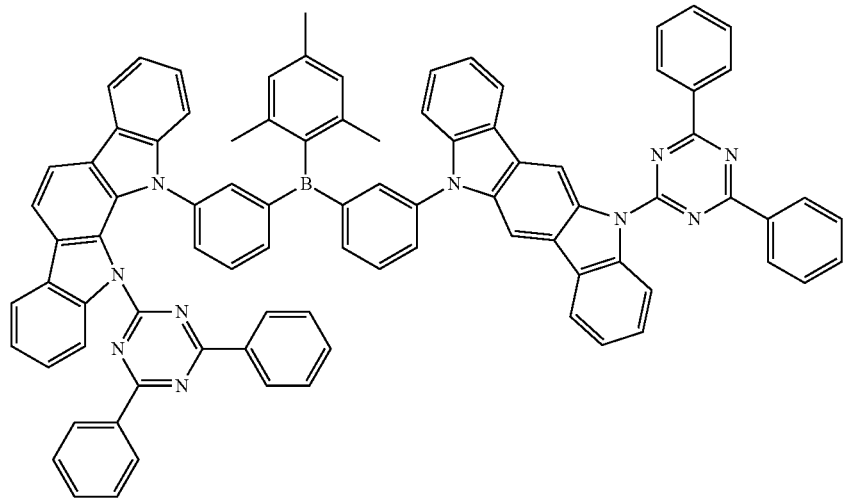
F14
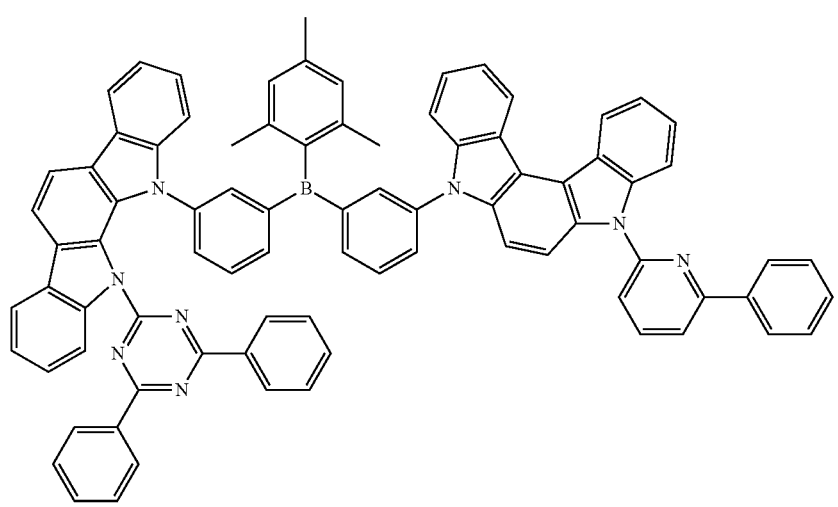
F15
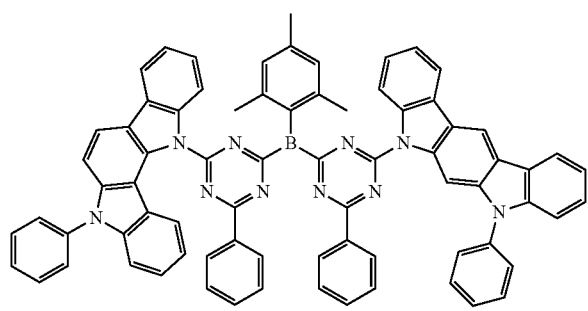
F16
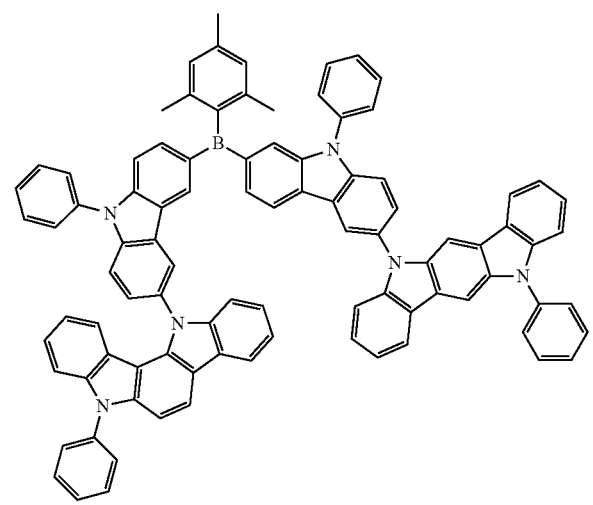

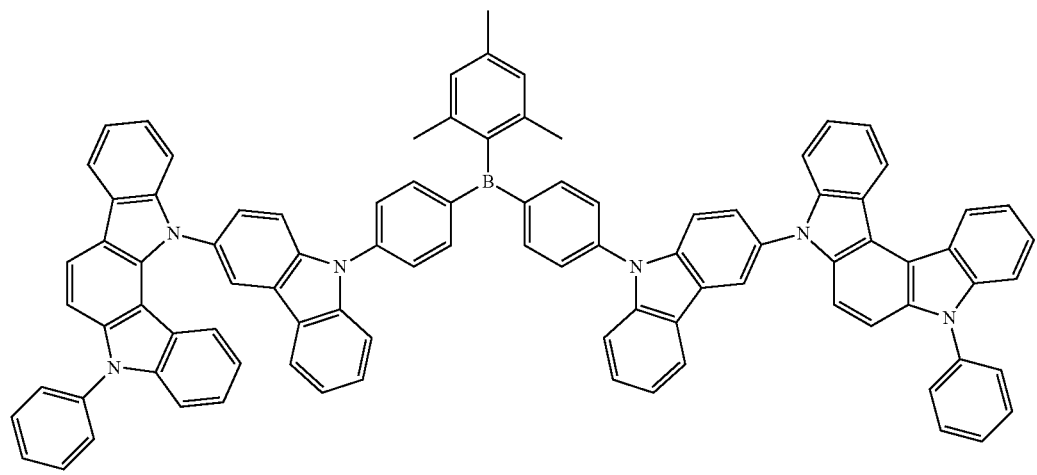
F17
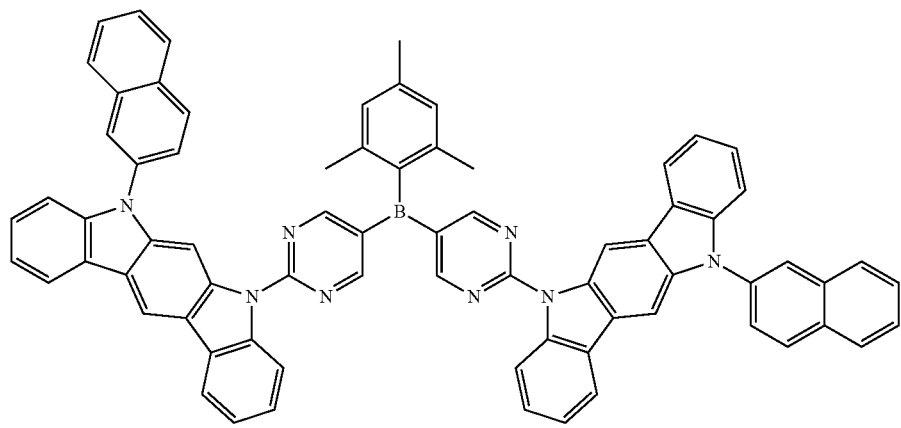
F18
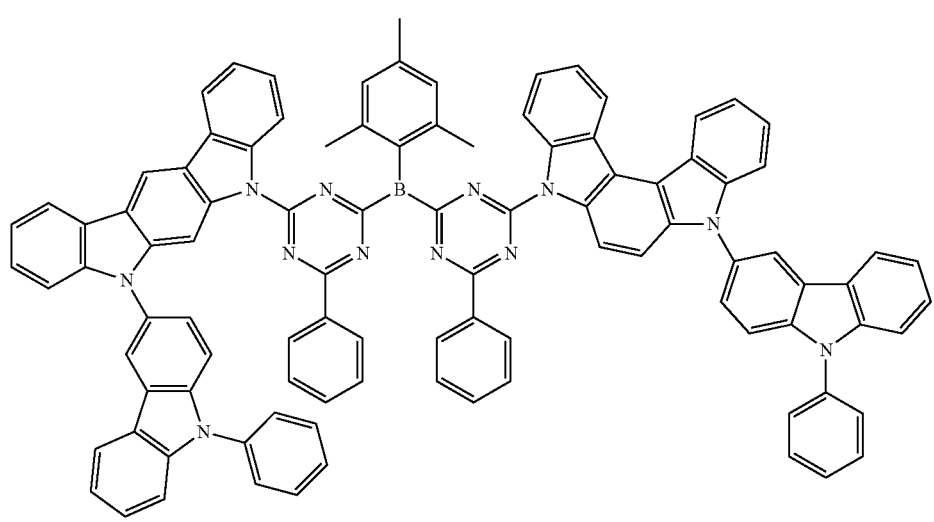
F19

-continued
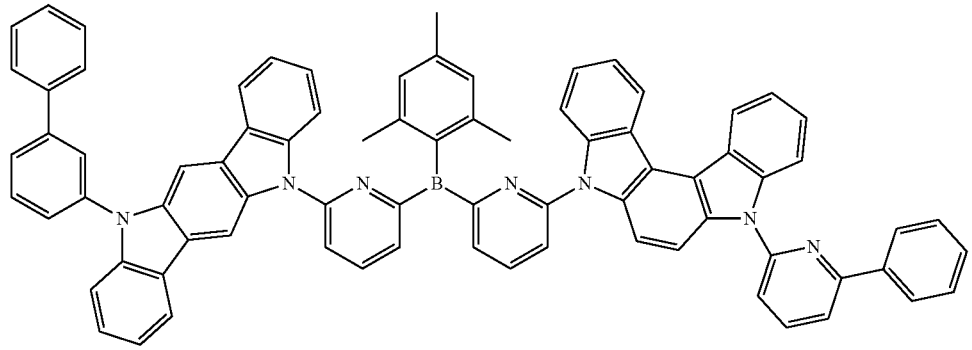
F20
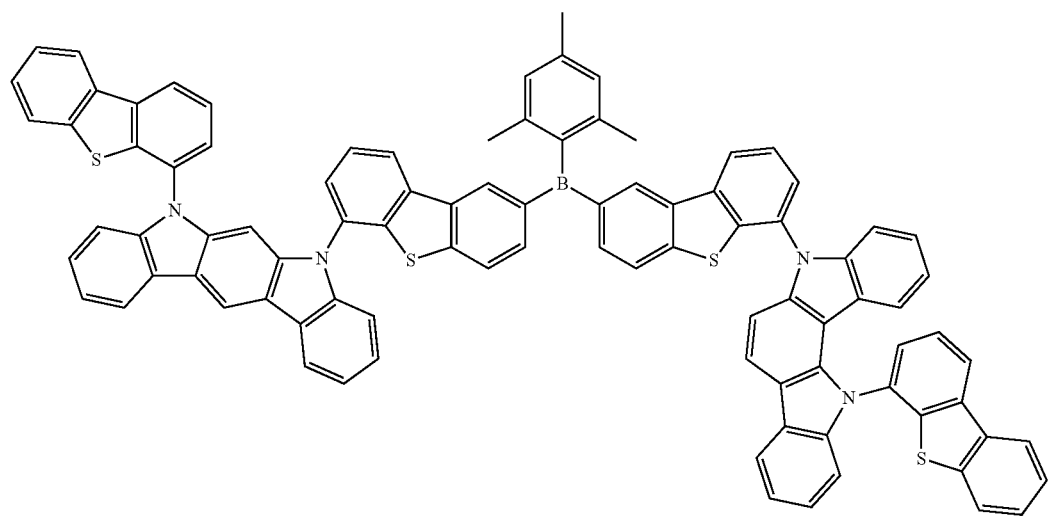
F21
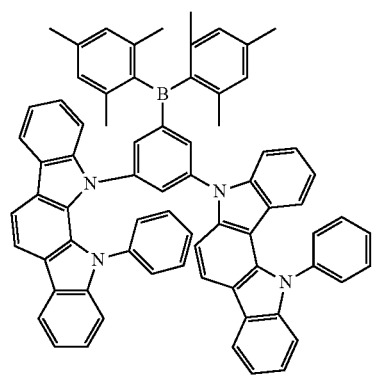
F22
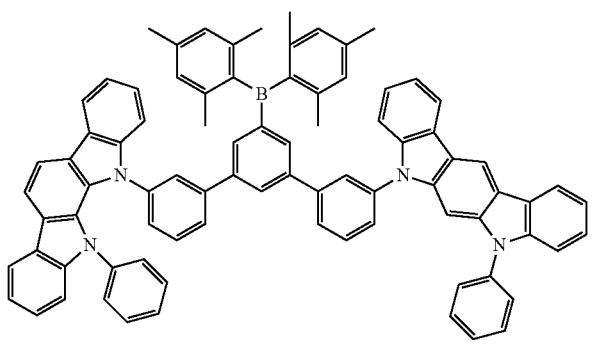
F23

-continued
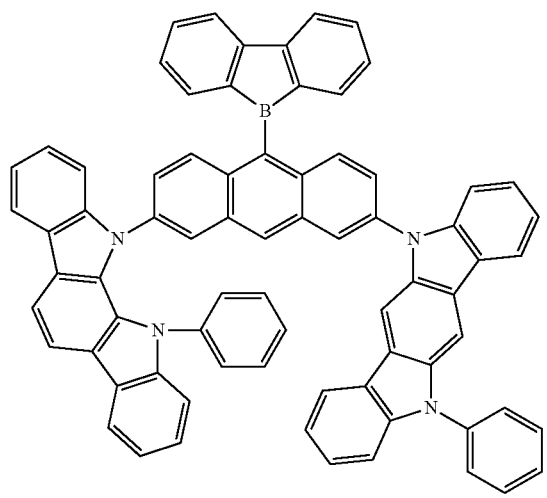
F24
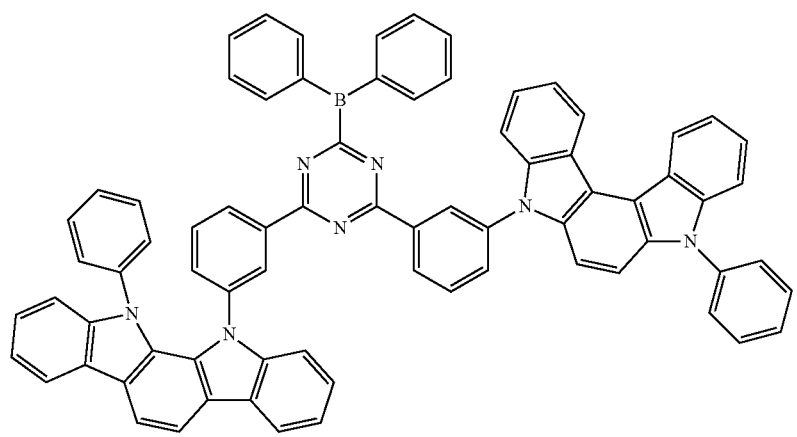
F25
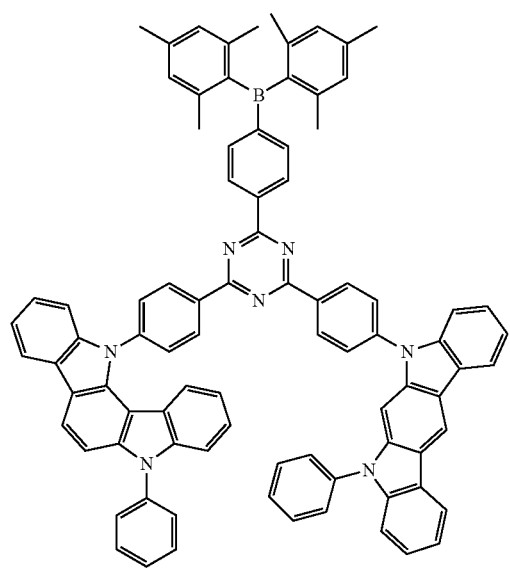
F26
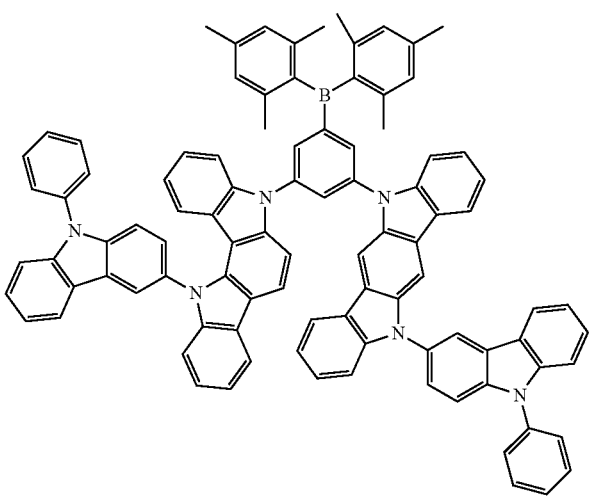
F27

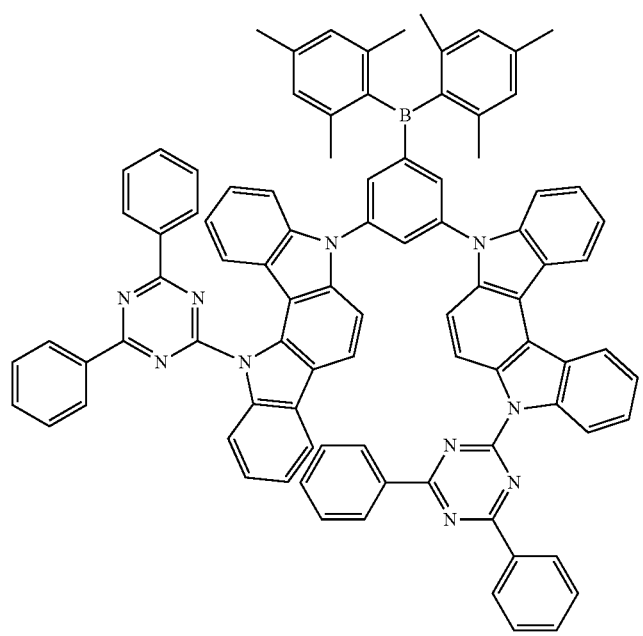
F28
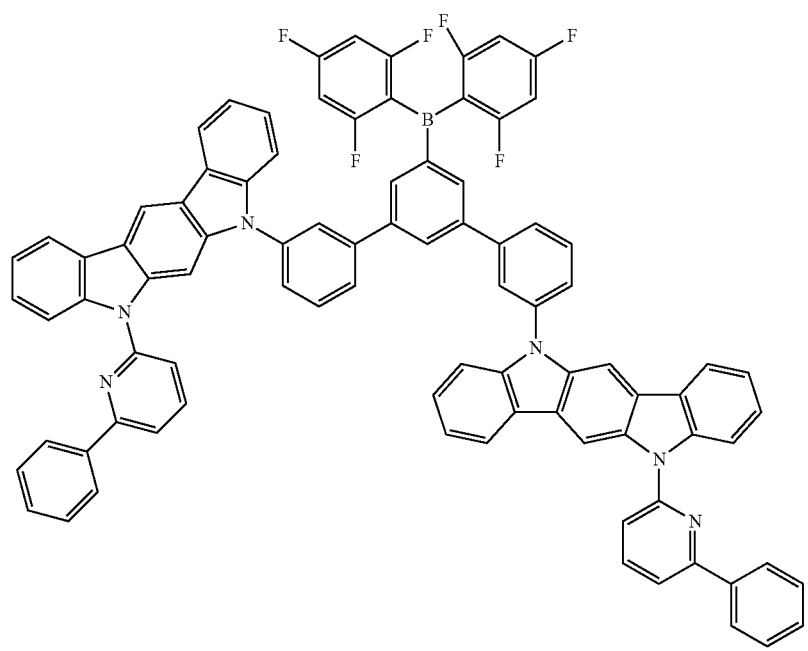
F29

-continued
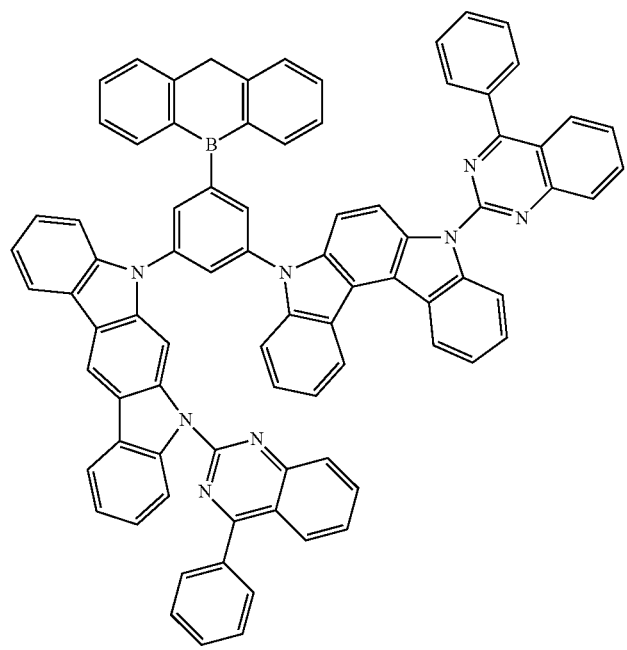
F30
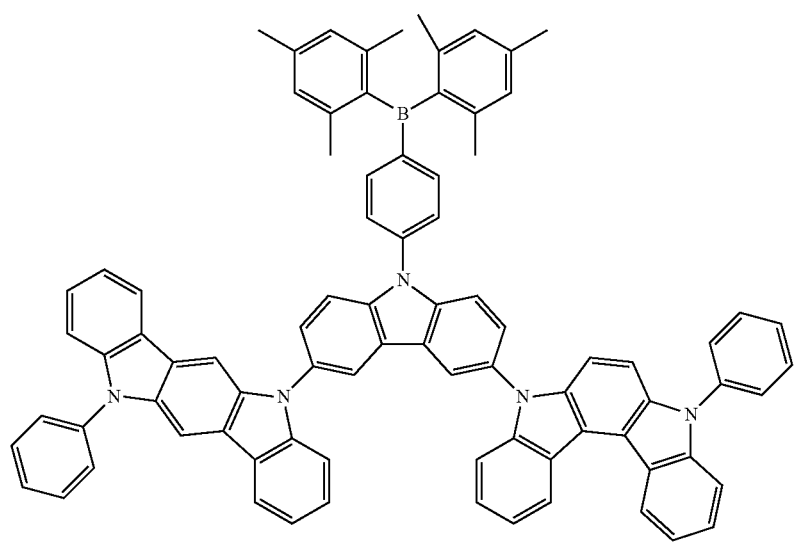
F31
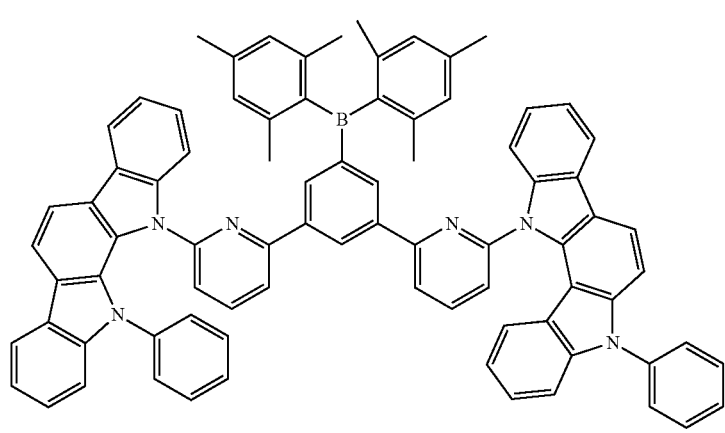
F32

-continued
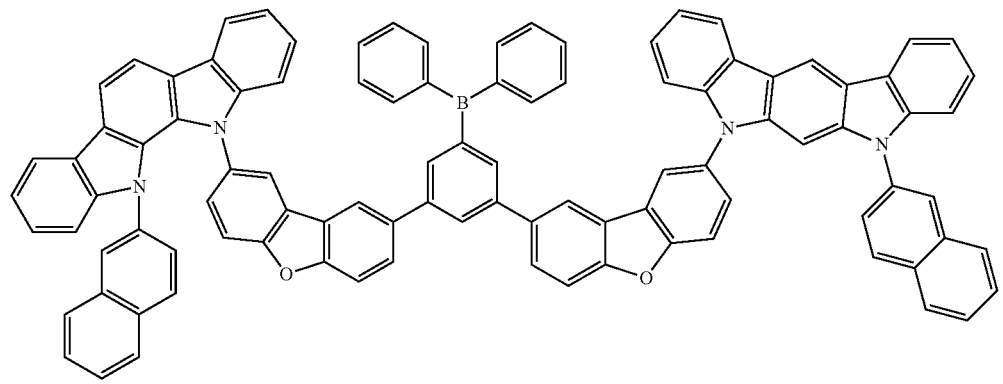
F33
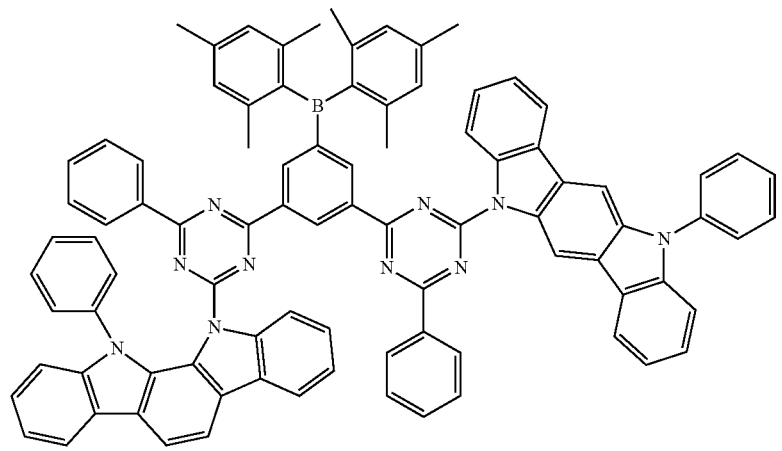
F34
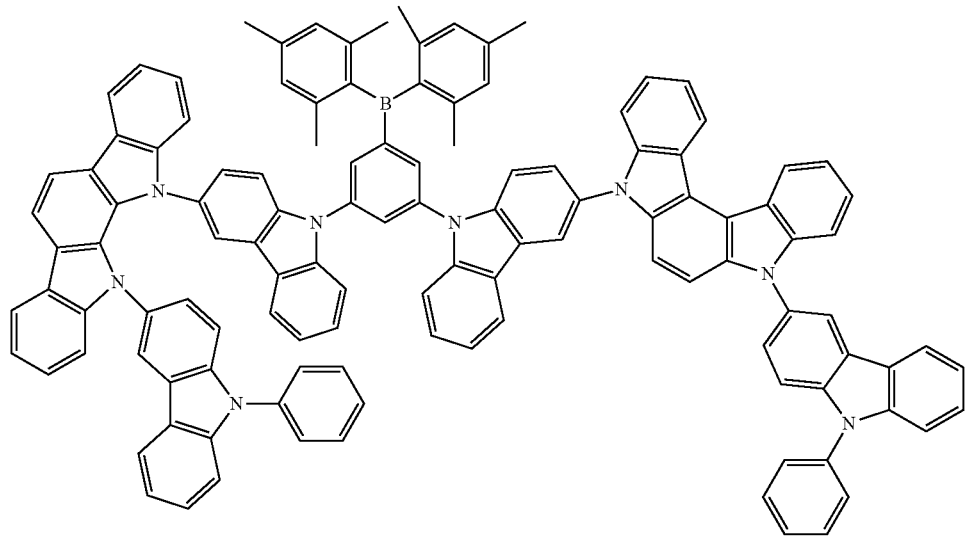
F35

-continued
F36
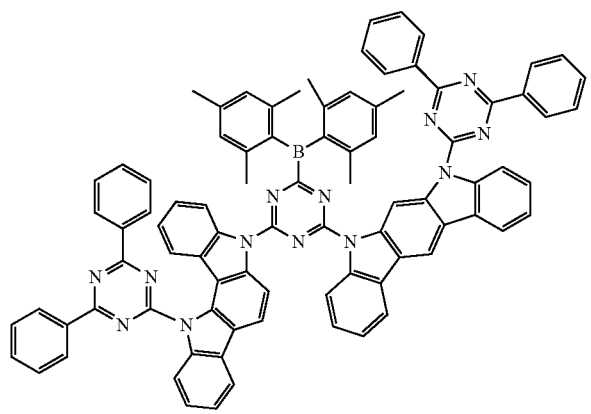
F37
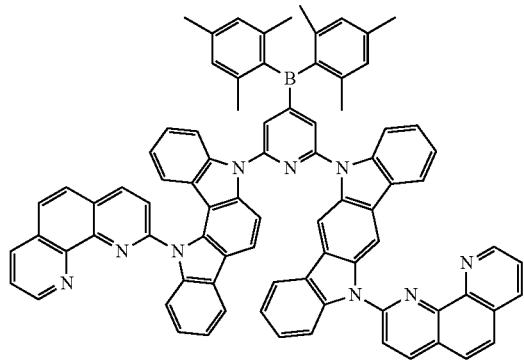
F38
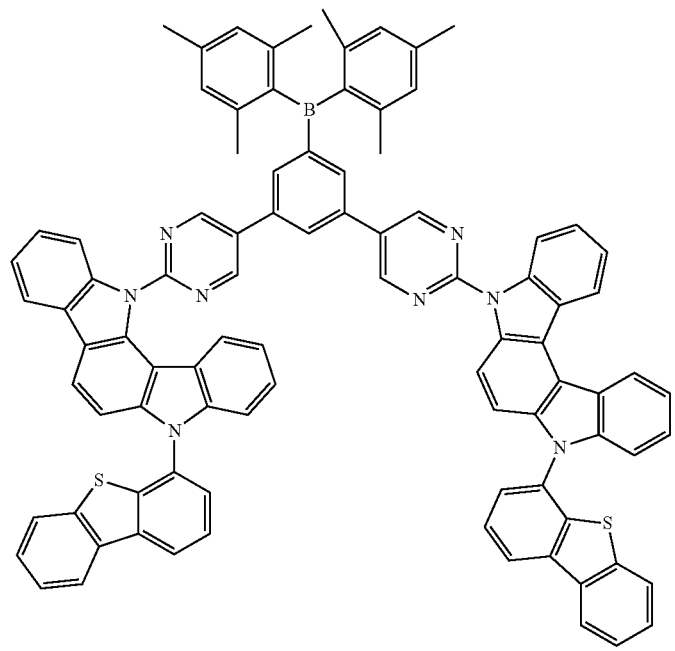
F39
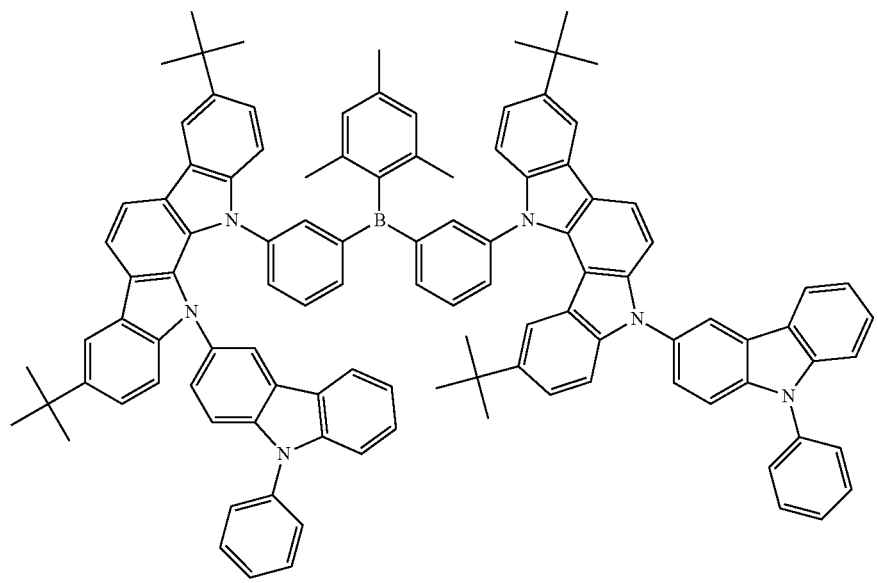

F40
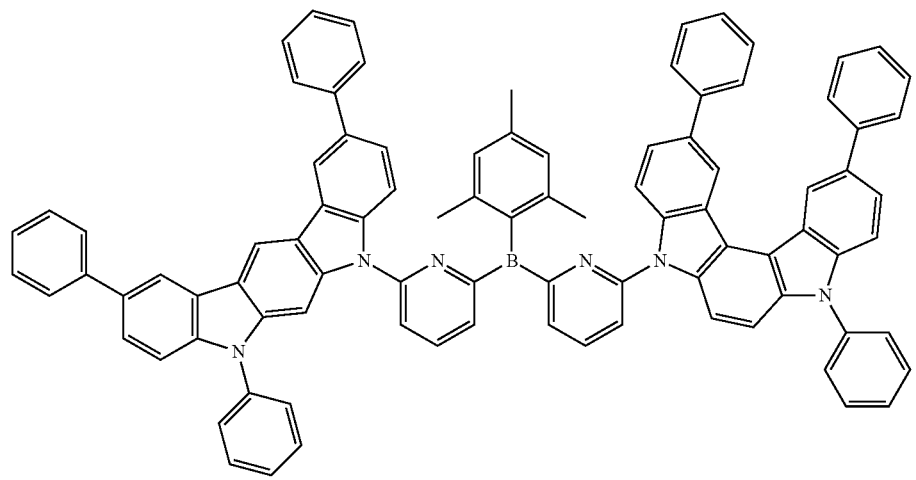
F41
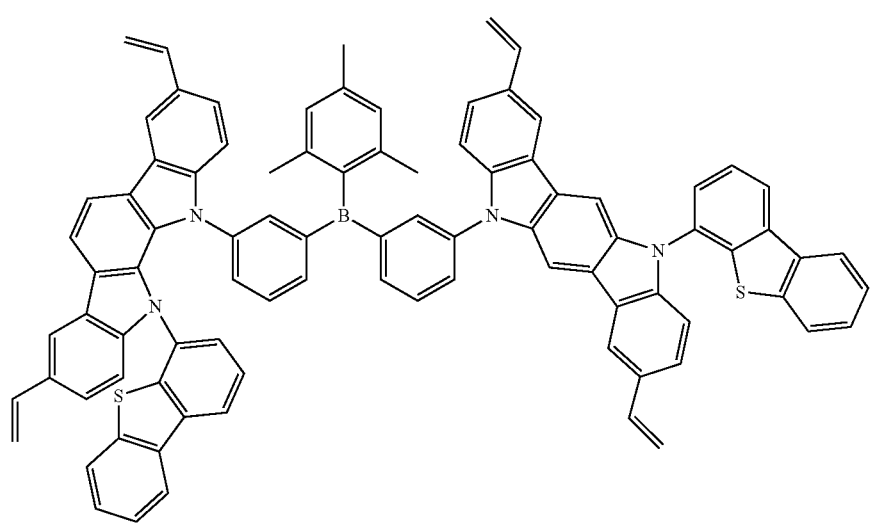
F42
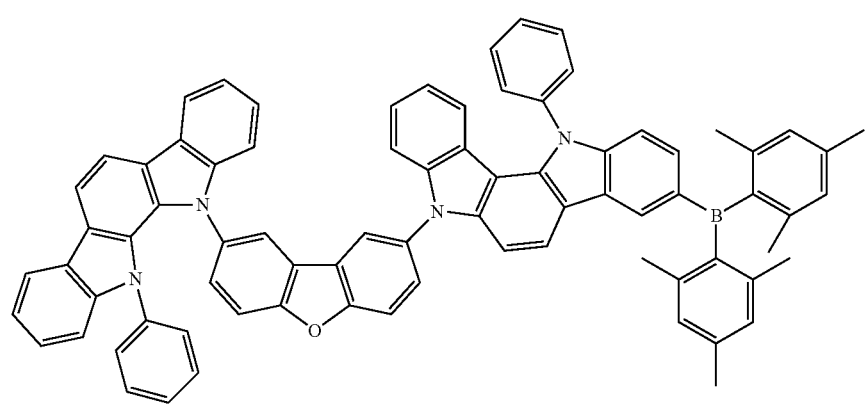

-continued

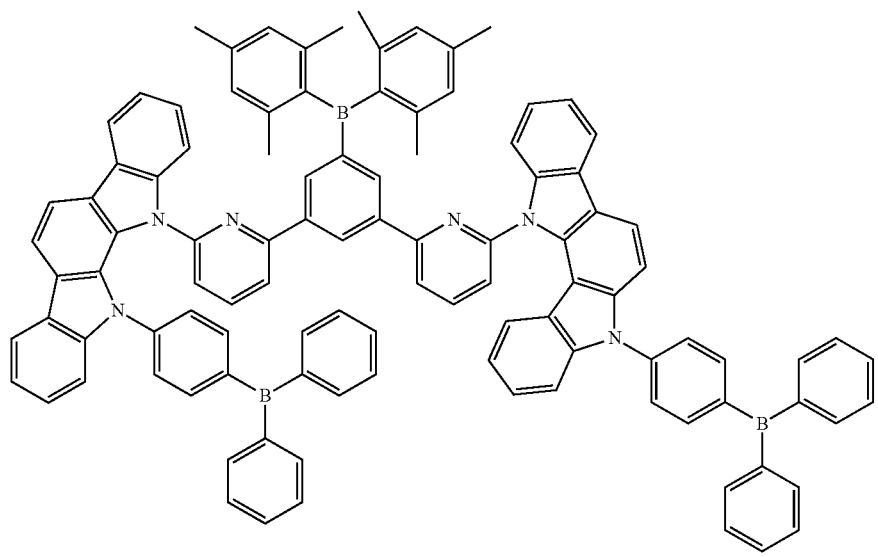

F43

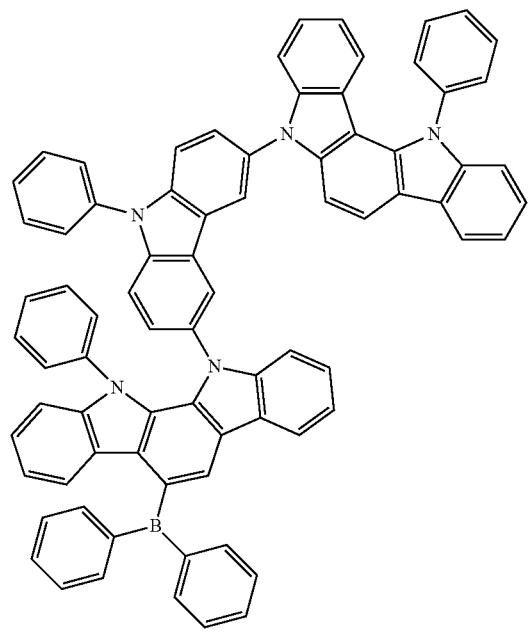

F44

The boron compound represented by the general formula (1) or (2) has two indolocarbazole structures and boron, and a preferred boron compound has one boron atom and two indolocarbazolyl groups. When the boron compound (hereinafter sometimes referred to as compound of the present invention) is contained in at least one of a plurality of organic layers of an organic EL device formed by laminating an anode, the plurality of organic layers, and a cathode on a substrate, an excellent organic EL device is provided. A light-emitting layer, a hole-transporting layer, an electron-transporting layer, a hole-blocking layer, or an electron-blocking layer is suitable as the organic layer in which the compound of the present invention is contained. Here, when the compound of the present invention is used in the light-emitting layer, the compound can be used as a host material for the light-emitting layer containing a fluorescent light-emitting, delayed fluorescent light-emitting, or phosphorescent light-emitting dopant. In addition, the compound of the present invention can be used as an organic light-emitting material which radiates fluorescence and delayed fluorescence. The compound of the present invention is particularly preferably incorporated as a host material for the light-emitting layer containing the phosphorescent light-emitting dopant.

Next, an organic EL device of the present invention is described.

The organic EL device of the present invention includes organic layers including at least one light-emitting layer between an anode and a cathode laminated on a substrate. In addition, at least one of the organic layers contains the boron compound. The compound for an organic EL device of the present invention is advantageously contained in the light-emitting layer together with a phosphorescent light-emitting dopant.

Next, the structure of the organic EL device of the present invention is described with reference to the drawings. However, the structure of the organic EL device of the present invention is by no means limited to one illustrated in the drawings.

FIG. 1 is a sectional view for illustrating a structure example of a general organic EL device used in the present invention. Reference numeral 1 represents a substrate, reference numeral 2 represents an anode, reference numeral 3 represents a hole-injecting layer, reference numeral 4 represents a hole-transporting layer, reference numeral 5 represents a light-emitting layer, reference numeral 6 represents an electron-transporting layer, and reference numeral 7 represents a cathode. The organic EL device of the present invention may include an exciton-blocking layer adjacent to the light-emitting layer, or may include an electron-blocking layer between the light-emitting layer and the hole-injecting layer. The exciton-blocking layer may be inserted on any of the anode side and the cathode side of the light-emitting layer, and may also be inserted simultaneously on both sides. The organic EL device of the present invention includes the substrate, the anode, the light-emitting layer, and the cathode as its essential layers. The organic EL device of the present invention preferably includes a hole-injecting/transporting layer and an electron-injecting/transporting layer in addition to the essential layers, and more preferably includes a hole-blocking layer between the light-emitting layer and the electron-injecting/transporting layer. It should be noted that the hole-injecting/transporting layer means any one or both of the hole-injecting layer and the hole-transporting layer, and that the electron-injecting/transporting layer means any one or both of an electron-injecting layer and the electron-transporting layer.

It should be noted that it is possible to adopt a reverse structure as compared to FIG. 1, that is, the reverse structure being formed by laminating the layers on the substrate 1 in the order of the cathode 7, the electron-transporting layer 6, the light-emitting layer 5, the hole-transporting layer 4, and the anode 2. In this case as well, some layers may be added or eliminated if necessary.

—Substrate—

The organic EL device of the present invention is preferably supported by a substrate. The substrate is not particularly limited, and any substrate which has long been conventionally used for an organic EL device may be used. For example, a substrate made of glass, a transparent plastic, quartz, or the like may be used.

—Anode—

Preferably used as the anode in the organic EL device is an anode formed by using, as an electrode substance, any of a metal, an alloy, an electrically conductive compound, and a mixture thereof, all of which have a large work function (4 eV or more). Specific examples of such electrode substance include metals such as Au and conductive transparent materials such as CuI, indium tin oxide (ITO), $SnO_2$, and ZnO. Further, it may be possible to use a material such as IDIXO ($In_2O_3$—ZnO), which may be used for producing an amorphous and transparent conductive film. In order to produce the anode, it may be possible to form any of those electrode substances into a thin film by using a method such as vapor deposition or sputtering and form a pattern having a desired shape thereon by photolithography. Alternatively, in the case of not requiring high pattern accuracy (about 100 μm or more), a pattern may be formed via a mask having a desired shape when any of the above-mentioned electrode substances is subjected to vapor deposition or sputtering. Alternatively, when a coatable substance such as an organic conductive compound is used, it is also possible to use a wet film-forming method such as a printing method or a coating method. When luminescence is taken out from the anode, the transmittance of the anode is desirably controlled to more than 10%. In addition, the sheet resistance as the anode is preferably several hundred Ω/□ (ohms per square) or less. Further, the thickness of the film is, depending on its material, selected from usually the range of from 10 nm to 1,000 nm, preferably the range of from 10 nm to 200 nm.

—Cathode—

On the other hand, used as the cathode is a cathode formed by using, as an electrode substance, any of a metal (referred to as electron-injecting metal), an alloy, an electrically conductive compound, and a mixture thereof, all of which have a small work function (4 eV or less). Specific examples of such electrode substance include sodium, a sodium-potassium alloy, magnesium, lithium, a magnesium/copper mixture, a magnesium/silver mixture, a magnesium/aluminum mixture, a magnesium/indium mixture, an aluminum/aluminum oxide ($Al_2O_3$) mixture, indium, a lithium/aluminum mixture, and a rare earth metal. Of those, for example, a mixture of an electron-injecting metal and a second metal as a stable metal having a larger work function value than the former metal, such as a magnesium/silver mixture, a magnesium/aluminum mixture, a magnesium/indium mixture, an aluminum/aluminum oxide ($Al_2O_3$) mixture, or a lithium/aluminum mixture, or aluminum is suitable from the viewpoints of electron-injecting property and durability against oxidation or the like. The cathode may be produced by forming any of those electrode substances into a thin film by using a method such as vapor deposition or sputtering. In addition, the sheet resistance as the cathode is preferably several hundred Ω/□ or less, and the thickness of the film is selected from usually the range of from 10 nm to 5 μm, preferably the range of from 50 nm to 200 nm. It should be noted that, in order for luminescence produced to pass through, any one of the anode and cathode of the organic EL device is preferably transparent or semi-transparent, because the light emission luminance improves.

In addition, after any of the above-mentioned metals is formed into a film having a thickness of from 1 nm to 20 nm as a cathode, any of the conductive transparent materials mentioned in the description of the anode is formed into a film on the cathode, thereby being able to produce a transparent or semi-transparent cathode. Then, by applying this, it is possible to produce a device in which both the anode and the cathode have transparency.

—Light-Emitting Layer—

The light-emitting layer is a layer which emits light after the production of an exciton by the recombination of a hole injected from the anode and an electron injected from the cathode, and the light-emitting layer desirably contains an organic light-emitting material and a host material.

When the light-emitting layer is a fluorescent light-emitting layer, a fluorescent light-emitting material can be used alone in the light-emitting layer. However, it is preferred that the fluorescent light-emitting material be used as a fluorescent light-emitting dopant and the host material be mixed.

The boron compound of the present invention can be used as the fluorescent light-emitting material in the light-emitting layer. However, the fluorescent light-emitting material is known through, for example, many patent literatures, and hence can be selected therefrom. Examples thereof include a benzoxazole derivative, a benzothiazole derivative, a benzimidazole derivative, a styrylbenzene derivative, a polyphenyl derivative, a diphenylbutadiene derivative, a tetraphenylbutadiene derivative, a naphthalimide derivative, a coumarine derivative, a fused aromatic compound, a perinone derivative, an oxadiazole derivative, an oxazine derivative, an aldazine derivative, a pyrrolidine derivative, a cyclopentadiene derivative, a bisstyrylanthracene derivative, a quinacridone derivative, a pyrrolopyridine derivative, a thiadiazolopyridine derivative, a styrylamine derivative, a diketopyrrolopyrrole derivative, an aromatic dimethylidene compound, various metal complexes typified by a metal complex of a 8-quinolinol derivative, and a metal complex, rare earth complex, or transition metal complex of a pyrromethene derivative, polymer compounds such as polythiophene, polyphenylene, and polyphenylene vinylene, and an organic silane derivative. Of those, for example, the following compound is preferred: a fused aromatic compound, a styryl compound, a diketopyrrolopyrrole compound, an oxazine compound, or a pyrromethene metal complex, transition metal complex, or lanthanoid complex. For example, the following compound is more preferred: naphthacene, pyrene, chrysene, triphenylene, benzo[c]phenanthrene, benzo[a]anthracene, pentacene, perylene, fluoranthene, acenaphthofluoranthene, dibenzo[a,j]anthracene, dibenzo[a,h]anthracene, benzo[a]naphthacene, hexacene, anthanthrene, naphtho[2,1-f]isoquinoline, α-naphthaphenanthridine, phenanthroxazole, quinolino[6,5-f]quinoline, or benzothiophanthrene. Those compounds may each have an alkyl group, aryl group, aromatic heterocyclic group, or diarylamino group as a substituent.

The boron compound of the present invention can be used as a fluorescent host material in the light-emitting layer. However, the fluorescent host material is known through, for example, many patent literatures, and hence can be selected therefrom. For example, the following material can be used: a compound having a fused aryl ring such as naphthalene, anthracene, phenanthrene, pyrene, chrysene, naphthacene, triphenylene, perylene, fluoranthene, fluorene, or indene, or a derivative thereof; an aromatic amine derivative such as N,N'-dinaphthyl-N,N'-diphenyl-4,4'-diphenyl-1,1'-diamine; a metal chelated oxinoid compound typified by tris(8-quinolinato)aluminum(III); a bisstyryl derivative such as a distyrylbenzene derivative; a tetraphenylbutadiene derivative; an indene derivative; a coumarin derivative; an oxadiazole derivative; a pyrrolopyridine derivative; a perinone derivative; a cyclopentadiene derivative; a pyrrolopyrrole derivative; a thiadiazolopyridine derivative; a dibenzofuran derivative; a carbazole derivative; an indolocarbazole derivative; a triazine derivative; or a polymer-based derivative such as a polyphenylene vinylene derivative, a poly-p-phenylene derivative, a polyfluorene derivative, a polyvinyl carbazole derivative, or a polythiophene derivative. However, the fluorescent host material is not particularly limited thereto.

When the fluorescent light-emitting material is used as a fluorescent light-emitting dopant and the host material is contained, the content of the fluorescent light-emitting dopant in the light-emitting layer desirably falls within the range of from 0.01 wt % to 20 wt %, preferably from 0.1 wt % to 10 wt %.

An organic EL device typically injects charges from both of its electrodes, i.e., its anode and cathode into a light-emitting substance to produce a light-emitting substance in an excited state, and causes the substance to emit light. In the case of a charge injection-type organic EL device, 25% of the produced excitons are said to be excited to a singlet excited state and the remaining 75% are said to be excited to a triplet excited state. As described in Advanced Materials 2009, 21, 4802-4806, it has been known that after a specific fluorescent light-emitting substance has undergone an energy transition to a triplet excited state as a result of intersystem crossing or the like, the substance is subjected to inverse intersystem crossing to a singlet excited state by triplet-triplet annihilation or the absorption of a thermal energy to radiate fluorescence, thereby expressing thermally activated delayed fluorescence. The organic EL device of the present invention can also express delayed fluorescence. In this case, the light emission can include both fluorescent light emission and delayed fluorescent light emission. It should be noted that light emission from the host material may be present in part of the light emission.

When the light-emitting layer is a delayed fluorescent light-emitting layer, a delayed fluorescent light-emitting material can be used alone in the light-emitting layer. However, it is preferred that the delayed fluorescent light-emitting material be used as a delayed fluorescent light-emitting dopant and the host material be mixed.

Although the boron compound of the present invention can be used as the delayed fluorescent light-emitting material in the light-emitting layer, a material selected from known delayed fluorescent light-emitting materials can also be used. Examples thereof include a tin complex, an indolocarbazole derivative, a copper complex, and a carbazole derivative. Specific examples thereof include, but not limited to, compounds described in the following non patent literatures and patent literature.

Adv. Mater. 2009, 21, 4802-4806, Appl. Phys. Lett. 98, 083302 (2011), JP 2011-213643 A, and J. Am. Chem. Soc. 2012, 134, 14706-14709.

Specific examples of the delayed fluorescent light-emitting material are shown below, but the delayed fluorescent light-emitting material is not limited to the following compounds.

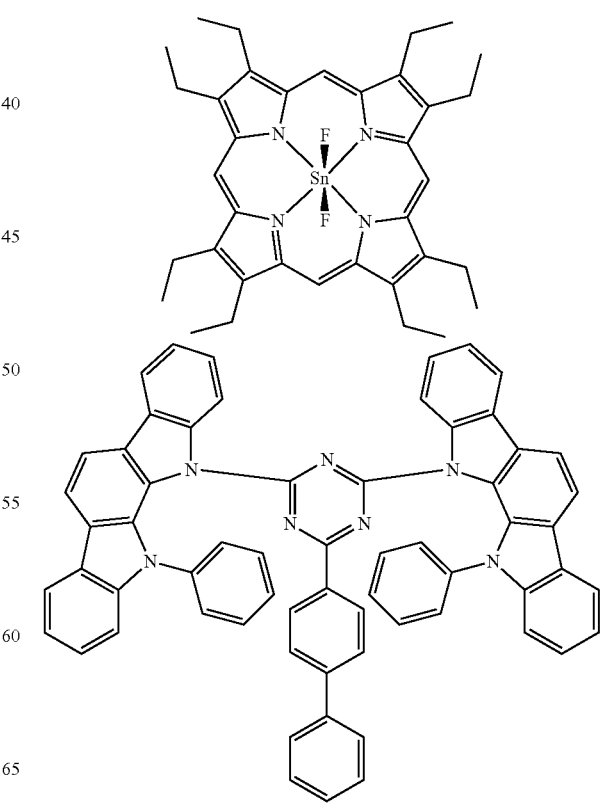

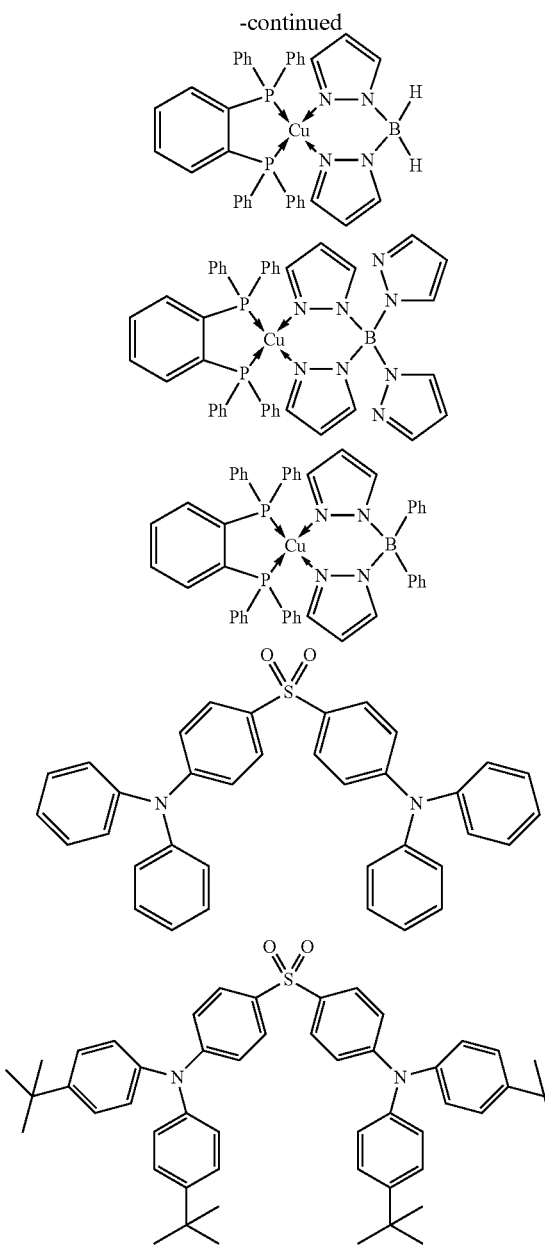

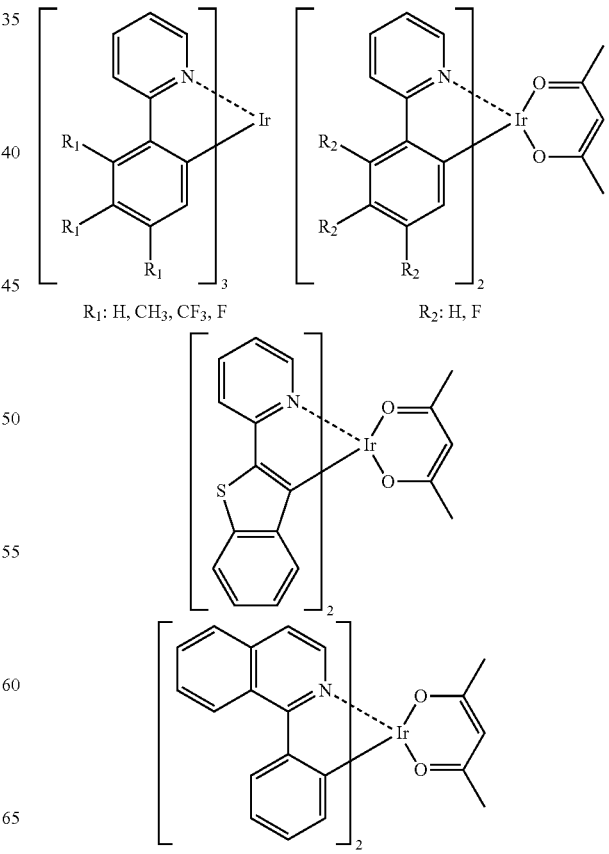

minum(III); a bisstyryl derivative such as a distyrylbenzene derivative; a tetraphenylbutadiene derivative; an indene derivative; a coumarin derivative; an oxadiazole derivative; a pyrrolopyridine derivative; a perinone derivative; a cyclopentadiene derivative; a pyrrolopyrrole derivative; a thiadiazolopyridine derivative; a dibenzofuran derivative; a carbazole derivative; an indolocarbazole derivative; a triazine derivative; or a polymer-based derivative such as a polyphenylene vinylene derivative, a poly-p-phenylene derivative, a polyfluorene derivative, a polyvinyl carbazole derivative, a polythiophene derivative, or an arylsilane derivative. However, the delayed fluorescent host material is not particularly limited thereto.

When the light-emitting layer is a phosphorescent light-emitting layer, the light-emitting layer contains a phosphorescent light-emitting dopant and a host material. It is recommended to use, as a material for the phosphorescent light-emitting dopant, a material containing an organic metal complex including at least one metal selected from ruthenium, rhodium, palladium, silver, rhenium, osmium, iridium, platinum, and gold. Specific examples thereof include, but not limited to, the compounds disclosed in the following patent publications.

WO 2009/073245 A1, WO 2009/046266 A1, WO 2007/095118 A2, WO 2008/156879 A1, WO 2008/140657 A1, and US 2008/261076 A1, and the like.

Preferred examples of the phosphorescent light-emitting dopant include complexes such as Ir(ppy)$_3$, complexes such as Ir(bt)2.acac3, and complexes such as PtOEt3, the complexes each having a noble metal element such as Ir as a central metal. Specific examples of those complexes are shown below, but the complexes are not limited to the compounds described below.

When the delayed fluorescent light-emitting material is used as a delayed fluorescent light-emitting dopant and the host material is contained, the content of the delayed fluorescent light-emitting dopant in the light-emitting layer desirably falls within the range of from 0.01 wt % to 50 wt %, preferably from 0.1 wt % to 20 wt %, more preferably from 0.01 wt % to 10%.

The boron compound of the present invention can be used as the delayed fluorescent host material in the light-emitting layer. However, the delayed fluorescent host material may be selected from compounds other than boron. For example, the following compound can be used: a compound having a fused aryl ring such as naphthalene, anthracene, phenanthrene, pyrene, chrysene, naphthacene, triphenylene, perylene, fluoranthene, fluorene, or indene, or a derivative thereof; an aromatic amine derivative such as N,N'-dinaphthyl-N,N'-diphenyl-4,4'-diphenyl-1,1'-diamine; a metal chelated oxinoid compound typified by tris(8-quinolinato)alu-

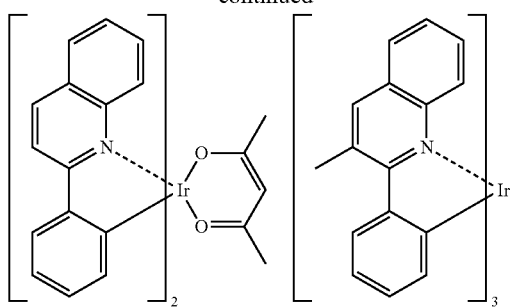
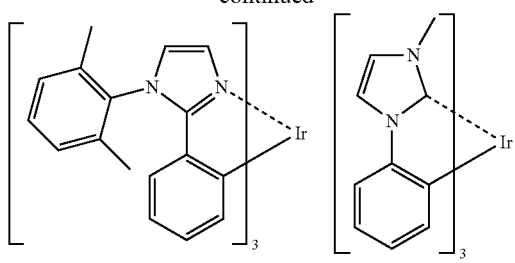
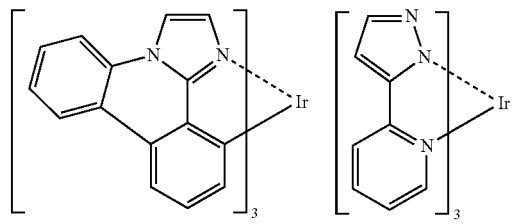
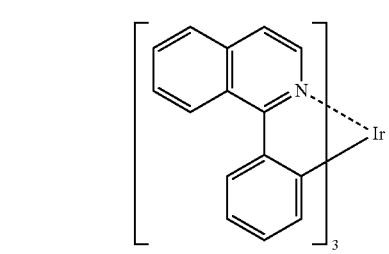
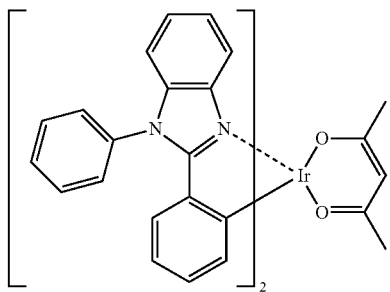
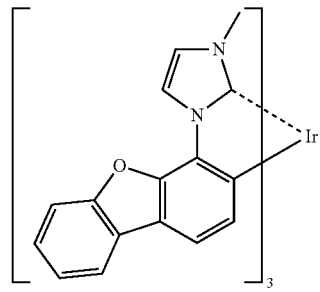
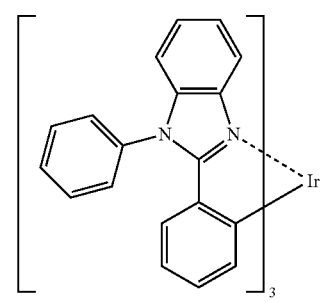
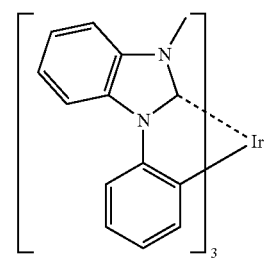
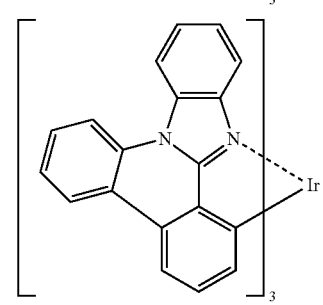
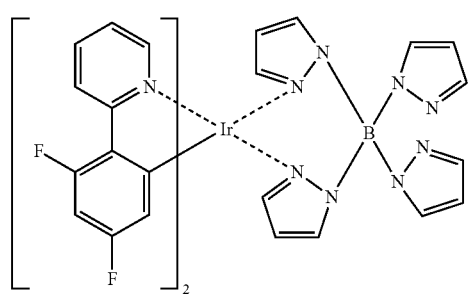
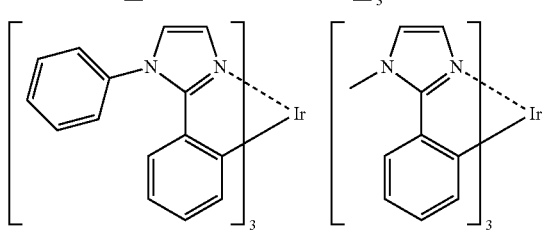
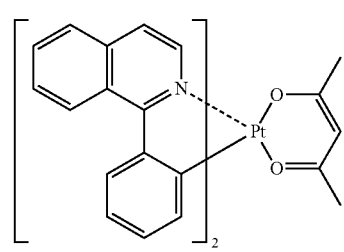

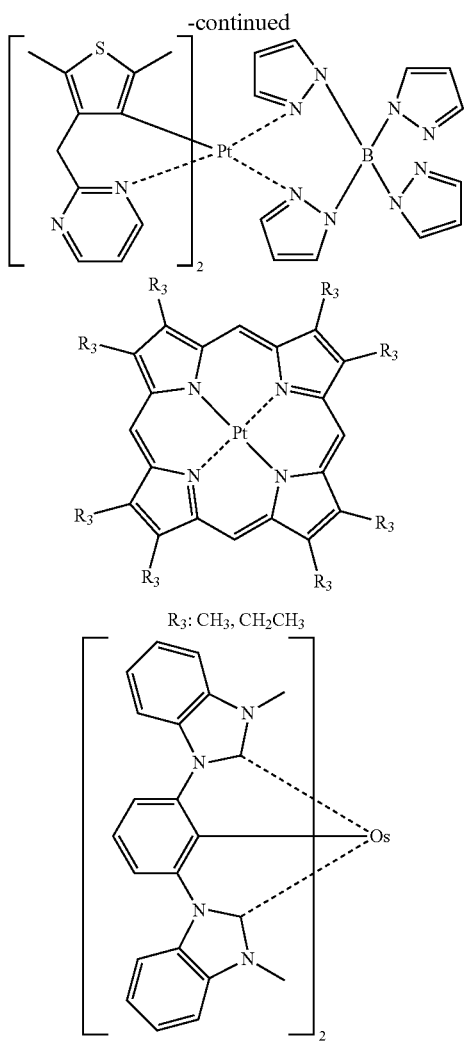

R$_3$: CH$_3$, CH$_2$CH$_3$

The content of the phosphorescent light-emitting dopant in the light-emitting layer desirably falls within the range of from 2 wt % to 40 wt %, preferably from 5 wt % to 30 wt %.

When the light-emitting layer is a phosphorescent light-emitting layer, it is preferred to use, as a host material in the light-emitting layer, the boron compound represented by the general formula (1). However, when the boron compound is used in any of the organic layers other than the light-emitting layer, the material to be used in the light-emitting layer may be another host material other than the boron compound, or the boron compound and any other host material may be used in combination. Further, a plurality of kinds of known host materials may be used in combination.

It is preferred to use, as a usable known host compound, a compound which has a hole-transporting ability or an electron-transporting ability, prevents luminescence from having a longer wavelength, and has a high glass transition temperature.

Such other host materials are known because they are mentioned in many patent literatures and the like, and hence a suitable host material may be selected from those in the patent literatures and the like. Specific examples of the host material include, but are not particularly limited to, an indole derivative, a carbazole derivative, a triazole derivative, an oxazole derivative, an oxadiazole derivative, an imidazole derivative, a polyarylalkane derivative, a pyrazoline derivative, a pyrazolone derivative, a phenylenediamine derivative, an arylamine derivative, an amino-substituted chalcone derivative, a styrylanthracene derivative, a fluorenone derivative, a hydrazone derivative, a stilbene derivative, a silazane derivative, an aromatic tertiary amine compound, a styrylamine compound, an aromatic dimethylidene-based compound, a porphyrin-based compound, an anthraquinodimethane derivative, an anthrone derivative, a diphenylquinone derivative, a thiopyran dioxide derivative, a heterocyclic tetracarboxylic acid anhydride such as naphthalene perylene, a phthalocyanine derivative, various metal complexes typified by a metal complex of an 8-quinolinol derivative, a metal phthalocyanine, and metal complexes of benzoxazole and benzothiazole derivatives, and polymer compounds such as a polysilane-based compound, a poly (N-vinylcarbazole) derivative, an aniline-based copolymer, a thiophene oligomer, a polythiophene derivative, a polyphenylene derivative, a polyphenylenevinylene derivative, and a polyfluorene derivative.

The light-emitting layer, which may be any one of a fluorescent light-emitting layer, a delayed fluorescent light-emitting layer, and a phosphorescent light-emitting layer, is preferably the phosphorescent light-emitting layer.

—Injecting Layer—

The injecting layer refers to a layer formed between an electrode and an organic layer for the purposes of lowering a driving voltage and improving light emission luminance, and includes a hole-injecting layer and an electron-injecting layer. The injecting layer may be interposed between the anode and the light-emitting layer or the hole-transporting layer, or may be interposed between the cathode and the light-emitting layer or the electron-transporting layer. The injecting layer may be formed as required.

—Hole-Blocking Layer—

The hole-blocking layer has, in a broad sense, the function of an electron-transporting layer, and is formed of a hole-blocking material which has a remarkably small ability to transport holes while having a function of transporting electrons, and hence the hole-blocking layer is capable of improving the probability of recombining an electron and a hole by blocking holes while transporting electrons.

It is preferred to use the boron compound of the present invention for the hole-blocking layer. However, when the boron compound is used in any other organic layer, a known material for a hole-blocking layer may be used. In addition, it is possible to use, as a material for the hole-blocking layer, any of materials for the electron-transporting layer to be described later, as required.

—Electron-Blocking Layer—

The electron-blocking layer has a role of blocking the arrival of electrons at the hole-transporting layer while transporting holes, and is formed of an electron-blocking material which has a remarkably small ability to transport electrons while having a function of transporting holes, and hence the electron-blocking layer is capable of improving the probability of recombining an electron and a hole by blocking electrons while transporting holes.

Although the boron compound of the present invention can be used as a material for the electron-blocking layer, another material, i.e., any of materials for the hole-transporting layer to be described later can be used as required. The thickness of the electron-blocking layer is preferably from 3 nm to 100 nm, more preferably from 5 nm to 30 nm.

—Exciton-Blocking Layer—

The exciton-blocking layer refers to a layer for blocking excitons produced by the recombination of a hole and an electron in the light-emitting layer from diffusing into charge-transporting layers. Inserting this layer enables effective confinement of the excitons in the light-emitting layer, thereby being able to improve the luminous efficiency of the device. The exciton-blocking layer may be inserted on any of the anode side and the cathode side of the adjacent light-emitting layer, and may also be inserted simultaneously on both sides.

Although the boron compound of the present invention can be used as a material for the exciton-blocking layer, as other materials therefor, there are given, for example, 1,3-dicarbazolylbenzene (mCP) and bis(2-methyl-8-quinolinolato)-4-phenylphenolatoaluminum(III) (BAlq).

—Hole-Transporting Layer—

The hole-transporting layer is formed of a hole-transporting material having a function of transporting holes, and a single hole-transporting layer or a plurality of hole-transporting layers may be formed.

The hole-transporting material has hole-injecting property or hole-transporting property or has electron-blocking property, and any of an organic material and an inorganic material may be used as the hole-transporting material. Although it is preferred to use the boron compound represented by the general formula (1) for the hole-transporting layer, any compound selected from conventionally known compounds may be used. Examples of the known hole-transporting material which may be used include a triazole derivative, an oxadiazole derivative, an imidazole derivative, a polyarylalkane derivative, a pyrazoline derivative, and a pyrazolone derivative, a phenylenediamine derivative, an arylamine derivative, an amino-substituted chalcone derivative, an oxazole derivative, a styrylanthracene derivative, a fluorenone derivative, a hydrazone derivative, a stilbene derivative, a silazane derivative, an aniline-based copolymer, and a conductive high-molecular weight oligomer, in particular, a thiophene oligomer. However, a porphyrin compound, an aromatic tertiary amine compound, or a styrylamine compound is preferably used, and an aromatic tertiary amine compound is more preferably used.

—Electron-Transporting Layer—

The electron-transporting layer is formed of a material having a function of transporting electrons, and a single electron-transporting layer or a plurality of electron-transporting layers may be formed.

An electron-transporting material (which also serves as a hole-blocking material in some cases) only needs to have a function of transferring electrons injected from the cathode into the light-emitting layer. Although it is preferred to use the material represented by the general formula (1) according to the present invention for the electron-transporting layer, any compound selected from conventionally known compounds may be used. Examples thereof include a nitro-substituted fluorene derivative, a diphenylquinone derivative, a thiopyran dioxide derivative, a carbodiimide, a fluorenylidenemethane derivative, anthraquinodimethane, an anthrone derivative, and an oxadiazole derivative. Further, it is also possible to use, as the electron-transporting material, a thiadiazole derivative prepared by substituting an oxygen atom on an oxadiazole ring with a sulfur atom in the oxadiazole derivative and a quinoxaline derivative which has a quinoxaline ring known as an electron withdrawing group. Further, it is also possible to use a polymer material in which any of those materials is introduced in a polymer chain or is used as a polymer main chain.

EXAMPLES

Hereinafter, the present invention is described in more detail by way of Examples. It should be appreciated that the present invention is not limited to Examples below and may be carried out in various forms as long as the various forms do not deviate from the gist of the present invention.

The route described below was used to synthesize a boron compound to be used as a material for a phosphorescent light-emitting device. It should be noted that the number of each compound corresponds to the number given to the exemplified compound.

Synthesis Example 1

Synthesis of Compound B14

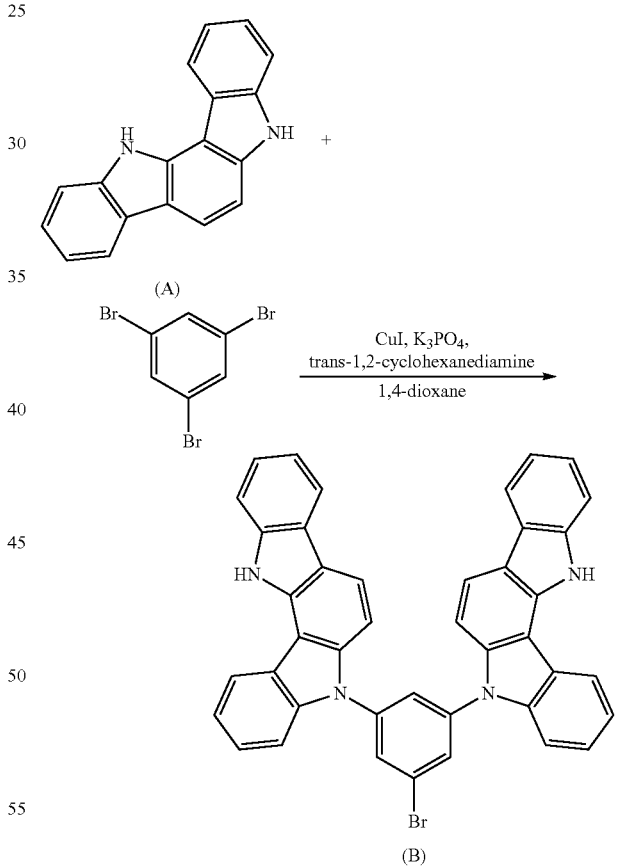

Under a nitrogen atmosphere, 10.00 g (0.0390 mol) of a compound (A), 6.14 g (0.0195 mol) of tribromobenzene, 0.74 g of copper iodide, 24.84 g of potassium triphosphate, and 500 ml of 1,4-dioxane were loaded and stirred at room temperature. 1.34 g of trans-1,2-cyclohexanediamine was added to the mixture and the whole was stirred at 110° C. for 9 hr. The reaction solution was cooled to room temperature and filtered, followed by concentration. The resultant residue was purified by silica gel column chromatography to provide 3.00 g (0.00451 mol, yield: 12%) of an intermediate (B) as a white solid.

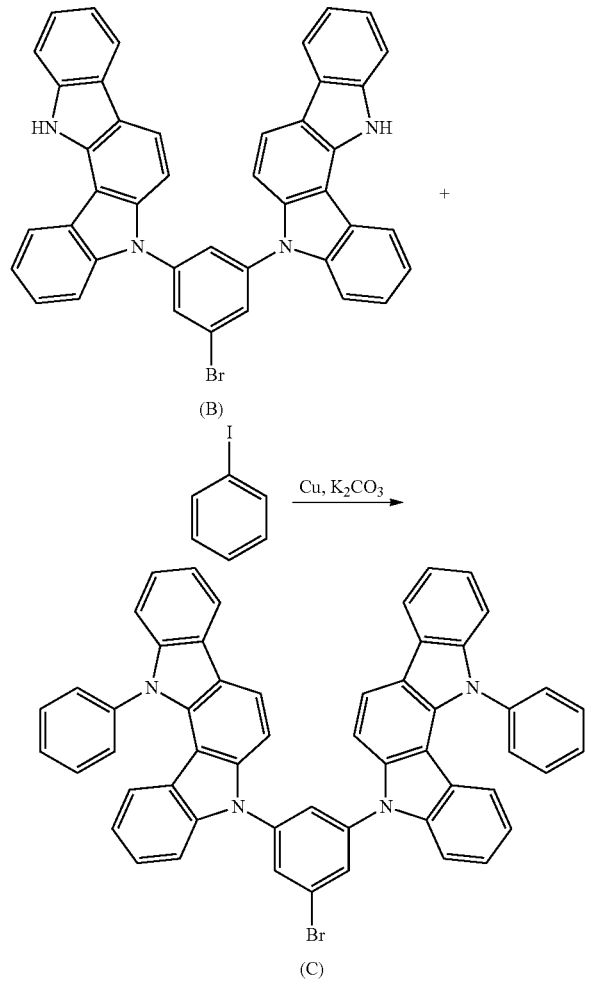

(B)

(C)

Under a nitrogen atmosphere, 3.00 g (0.00451 mol) of the intermediate (B), 110.41 g (0.5412 mol) of iodobenzene, 1.89 g of copper, and 6.86 g of potassium carbonate were loaded and stirred at 180° C. for 5 hr. The reaction solution was cooled to room temperature and filtered, followed by concentration. The resultant residue was purified by silica gel column chromatography to provide 3.50 g (0.00428 mol, yield: 95%) of a compound (C) as a white solid.

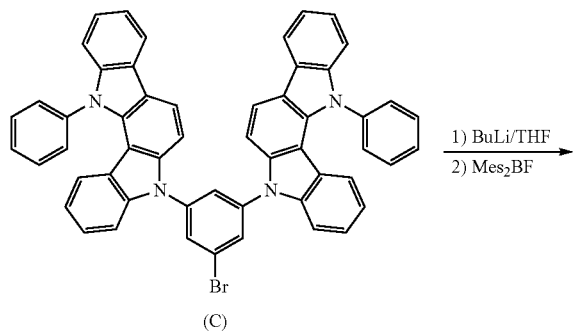

(C)

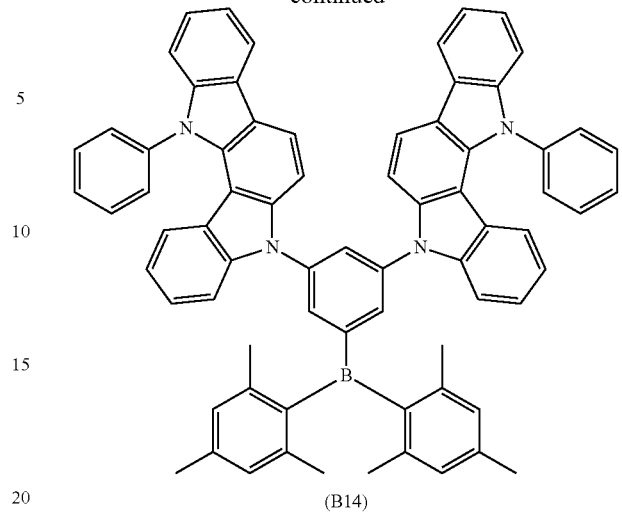

(B14)

Under a nitrogen atmosphere, 3.50 g (0.00428 mol) of the intermediate (C) and 50 ml of THF were added and cooled to −60° C. 3.2 ml of 1.59 M n-BuLi was added to the mixture, and the whole was stirred at −60° C. for 30 min. After that, 5.000 g (0.0186 mol) of dimesitylfluoroborane was added to the resultant and the mixture was stirred at room temperature for 22 hr. After that, the solvent was removed, and the resultant residue was purified by silica gel column chromatography and recrystallization to provide 1.86 g (0.00188 mol, yield: 44%) of a compound B14 as a yellow solid.

Figure 2:
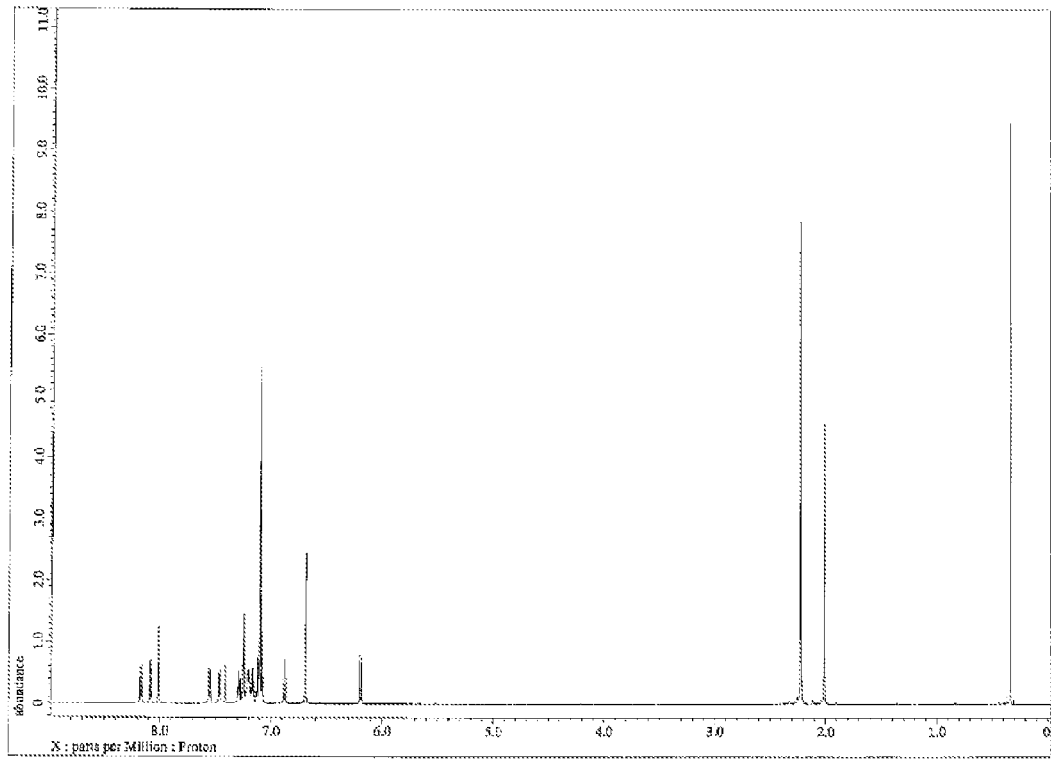
FIG. 2 is a view for showing a $^1$H-NMR chart of a boron compound for an organic electroluminescent device.

The APCI-TOFMS of the compound showed an [M+1] peak at an m/z of 988. The results of its 1H-NMR measurement (measurement solvent: C6D6) are shown in FIG. 2.

Example 1

Each thin film was laminated by a vacuum deposition method at a degree of vacuum of $4.0 \times 10^{-5}$ Pa on a glass substrate on which an anode formed of ITO having a thickness of 110 nm had been formed. First, copper phthalocyanine (CuPC) was formed into a layer having a thickness of 25 nm on the ITO. Next, 4,4'-bis[N-(1-naphthyl)-N-phenylamino]biphenyl (NPB) was formed into a layer having a thickness of 40 nm to serve as a hole-transporting layer. Next, the compound (B14) as a host material and tris(2-phenylpyridine)iridium(III) (Ir(ppy)$_3$) as a phosphorescent light-emitting dopant were co-deposited from different deposition sources onto the hole-transporting layer to form a light-emitting layer having a thickness of 40 nm. The concentration of Ir(ppy)$_3$ in the light-emitting layer was 10.0 wt %. Next, tris(8-hydroxyquinolinato)aluminum(III) (Alq3) was formed into a layer having a thickness of 20 nm to serve as an electron-transporting layer. Further, lithium fluoride (LiF) was formed into a layer having a thickness of 1.0 nm to serve as an electron-injecting layer on the electron-transporting layer. Finally, aluminum (Al) was formed into a layer having a thickness of 70 nm to serve as an electrode on the electron-injecting layer. Thus, an organic EL device was produced.

An external power source was connected to the resultant organic EL device to apply a DC voltage to the device. As a result, it was confirmed that the device had such light-emitting characteristics as shown in Table 1. The columns "luminance", "voltage", and "luminous efficiency" in Table 1 show values at 20 mA/cm². It was found that the local maximum wavelength of the emission spectrum of the device was 520 nm and hence light emission from Ir(ppy)₃ was obtained.

Examples 2 to 12

Compounds A8, A15, A24, B5, B6, B24, C8, D37, E25, F28, and F32 were synthesized in the same manner as in Synthesis Example 1.

Organic EL devices were each produced in the same manner as in Example 1 except that the compounds A8, A15, A24, B5, B6, B24, C8, D37, E25, F28, and F32 were each used instead of the compound B14 as the host material for the light-emitting layer of Example 1. It was found that the local maximum wavelength of the emission spectrum of each of the devices was 520 nm, and hence light emission from Ir(ppy)₃ was obtained. The respective light-emitting characteristics are shown in Table 1.

Comparative Example 1

An organic EL device was produced in the same manner as in Example 1 except that CBP was used as the host material for the light-emitting layer.

Comparative Example 2

An organic EL device was produced in the same manner as in Example 1 except that the following compound Ho-1 was used as the host material for the light-emitting layer.

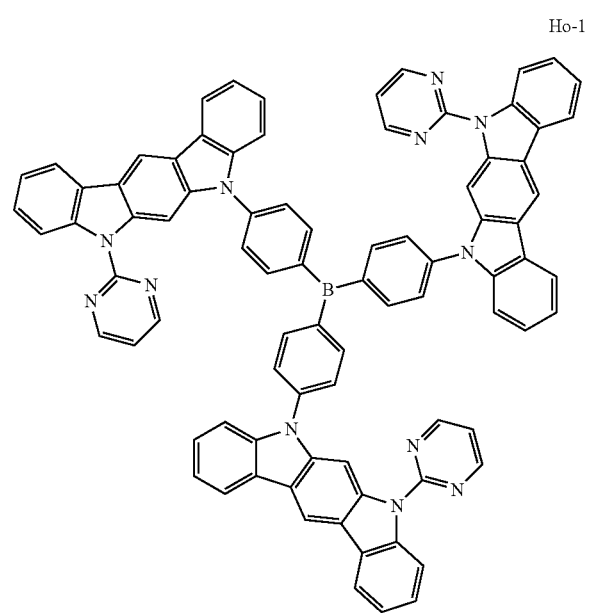 [SMILES: c1cnc(-n2c3ccccc3c3cc4c5ccccc5n(-c5ccc(B(c6ccc(-n7c8ccccc8c8cc9c%10ccccc%10n(-c%10ncccn%10)c9cc87)cc6)c6ccc(-n7c8ccccc8c8cc9c%10ccccc%10n(-c%10ncccn%10)c9cc87)cc6)cc5)c4cc32)nc1]

Ho-1

It was found that the local maximum wavelength of the emission spectrum of each of the organic EL devices produced in Comparative Examples 1 and 2 was 520 nm, and hence light emission from Ir(ppy)₃ was obtained. The compounds each used as the host material and the respective light-emitting characteristics are shown in Table 1.

TABLE 1

|  | Compound | Luminance (cd/m²) | Voltage (V) | Visual luminous efficiency (lm/W) |
|---|---|---|---|---|
| Example |  |  |  |  |
| 1 | B14 | 4,980 | 5.8 | 13.5 |
| 2 | A8 | 5,000 | 5.5 | 14.3 |
| 3 | A15 | 5,020 | 5.6 | 14.1 |
| 4 | A24 | 4,985 | 5.4 | 14.5 |
| 5 | B5 | 5,135 | 5.6 | 14.4 |
| 6 | B6 | 5,005 | 5.4 | 14.6 |
| 7 | B24 | 5,285 | 6.2 | 13.4 |
| 8 | C8 | 5,190 | 5.6 | 14.6 |
| 9 | D37 | 5,005 | 5.5 | 14.3 |
| 10 | D45 | 4,860 | 5.9 | 12.9 |
| 11 | E25 | 5,130 | 5.6 | 14.4 |
| 12 | E41 | 4,810 | 5.8 | 13.0 |
| 13 | F28 | 4,985 | 6.0 | 13.1 |
| 14 | F32 | 4,780 | 5.7 | 13.2 |
| Comparative Example |  |  |  |  |
| 1 | CBP | 4,860 | 9.3 | 8.2 |
| 2 | Ho-1 | 4,700 | 7.4 | 10.0 |

It is found from Table 1 that the organic EL device using the boron compound of the present invention has a low driving voltage and shows good light-emitting characteristics as compared to those in the case where CBP generally known as a phosphorescent host is used. It is also found that the device shows good light-emitting characteristics as compared to those in the case where Ho-1 as a compound having three indolocarbazolyl groups linked through a boron substituent is used. The superiority of the organic EL device using the boron compound is apparent from the foregoing.

INDUSTRIAL APPLICABILITY

The organic EL device of the present invention has light-emitting characteristics, driving voltage, and durability at practically satisfactory levels. Thus, the organic EL device has a large technical value in applications to flat panel displays (display devices for mobile phones, in-vehicle display devices, display devices for OA computers, televisions, and the like), light sources utilizing characteristics of planar light emitters (light sources in lighting equipment and copying machines and backlight sources in liquid crystal displays and instruments), sign boards, sign lamps, and the like.

The invention claimed is:

1. A boron compound for an organic electroluminescent device, which is represented by the following general formula (1) or (2):

(1)

(2)

(1a)

wherein, in formula (1), L₁'s each independently represents a divalent or trivalent group selected from a substituted or unsubstituted aromatic hydrocarbon group having 6 to 18 carbon atoms, a substituted or unsubstituted aromatic heterocyclic group having 3 to 17 carbon atoms, and a linked aromatic group formed by linking 2 to 6 aromatic rings of the substituted or unsubstituted aromatic hydrocarbon group and the substituted or unsubstituted aromatic heterocyclic group, the linked aromatic group are linear or branched, and the aromatic rings to be linked are identical to or different from each other;

in formula (2), Z represents a boron-containing group represented by the formula (1a);

in formula (1a), A's each independently represents hydrogen, deuterium, an alkyl group having 1 to 12 carbon atoms, an alkenyl group having 2 to 12 carbon atoms, an alkynyl group having 2 to 12 carbon atoms, an alkoxyl group having 1 to 12 carbon atoms, a hydroxyl group, chlorine, bromine, fluorine, a substituted or unsubstituted aromatic hydrocarbon group having 6 to 18 carbon atoms, or a substituted or unsubstituted aromatic heterocyclic group having 3 to 17 carbon atoms, and when A represents an alkyl group, an alkenyl group, an alkynyl group, an alkoxyl group, an aromatic hydrocarbon group, or an aromatic heterocyclic group, the groups adjacent to each other or substituents of the groups are optionally bonded to each other to form a ring, and the ring is optionally a heterocycle containing B or is optionally a fused ring;

in formulae (1) and (2), Y's each independently represents an indolocarbazolyl group represented by the following formula (1 b):

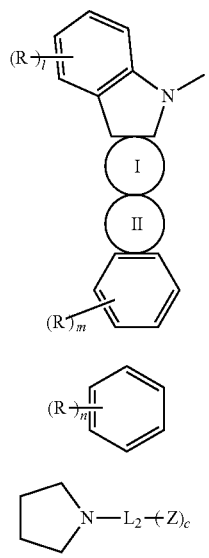

(Ib)

(Ic)

(Id)

wherein, ring I of formula (1b) represents an aromatic hydrocarbon ring represented by the formula (1c), which fuses with an adjacent ring at an arbitrary position, ring II of formula (1b) represents a heterocycle represented by the formula (1d), which fuses with an adjacent ring at an arbitrary position, and $L_2$ has the same meaning as that of $L_1$ described above but represents a c+1-valent group;

Z of formula (1d) has the same meaning as that of Z in the general formula (2), and when a plurality of Z's exist, the plurality of Z's are identical to or different from each other;

R of formulae (1 b) and (1c) represents deuterium, an alkyl group having 1 to 12 carbon atoms, an aralkyl group having 7 to 19 carbon atoms, an alkenyl group having 2 to 12 carbon atoms, an alkynyl group having 2 to 12 carbon atoms, a cyano group, a dialkylamino group having 2 to 24 carbon atoms, a diarylamino group having 6 to 36 carbon atoms, a diaralkylamino group having 14 to 38 carbon atoms, an amino group, a nitro group, an acyl group having 2 to 12 carbon atoms, an alkoxycarbonyl group having 2 to 12 carbon atoms, a carboxyl group, an alkoxyl group having 1 to 12 carbon atoms, an alkylsulfonyl group having 1 to 12 carbon atoms, a haloalkyl group having 1 to 12 carbon atoms, a hydroxyl group, an amide group, a phenoxy group, an alkylthio group having 1 to 12 carbon atoms, a substituted or unsubstituted aromatic hydrocarbon group having 6 to 18 carbon atoms, a substituted or unsubstituted aromatic heterocyclic group having 3 to 17 carbon atoms, or a boron-containing group represented by the formula (1a);

l and m each independently represents an integer of from 0 to 4, and n represents an integer of from 0 to 2; and a and b each represents an integer of 0 or 1, and c represents an integer of from 0 to 5, provided that in the general formula (1), l+m+n+a+c≥1, and in the general formula (2), l+m+n+b+c≥1, and when a+c or b+c equals 0, at least one R represents a boron-containing group represented by the formula (1a), and when l, m, n, b, or c represents 2 or more, a plurality of R's or Z's are identical to or different from each other.

2. A boron compound for an organic electroluminescent device according to claim 1, wherein in the general formulae (1) and (2), Y's each represents an indolocarbazolyl group represented by any one of the general formulae (3) to (6):

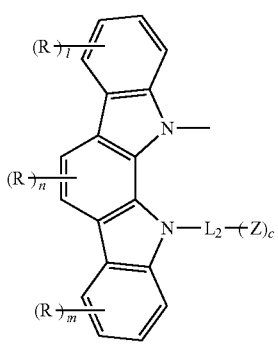

(3)

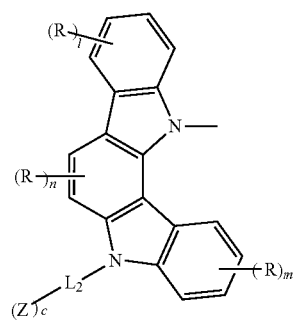

(4)

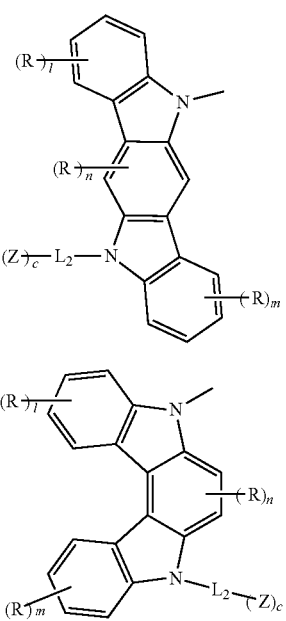

wherein, $L_2$, Z, R, l, m, n, and c each have the same meaning as that in the formula (1b).

3. A boron compound for an organic electroluminescent device according to claim 1, wherein A's each independently represents an alkyl group having 1 to 12 carbon atoms, a substituted or unsubstituted aromatic hydrocarbon group having 6 to 18 carbon atoms, or a substituted or unsubstituted aromatic heterocyclic group having 3 to 17 carbon atoms.

4. A boron compound for an organic electroluminescent device according to claim 1, wherein at least one of $L_1$ or $L_2$ represents a group having a fused ring structure.

5. An organic electroluminescent device, comprising an organic layer containing the boron compound for an organic electroluminescent device of claim 1.

6. An organic electroluminescent device according to claim 5, wherein the organic layer containing the boron compound for an organic electroluminescent device is at least one layer selected from a light-emitting layer, a hole-transporting layer, a hole-injecting layer, an electron-transporting layer, and an electron-injecting layer.

7. An organic electroluminescent device according to claim 5, wherein the organic layer containing the boron compound for an organic electroluminescent device is a light-emitting layer, and the light-emitting layer contains a phosphorescent light-emitting dopant and the boron compound for an organic electroluminescent device as a host material.

8. An organic electroluminescent device, comprising an organic layer containing the boron compound for an organic electroluminescent device of claim 2.

9. An organic electroluminescent device according to claim 8, wherein the organic layer containing the boron compound for an organic electroluminescent device is a light-emitting layer, and the light-emitting layer contains a phosphorescent light-emitting dopant and the boron compound for an organic electroluminescent device as a host material.

* * * * *